(12) United States Patent
Kotake et al.

(10) Patent No.: US 10,725,377 B2
(45) Date of Patent: *Jul. 28, 2020

(54) CHEMICALLY AMPLIFIED NEGATIVE RESIST COMPOSITION AND RESIST PATTERN FORMING PROCESS

(71) Applicant: Shin-Etsu Chemical Co., Ltd., Tokyo (JP)

(72) Inventors: Masaaki Kotake, Joetsu (JP); Satoshi Watanabe, Joetsu (JP); Keiichi Masunaga, Joetsu (JP); Kenji Yamada, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/854,990

(22) Filed: Dec. 27, 2017

(65) Prior Publication Data

US 2018/0180998 A1  Jun. 28, 2018

(30) Foreign Application Priority Data

Dec. 28, 2016  (JP) .................................. 2016-255025

(51) Int. Cl.
| | | |
|---|---|---|
| G03F 7/038 | (2006.01) | |
| G03F 7/004 | (2006.01) | |
| G03F 7/30 | (2006.01) | |
| C07C 381/12 | (2006.01) | |
| C07C 317/04 | (2006.01) | |
| C07C 317/28 | (2006.01) | |
| C07C 303/32 | (2006.01) | |
| C07C 323/20 | (2006.01) | |
| C08F 212/14 | (2006.01) | |
| G03F 7/32 | (2006.01) | |
| G03F 7/20 | (2006.01) | |
| G03F 7/039 | (2006.01) | |

(52) U.S. Cl.
CPC .......... *G03F 7/0045* (2013.01); *C07C 303/32* (2013.01); *C07C 317/04* (2013.01); *C07C 317/28* (2013.01); *C07C 323/20* (2013.01); *C07C 381/12* (2013.01); *C08F 212/14* (2013.01); *G03F 7/0382* (2013.01); *G03F 7/2002* (2013.01); *G03F 7/2053* (2013.01); *G03F 7/2059* (2013.01); *G03F 7/30* (2013.01); *G03F 7/322* (2013.01); *C07C 2601/16* (2017.05); *C08F 2800/10* (2013.01); *G03F 7/039* (2013.01); *G03F 7/0392* (2013.01); *G03F 7/0397* (2013.01); *G03F 7/20* (2013.01); *G03F 7/2004* (2013.01); *G03F 7/327* (2013.01)

(58) Field of Classification Search
CPC ..... G03F 7/0045; G03F 7/033; C07C 381/12; C07C 317/04; C07C 317/28; C07C 303/32

USPC .............. 430/270.1, 905, 910; 562/100, 113; 568/34, 35

See application file for complete search history.

(56) References Cited

U.S. PATENT DOCUMENTS

| | | | |
|---|---|---|---|
| 6,479,210 B2 | 11/2002 | Kinoshita et al. | |
| 6,485,883 B2 | 11/2002 | Kodama et al. | |
| 6,492,091 B2 | 12/2002 | Kodama et al. | |
| 7,214,467 B2 | 5/2007 | Kanna et al. | |
| 8,202,677 B2 | 6/2012 | Takeda et al. | |
| 8,785,105 B2* | 7/2014 | Ohsawa | C07C 309/12 430/270.1 |
| 9,075,306 B2 | 7/2015 | Takeda et al. | |
| 9,233,919 B2* | 1/2016 | Ohsawa | C07C 309/12 |
| 9,250,518 B2* | 2/2016 | Hatakeyama | G03F 7/0046 |
| 10,173,975 B2* | 1/2019 | Ohashi | C08F 220/24 |
| 2006/0166133 A1 | 7/2006 | Koitabashi et al. | |
| 2018/0180992 A1* | 6/2018 | Kotake | G03F 7/0045 |

FOREIGN PATENT DOCUMENTS

| | | |
|---|---|---|
| EP | 1684118 A1 | 7/2006 |
| EP | 1975711 A1 | 10/2008 |
| JP | 11-327143 A | 11/1999 |
| JP | 2006-201532 A | 8/2006 |
| JP | 2006-215180 A | 8/2006 |
| JP | 3955384 B2 | 8/2007 |
| JP | 4116340 B2 | 7/2008 |
| JP | 2008-249762 A | 10/2008 |
| JP | 4226803 B2 | 2/2009 |
| JP | 4231622 B2 | 3/2009 |
| JP | 4575479 B2 | 11/2010 |

* cited by examiner

*Primary Examiner* — John S Chu

(74) *Attorney, Agent, or Firm* — Westerman, Hattori, Daniels & Adrian, LLP

(57) ABSTRACT

A negative resist composition comprising a sulfonium compound having formula (A) and a base polymer is provided. The resist composition exhibits a high resolution during pattern formation and forms a pattern with minimal LER.

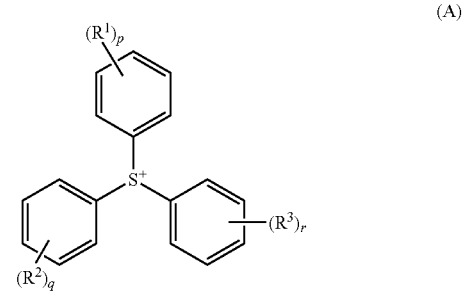

(A)

17 Claims, 3 Drawing Sheets

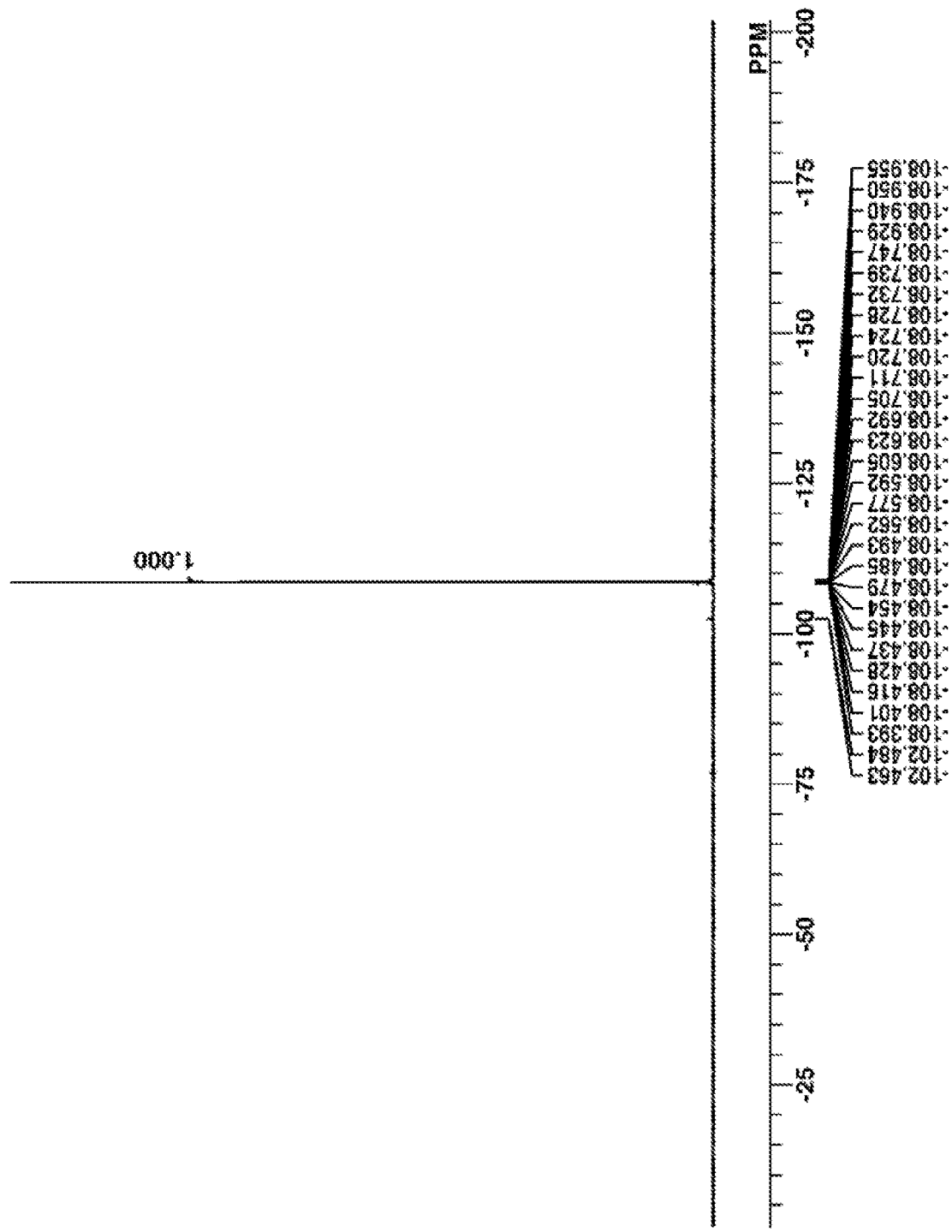

CHEMICALLY AMPLIFIED NEGATIVE RESIST COMPOSITION AND RESIST PATTERN FORMING PROCESS

CROSS-REFERENCE TO RELATED APPLICATION

This non-provisional application claims priority under 35 U.S.C. § 119(a) on Patent Application No. 2016-255025 filed in Japan on Dec. 28, 2016, the entire contents of which are hereby incorporated by reference.

TECHNICAL FIELD

This invention relates to a chemically amplified negative resist composition and a resist pattern forming process using the same.

BACKGROUND ART

To meet the recent demand for higher integration in integrated circuits, pattern formation to a finer feature size is required. Acid-catalyzed chemically amplified resist compositions are most often used in forming resist patterns with a feature size of 0.2 µm or less. High-energy radiation such as UV, deep-UV or EB is used as the light source for exposure of these resist compositions. In particular, while EB lithography is utilized as the ultra-fine microfabrication technique, it is also indispensable in processing a photomask blank to form a photomask for use in semiconductor device fabrication.

Polymers comprising a major proportion of aromatic structure having an acidic side chain, for example, polyhydroxystyrene are useful in resist materials for the KrF excimer laser lithography. These polymers are not used in resist materials for the ArF excimer laser lithography since they exhibit strong absorption at a wavelength of around 200 nm. These polymers, however, are expected to form useful resist materials for the EB and EUV lithography for forming patterns of finer size than the processing limit of ArF excimer laser because they offer high etching resistance.

Resist compositions for photolithography include positive ones in which exposed areas are dissolved away and negative ones in which exposed areas are left as a pattern. A viable composition is selected among them depending on the desired resist pattern. In general, the chemically amplified negative resist composition comprises a polymer which is normally soluble in an aqueous alkaline developer, an acid generator which is decomposed to generate an acid upon exposure to light, and a crosslinker which causes the polymer to crosslink in the presence of the acid serving as a catalyst, thus rendering the polymer insoluble in the developer (sometimes, the crosslinker is incorporated in the polymer). Typically a basic compound is added for controlling the diffusion of the acid generated upon light exposure.

Typical of the alkali-soluble units to constitute polymers which dissolve in aqueous alkaline developer are units derived from phenols. A number of negative resist compositions of such type were developed, especially as adapted for exposure to KrF excimer laser light. These compositions have not been used in the ArF excimer laser lithography because the phenolic units are not transmissive to exposure light having a wavelength of 150 to 220 nm. Recently, these compositions are recognized attractive again as the negative resist composition for the short wavelength (e.g., EB or EUV) lithography capable of forming finer size patterns. Exemplary compositions are described in Patent Documents 1 to 3.

Improvements were made in the control of resist sensitivity and pattern profile by properly selecting and combining components used in resist compositions and adjusting processing conditions. One outstanding problem is the diffusion of acid that has a significant impact on the resolution of a chemically amplified resist composition.

An acid diffusion inhibitor is, in fact, essential for controlling acid diffusion and improving the performance, especially resolution of a resist composition. Studies have been made on the acid diffusion inhibitor while amines and weak acid onium salts have been generally used. The weak acid onium salts are exemplified in several patent documents. Patent Document 4 describes that the addition of triphenylsulfonium acetate ensures to form a satisfactory resist pattern without T-top profile, a difference in line width between isolated and grouped patterns, and standing waves. Patent Document 5 reports improvements in sensitivity, resolution and exposure margin by the addition of sulfonic acid ammonium salts or carboxylic acid ammonium salts. Also, Patent Document 6 describes that a resist composition for KrF or EB lithography comprising a PAG capable of generating a fluorinated carboxylic acid is improved in resolution and process latitude such as exposure margin and depth of focus. Further, Patent Document 7 describes that a resist composition for $F_2$ laser lithography comprising a PAG capable of generating a fluorinated carboxylic acid is improved in line edge roughness (LER) and solves the footing problem. While Patent Documents 4 to 7 refer to the KrF, EB and $F_2$ lithography, Patent Document 8 describes a positive photosensitive composition for ArF excimer laser lithography comprising a carboxylic acid onium salt. These systems are based on the mechanism that a salt exchange occurs between a weak acid onium salt and a strong acid (sulfonic acid) generated by another PAG upon exposure, to form a weak acid and a strong acid onium salt. That is, the strong acid (sulfonic acid) having high acidity is replaced by a weak acid (carboxylic acid), thereby suppressing acid-catalyzed decomposition reaction of acid labile group and reducing or controlling the distance of acid diffusion. The onium salt apparently functions as an acid diffusion inhibitor.

However, when a resist composition comprising the foregoing carboxylic acid onium salt or fluorocarboxylic acid onium salt is used in patterning, LER still remains as an outstanding problem in the recent advanced miniaturization technology. It would be desirable to have an acid diffusion inhibitor capable of minimizing LER.

CITATION LIST

Patent Document 1: JP-A 2006-201532 (US 20060166133, EP 1684118)
Patent Document 2: JP-A 2006-215180
Patent Document 3: JP-A 2008-249762 (U.S. Pat. No. 9,075,306, EP 1975711)
Patent Document 4: JP 3955384 (U.S. Pat. No. 6,479,210)
Patent Document 5: JP-A H11-327143
Patent Document 6: JP 4231622 (U.S. Pat. No. 6,485,883)
Patent Document 7: JP 4116340 (U.S. Pat. No. 7,214,467)
Patent Document 8: JP 4226803 (U.S. Pat. No. 6,492,091)
Patent Document 9: JP 4575479

DISCLOSURE OF INVENTION

An object of the invention is to provide a chemically amplified negative resist composition which is processed by lithography to form a resist pattern with improved resolution and minimal LER, and a pattern forming process using the resist composition.

The inventors have found that a resist composition comprising a specific betaine type compound can be processed by lithography to form a resist pattern with minimal LER.

In one aspect, the invention provides a negative resist composition comprising (A) a sulfonium compound having the formula (A) and (B) a base polymer containing a polymer comprising recurring units having the formula (B1).

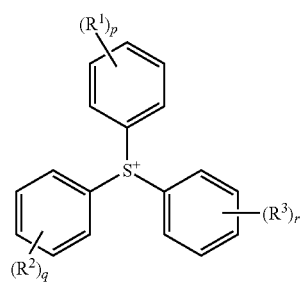

(A)

Herein $R^1$, $R^2$, and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^3$ may bond together to form a ring with the carbon atoms to which they are attached.

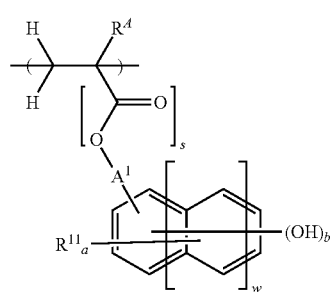

(B1)

Herein $R^A$ is hydrogen, fluorine, methyl or trifluoromethyl, $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, $A^1$ is a single bond or $C_1$-$C_{10}$ straight, branched or cyclic alkylene group in which an ether bond may intervene in a carbon-carbon bond, s is 0 or 1, w is an integer of 0 to 2, a is an integer satisfying 0≤a≤5+2w−b, and b is an integer of 1 to 3.

In a preferred embodiment, the polymer further comprises recurring units of at least one type selected from recurring units having the formulae (B2), (B3) and (B4).

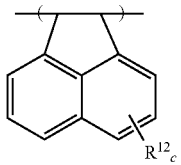

(B2)

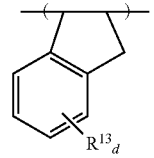

(B3)

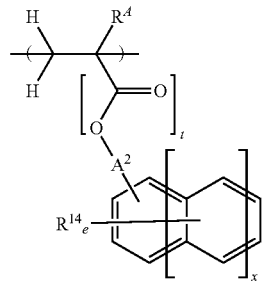

(B4)

Herein $R^A$ is as defined above, $R^{12}$ and $R^{13}$ are each independently hydroxyl, halogen, acetoxy, an optionally halogenated $C_2$-$C_8$ straight, branched or cyclic acyloxy group, optionally halogenated $C_1$-$C_8$ straight, branched or cyclic alkyl group, optionally halogenated $C_1$-$C_8$ straight, branched or cyclic alkoxy group, or optionally halogenated $C_2$-$C_8$ straight, branched or cyclic alkylcarbonyloxy group, $R^{14}$ is an acetyl group, acetoxy group, $C_1$-$C_{20}$ straight, branched or cyclic alkyl group, $C_1$-$C_{20}$ straight, branched or cyclic alkoxy group, $C_2$-$C_{20}$ straight, branched or cyclic acyloxy group, $C_2$-$C_{20}$ straight, branched or cyclic alkoxyalkyl group, $C_2$-$C_{20}$ alkylthioalkyl group, halogen atom, nitro group, cyano group, sulfinyl group, or sulfonyl group, $A^2$ is a single bond or $C_1$-$C_{10}$ straight, branched or cyclic alkylene group in which an ether bond may intervene in a carbon-carbon bond, c and d are each independently an integer of 0 to 4, e is an integer of 0 to 5, x is an integer of 0 to 2, and t is 0 or 1.

In a preferred embodiment, the polymer further comprises recurring units having the formula (B5).

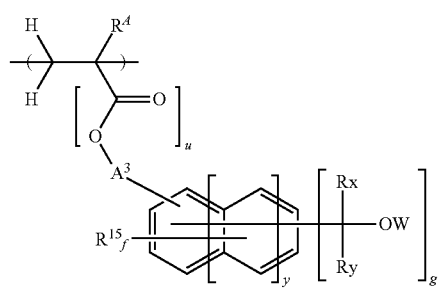

(B5)

Herein $R^A$ is as defined above, $A^3$ is a single bond or $C_1$-$C_{10}$ straight, branched or cyclic alkylene group in which an ether bond may intervene in a carbon-carbon bond, $R^{15}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, W is hydrogen, a $C_1$-$C_{10}$ straight, branched or cyclic monovalent aliphatic hydrocarbon group in which an ether, carbonyl or carbonyloxy moiety may intervene in a carbon-carbon bond, or an optionally substituted monovalent aromatic ring group, Rx and Ry are each independently hydrogen, an optionally hydroxy or alkoxy-substituted $C_1$-$C_{15}$ alkyl group or an optionally substituted monovalent aromatic ring group, with the proviso that both Rx and Ry are not hydrogen at the same time, Rx and Ry may bond together to form a ring with the carbon atom to which they are attached, y is an integer of 0 to 2, u is 0 or 1, f is an integer satisfying $0 \leq f \leq 5+2y-g$, and g is an integer of 1 to 3.

In this embodiment, the polymer may further comprise recurring units of at least one type selected from units having the formulae (a1) to (a6).

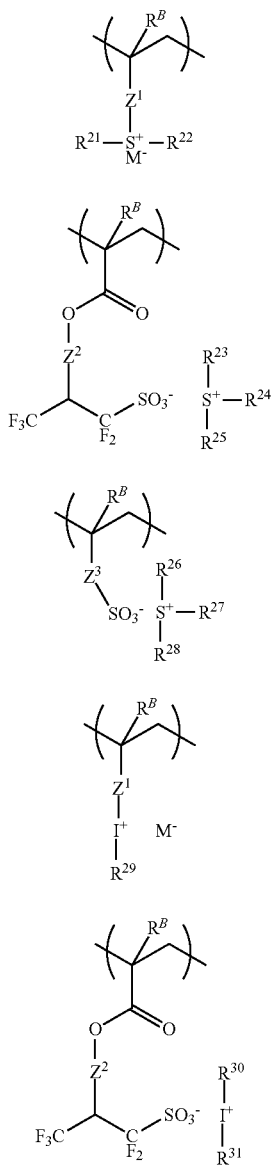

Herein $R^B$ is each independently hydrogen or methyl, $Z^1$ is a single bond, phenylene group, —O—$Z^{12}$—, or —C(=O)—$Z^{11}$-$Z^{12}$—, $Z^{11}$ is —O— or —NH—, $Z^{12}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety, $Z^2$ is a single bond or —$Z^{21}$—C(=O)—O—, $Z^{21}$ is a $C_1$-$C_{20}$ straight, branched or cyclic divalent hydrocarbon group which may contain a heteroatom-containing moiety, $Z^3$ is a single bond, methylene, ethylene, phenylene, fluorinated phenylene, —O—$Z^{32}$—, or —C(=O)—$Z^{31}$-$Z^{32}$—, $Z^{31}$ is —O— or —NH—, $Z^{32}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety, $M^-$ is a non-nucleophilic counter ion, $R^{21}$ to $R^{33}$ are each independently a $C_1$-$C_{20}$ straight, branched or cyclic monovalent hydrocarbon group which may contain a heteroatom-containing moiety, or $R^{21}$ and $R^{22}$ may bond together to form a ring with the sulfur atom to which they are attached, or any two of $R^{23}$, $R^{24}$ and $R^{25}$, or any two of $R^{26}$, $R^{27}$ and $R^{28}$ may bond together to form a ring with the sulfur atom to which they are attached.

More preferably, the polymer comprises recurring units having the formula (B1-1), recurring units having the formula (B5-1), and recurring units having the formula (a2) or (a5):

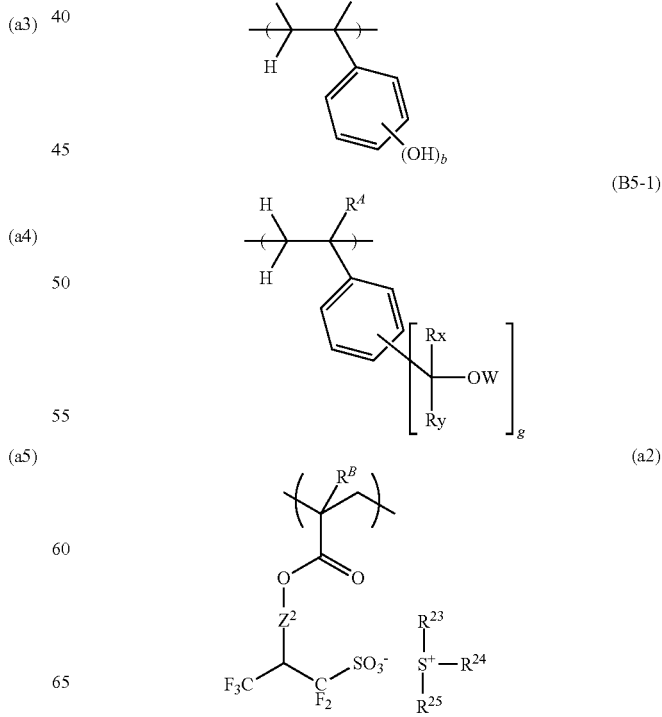

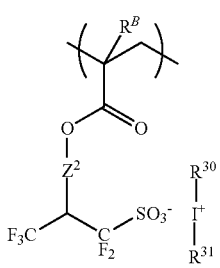

(a5)

wherein $R^A$, $R^B$, $Z^2$, $R^{23}$, $R^{24}$, $R^{25}$, $R^{30}$, $R^{31}$, Rx, Ry, W, b, and g are as defined above.

In a preferred embodiment, the base polymer (B) further contains a polymer comprising recurring units having the formula (B1) and recurring units having the formula (B5), being free of recurring units having the formulae (a1) to (a6).

In one preferred embodiment, the negative resist composition may further comprise (C) a crosslinker. In another embodiment, the negative resist composition is free of a crosslinker.

In a preferred embodiment, the negative resist composition may further comprise (D) a fluorinated polymer comprising recurring units having the formula (D1), and recurring units of at least one type selected from units having the formulae (D2), (D3), (D4) and (D5).

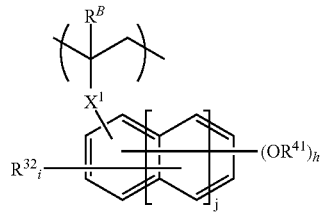

(D1)

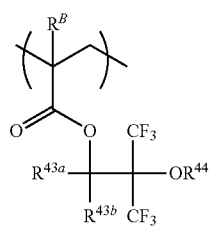

(D2)

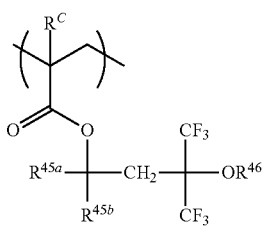

(D3)

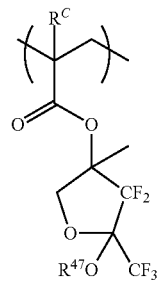

(D4)

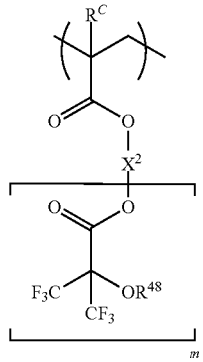

(D5)

Herein $R^B$ is each independently hydrogen or methyl, $R^C$ is each independently hydrogen, fluorine, methyl or trifluoromethyl, $R^{41}$ is hydrogen or a $C_1$-$C_5$ straight or branched monovalent hydrocarbon group in which a heteroatom may intervene in a carbon-carbon bond, $R^{42}$ is a $C_1$-$C_5$ straight or branched monovalent hydrocarbon group in which a heteroatom may intervene in a carbon-carbon bond, $R^{43a}$, $R^{43b}$, $R^{45a}$ and $R^{45b}$ are each independently hydrogen or a $C_1$-$C_{10}$ straight, branched or cyclic alkyl group, $R^{44}$, $R^{46}$, $R^{47}$ and $R^{48}$ are each independently hydrogen, a $C_1$-$C_{15}$ straight, branched or cyclic monovalent hydrocarbon group or monovalent fluorinated hydrocarbon group, or an acid labile group, with the proviso that an ether or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$, h is an integer of 1 to 3, i is an integer satisfying: $0 \leq i \leq 5+2j-h$, j is 0 or 1, m is an integer of 1 to 3, $X^1$ is a single bond, —C(=O)—O— or —C(=O)—NH—, and $X^2$ is a $C_1$-$C_{20}$ straight, branched or cyclic (m+1)-valent hydrocarbon group or fluorinated hydrocarbon group.

The negative resist composition may further comprise (E) an acid generator.

In another aspect, the invention provides a resist pattern forming process comprising the steps of applying the negative resist composition defined above onto a processable substrate to form a resist film thereon, exposing the resist film patternwise to high-energy radiation, and developing the resist film in an alkaline developer to form a resist pattern.

Typically, the high-energy radiation is KrF excimer laser, EUV or EB.

Preferably the processable substrate is a photomask blank.

Advantageous Effects of Invention

Owing to the sulfonium compound, the negative resist composition of the invention is effective for controlling acid diffusion during the exposure step. When the composition is coated as a resist film and processed to form a pattern, the resist film exhibits a very high resolution during pattern formation, and forms a pattern with minimal LER and minimal line width variation relative to dose changes and pattern layout dependency. Owing to the recurring units of formula (B1), the adhesion of the resist film to a processable substrate is improved, and the solubility of the resist film in alkaline developer is controlled.

The pattern forming process using the negative resist composition can form a resist pattern with minimal LER while maintaining a high resolution. The invention is best suited for a micropatterning process, typically KrF, EUV or EB lithography.

BRIEF DESCRIPTION OF DRAWINGS

FIG. 3 is a diagram showing 19F-NMR spectrum of Compound Q-2 in Example 1-2.

DESCRIPTION OF EMBODIMENTS

Figure 1:
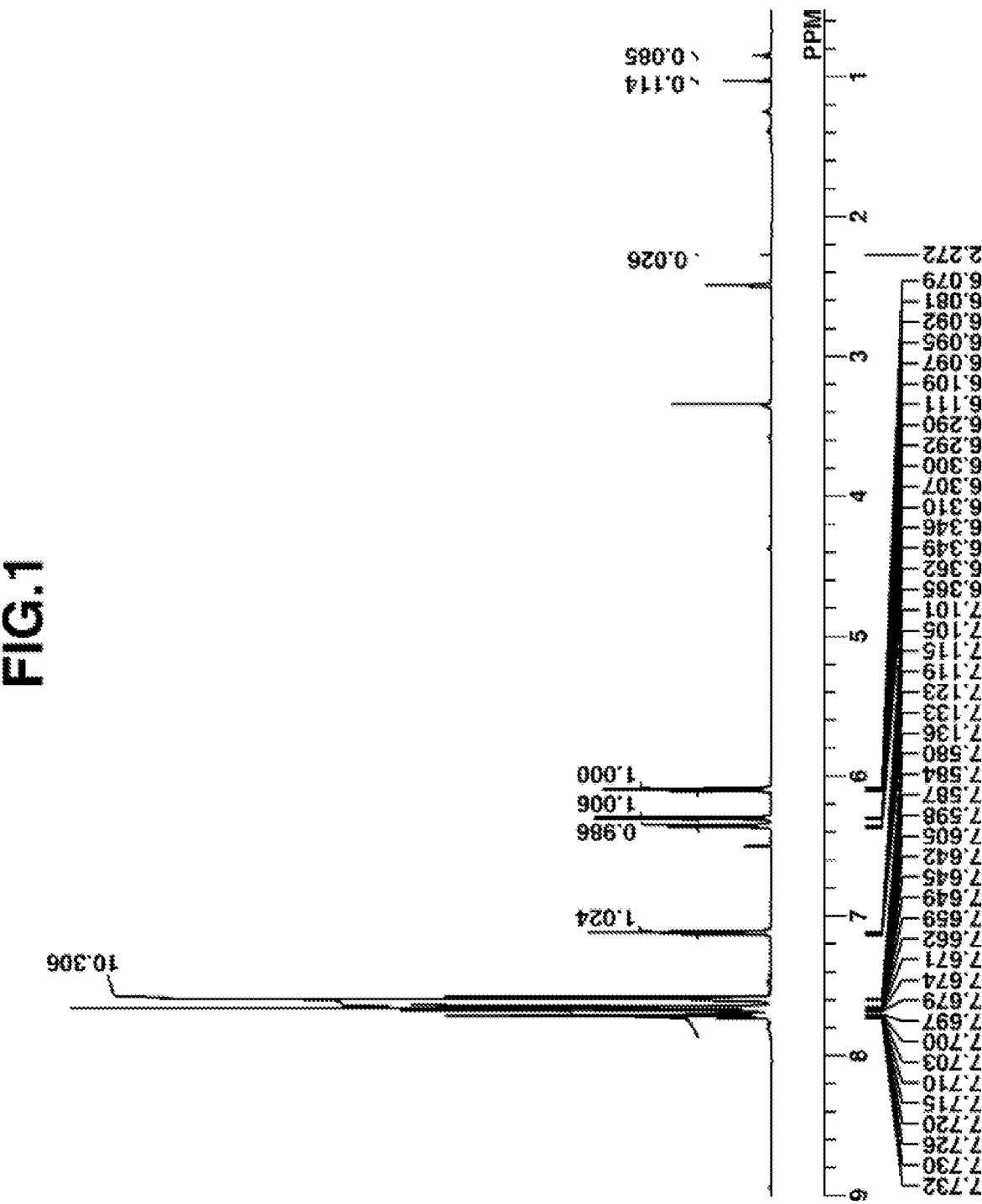
FIG. 1 is a diagram showing $^1$H-NMR spectrum of Compound Q-1 in Example 1-1.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, Me stands for methyl, Ac stands for acetyl, and the broken line designates a valence bond.

The abbreviations and acronyms have the following meaning.

EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LER: line edge roughness
CDU: critical dimension uniformity It is understood that for some structures represented by chemical formulae, there can exist enantiomers and diastereomers because of the presence of asymmetric carbon atoms. In such a case, a single formula collectively represents all such isomers. The isomers may be used alone or in admixture.

Negative Resist Composition

The negative resist composition of the invention is defined as comprising (A) a sulfonium compound and (B) a base polymer.

(A) Sulfonium Compound

Component (A) is a sulfonium compound having the formula (A).

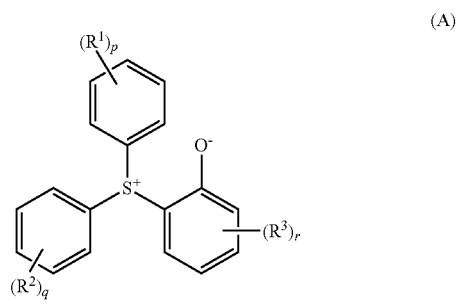

(A)

In formula (A), $R^1$, $R^2$ and $R^3$ are each independently a $C_1$-$C_{20}$ straight, branched or cyclic monovalent hydrocarbon group which may contain a heteroatom. Examples of the monovalent hydrocarbon group include alkyl groups such as methyl, ethyl, propyl, isopropyl, n-butyl, sec-butyl, t-butyl, n-pentyl, t-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl, and aryl groups such as phenyl, naphthyl, and anthracenyl. In these hydrocarbon groups, one or more hydrogen may be replaced by a moiety containing a heteroatom such as oxygen, sulfur, nitrogen or halogen, or a moiety containing a heteroatom such as oxygen, sulfur or nitrogen may intervene between carbon atoms, so that the group may contain a hydroxy moiety, cyano moiety, carbonyl moiety, ether bond, thioether bond, ester bond, sulfonic acid ester bond, carbonate bond, carbamate bond, lactone ring, sultone ring, carboxylic anhydride or haloalkyl moiety.

In formula (A), p and q are each independently an integer of 0 to 5, and r is an integer of 0 to 4. Each of p, q and r is preferably 0, 1 or 2 for ease of synthesis and availability of reactants.

When p is 2 to 5, two adjoining groups $R^1$ may bond together to form a ring with the carbon atoms to which they are attached. When q is 2 to 5, two adjoining groups $R^2$ may bond together to form a ring with the carbon atoms to which they are attached. When r is 2 to 4, two adjoining groups $R^3$ may bond together to form a ring with the carbon atoms to which they are attached.

Examples of the sulfonium compound having formula (A) are given below, but not limited thereto.

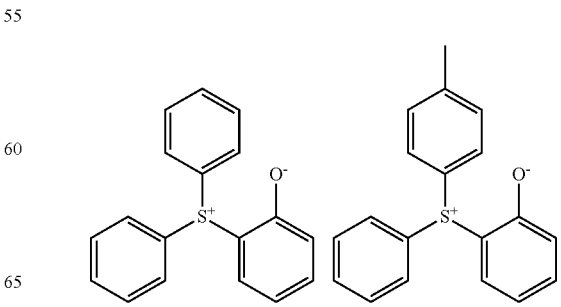

-continued
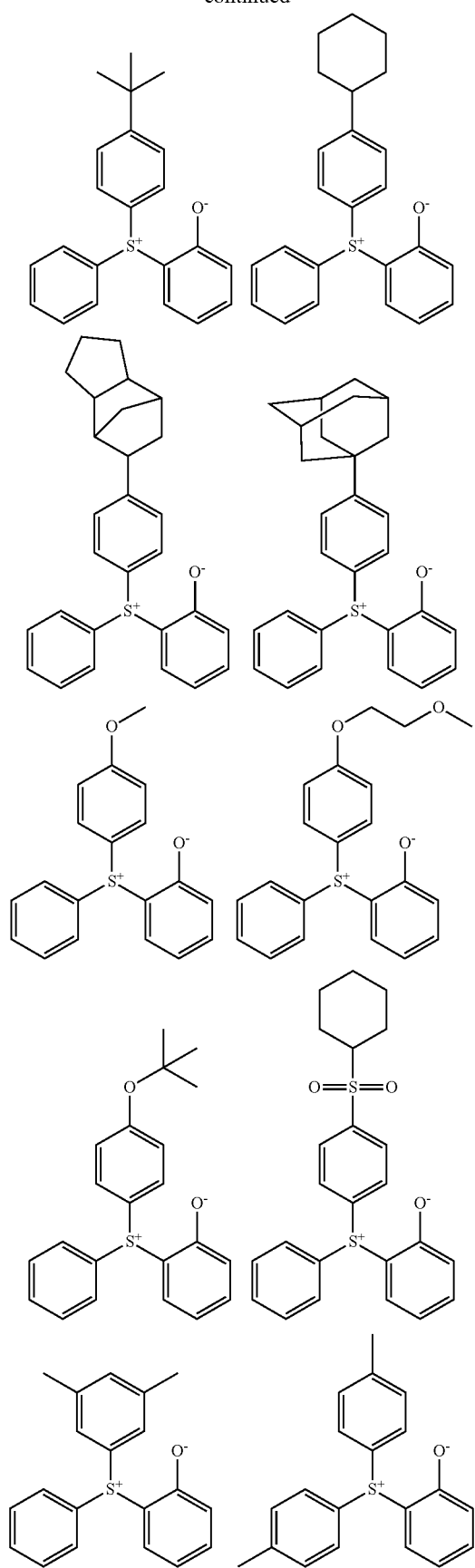
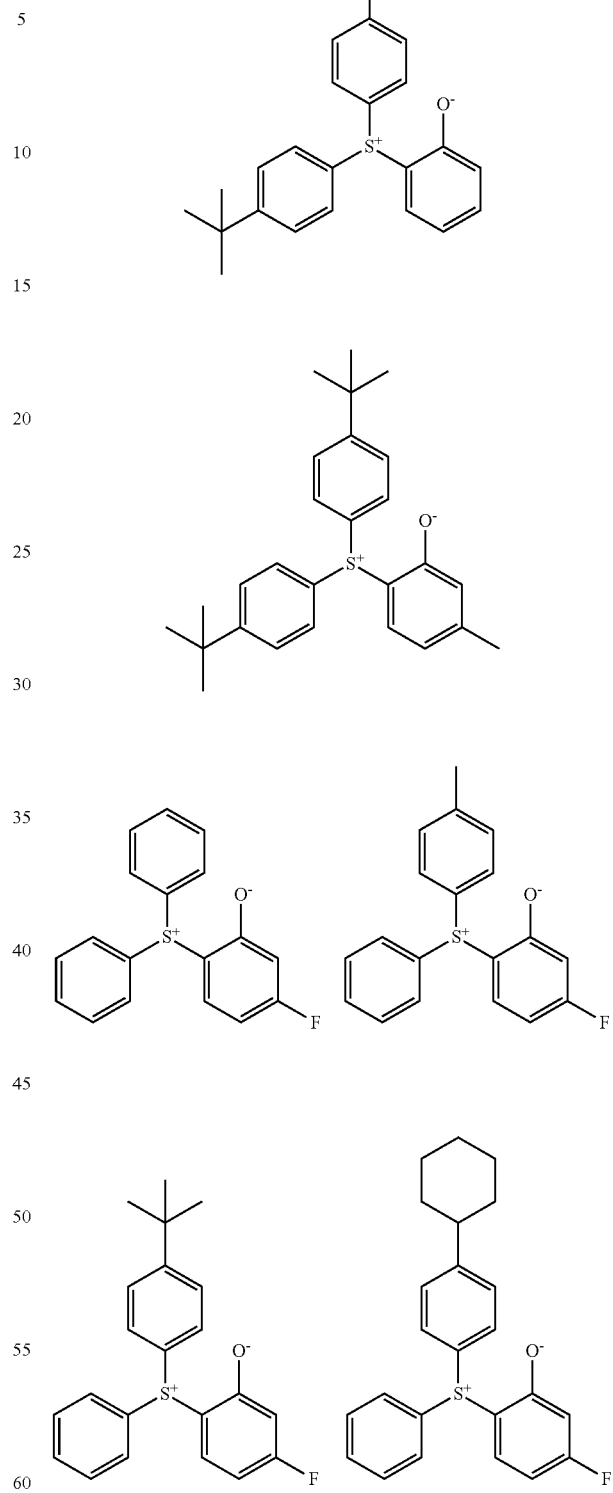
The sulfonium compound having formula (A) may be synthesized by a combination of well-known organic chemistry methods, for example, according to the scheme shown below.

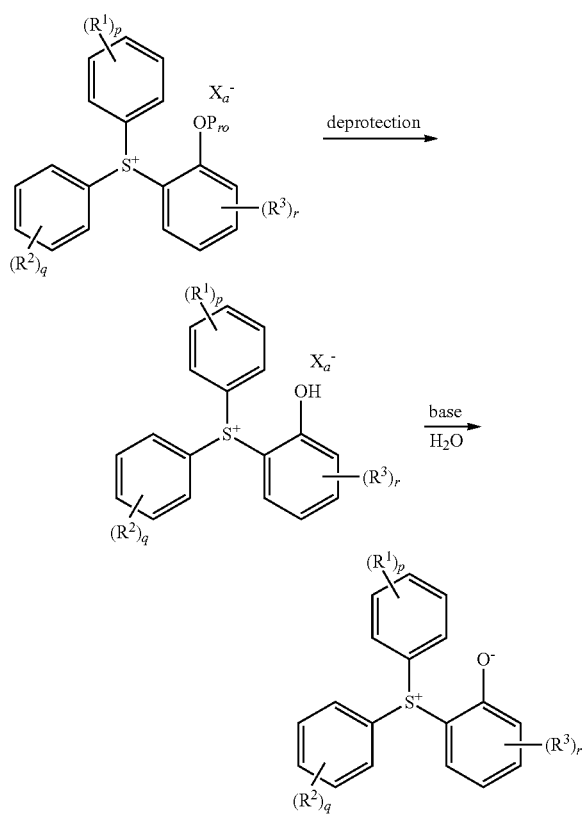

Herein $R^1$, $R^2$, $R^3$, p, q and r are as defined above, $X_a^-$ is an anion, and $P_{ro}$ is a protective group.

There is first furnished a sulfonium salt having a sulfonium cation in which the carbon atom at α-position relative to the sulfur atom has a protected hydroxyl group substituted thereon. The protective group ($P_{ro}$) for a hydroxyl group is not particularly limited and may be any of protective groups commonly used in organic synthesis, for example, tert-butyl and methoxymethyl. The thus furnished sulfonium salt is subjected to deprotection reaction of the hydroxyl group, then treatment with a base, and separatory extraction with an organic solvent-water system, whereby the inventive sulfonium compound is extracted in the organic layer. Suitable bases used herein include sodium hydroxide and tetramethylammonium hydroxide, but are not limited thereto.

The sulfonium compound defined herein functions quite effectively as an acid diffusion inhibitor or regulator when applied to a resist composition. As used herein, the term "acid diffusion inhibitor" is a compound which traps the acid generated by the PAG in the resist composition in the exposed region to prevent the acid from diffusing into the unexposed region for thereby forming the desired pattern.

The inventive sulfonium compound follows an acid diffusion controlling mechanism which is described below. The acid generated by the PAG in the resist composition in the exposed region should have a strong acidity enough to deprotect the acid labile group on the base resin. For example, sulfonic acid which is fluorinated at α-position relative to sulfo group and sulfonic acid which is not fluorinated are generally used in the EB lithography. In a resist composition system where the PAG and the inventive sulfonium compound co-exist, the acid generated by the PAG is trapped by the inventive sulfonium compound (acid diffusion inhibitor), and instead, the sulfonium compound is converted from betaine structure to sulfonium salt. Another mechanism that the inventive sulfonium compound itself is photo-decomposed is contemplated. In this case, a weakly acidic phenolic compound is generated from decomposition, which has an insufficient acidity to deprotect the acid labile group on the base resin. In either case, the inventive sulfonium compound functions as a strong acid diffusion inhibitor.

The acid diffusion inhibitor, which may also be referred to as an onium salt type quencher, tends to form a resist pattern with a reduced LER as compared with the conventional quenchers in the form of amine compounds. This is presumably because salt exchange between strong acid and the inventive sulfonium compound is infinitely repeated. The site where strong acid is generated at the end of exposure shifts from the site where the onium salt of strong acid generation type is initially present. It is believed that since the cycle of photo-acid generation and salt exchange is repeated many times, the acid generation point is averaged, and this smoothing effect acts to reduce the LER of a resist pattern after development.

As the compound that exerts a quencher effect via the same mechanism, Patent Document 8 and JP-A 2003-005376 report carboxylic acid onium salts, alkanesulfonic acid onium salts, and arylsulfonic acid onium salts as the acid diffusion inhibitor. On use of an alkanesulfonic acid onium salt or arylsulfonic acid onium salt, the generated acid has such an acid strength that part thereof in the highly exposed region may induce deprotection reaction of the acid labile group on the base resin, leading to an increase of acid diffusion, which invite degradation of resist performance factors like resolution and CDU. Also in the case of carboxylic acid onium salt, the generated carboxylic acid has a weak acidity and is not reactive with the acid labile group on the base resin. Thus the carboxylic acid onium salt achieves some improvement as acid diffusion inhibitor, but fails to satisfy an overall balance of resolution, LER and CDU in a more miniaturized region.

In contrast, the inventive sulfonium compound achieves substantial improvements in resist performance, which are not achievable with the above-mentioned acid diffusion inhibitors. Although the reason is not clearly understood, the following reason is presumed. The inventive sulfonium compound is characterized by a betaine structure possessing a sulfonium cation and a phenoxide anion within a common molecule, and the phenoxide moiety at the ortho position relative to $S^+$. It is presumed that because of the location of phenoxide or anion in the vicinity of $S^+$, the inventive sulfonium compound assumes a hypervalent structure, in which $S^+$ and the phenoxide moiety are nearly in a three-center four-electron bond having a shorter bond distance than the ordinary ionic bond, that is, a covalent bond. Due to this structural specificity, the sulfonium phenoxide which is typically unstable remains stable. It is further presumed that since the inventive sulfonium compound is weakened in ionic bond nature as mentioned above, it is improved in organic solvent solubility and hence, more uniformly dispersed in the resist composition, leading to improvements in LER and CDU.

Although the conventional salt type quencher undergoes equilibration reaction in trapping the acid generated by the PAG and is thus inferior in acid diffusion control as alluded to previously, the reaction of the inventive sulfonium compound is irreversible. This is accounted for by the driving force that the sulfonium compound is converted from the betaine structure to a stabler salt type structure by trapping the acid. In addition, the inventive sulfonium compound has a counter anion in the form of strongly basic phenoxide. For these reasons, the inventive sulfonium compound has a very high acid diffusion controlling ability. Since the contrast is thus improved, there is provided a resist composition which is also improved in resolution and collapse resistance.

In general, a sulfonium salt of weak acid is low soluble in organic solvents because of originally an ionic compound, and becomes substantially insoluble in organic solvents if it takes a betaine structure. Since the low solubility sulfonium salt is awkward to uniformly disperse in a resist composition, it can cause degradation of LER and defect generation. In contrast, the inventive sulfonium compound has superior solvent solubility. Although the reason is not well understood, it is presumed that the structural specificity of the inventive sulfonium compound that the phenoxide moiety is at the ortho position relative to $S^+$ participates in solubility. Due to this positional relationship, the inventive sulfonium compound assumes a hypervalent structure, and $S^+$ and phenoxide moiety are nearly in a three-center, four-electron bond having a shorter bond distance than the ordinary ionic bond, that is, a covalent bond, by which organic solvent solubility is increased. As a result, the inventive sulfonium compound is uniformly dispersed in the resist composition, which is one of factors accounting for improved LER and CDU.

An appropriate amount of the sulfonium compound (A) is 0.1 to 50 parts, more preferably 1 to 30 parts by weight per 100 parts by weight of the base polymer (B). As long as its amount is in the range, the sulfonium compound fully functions as an acid diffusion inhibitor, eliminating any performance problems such as sensitivity drop, solubility shortage, and foreign particles. The sulfonium compound (A) may be used alone or in admixture of two or more.

(B) Base Polymer

The negative resist composition also comprises (B) a base polymer containing a polymer comprising recurring units having the formula (B1). It is noted that the recurring unit having formula (B1) is simply referred to as recurring unit (B1), and the polymer is referred to as polymer (B). The recurring units (B1) are effective for imparting etching resistance, adhesion to substrates, and solubility in alkaline developer.

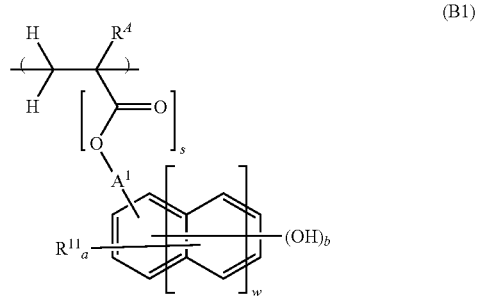

(B1)

In formula (B1), $R^A$ is hydrogen, fluorine, methyl or trifluoromethyl. $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group. $A^1$ is a single bond or a $C_1$-$C_{10}$ straight, branched or cyclic alkylene group in which an ether bond may intervene in a carbon-carbon bond, s is 0 or 1, w is an integer of 0 to 2, a is an integer in the range: $0 \leq a \leq 5+2w-b$, and b is an integer of 1 to 3.

Examples of the alkylene group represented by $A^1$ include methylene, ethylene, propylene, butylene, pentylene, hexylene, and structural isomers of a carbon skeleton having branched or cyclic structure. For the alkylene group containing an ether bond, in case s=1 in formula (B1), the ether bond may be incorporated at any position excluding the position between the α- and β-carbons relative to the ester oxygen. In case s=0, the atom in $A^1$ that bonds with the main chain becomes an ethereal oxygen atom, and a second ether bond may be incorporated at any position excluding the position between the α- and β-carbons relative to that ether bond. Alkylene groups having no more than 10 carbon atoms are desirable because of a sufficient solubility in alkaline developer.

Preferred examples of the hydrocarbon portion in the acyloxy, alkyl and alkoxy groups represented by $R^{11}$ include methyl, ethyl, propyl, isopropyl, butyl, pentyl, hexyl and structural isomers of a carbon skeleton having branched or cyclic structure. As long as the carbon count is within the upper limit, good solubility in alkaline developer is available.

In formula (B1), w is an integer of 0 to 2. The corresponding structure represents a benzene skeleton when w=0, a naphthalene skeleton when w=1, and an anthracene skeleton when w=2. The subscript a is an integer in the range: $0 \leq a \leq 5+2w-b$. In case w=0, preferably a is an integer of 0 to 3, and b is an integer of 1 to 3. In case w=1 or 2, preferably a is an integer of 0 to 4, and b is an integer of 1 to 3.

The recurring units (B1) are incorporated in an amount of preferably at least 40 mol %, more preferably at least 50 mol % and up to 100 mol %, preferably up to 85 mol %, based on the entire recurring units of the polymer in order to acquire a high resolution in that a high contrast is established between the region to be exposed to high-energy radiation and to be turned negative and the region not to be exposed and not to be turned negative.

Preferred examples of the recurring units (B1) wherein s=0 and $A^1$ is a single bond (meaning that the aromatic ring is directly bonded to the main chain of the polymer), that is, linker-free recurring units include units derived from 3-hydroxystyrene, 4-hydroxystyrene, 5-hydroxy-2-vinylnaphthalene, and 6-hydroxy-2-vinylnaphthalene. More preferred are recurring units represented by the following formula (B1-1). Herein $R^A$ and b are as defined above.

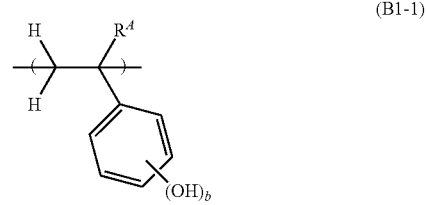

(B1-1)

Preferred examples of the recurring units (B1) wherein s=1, that is, having an ester structure as the linker are shown below, but not limited thereto.

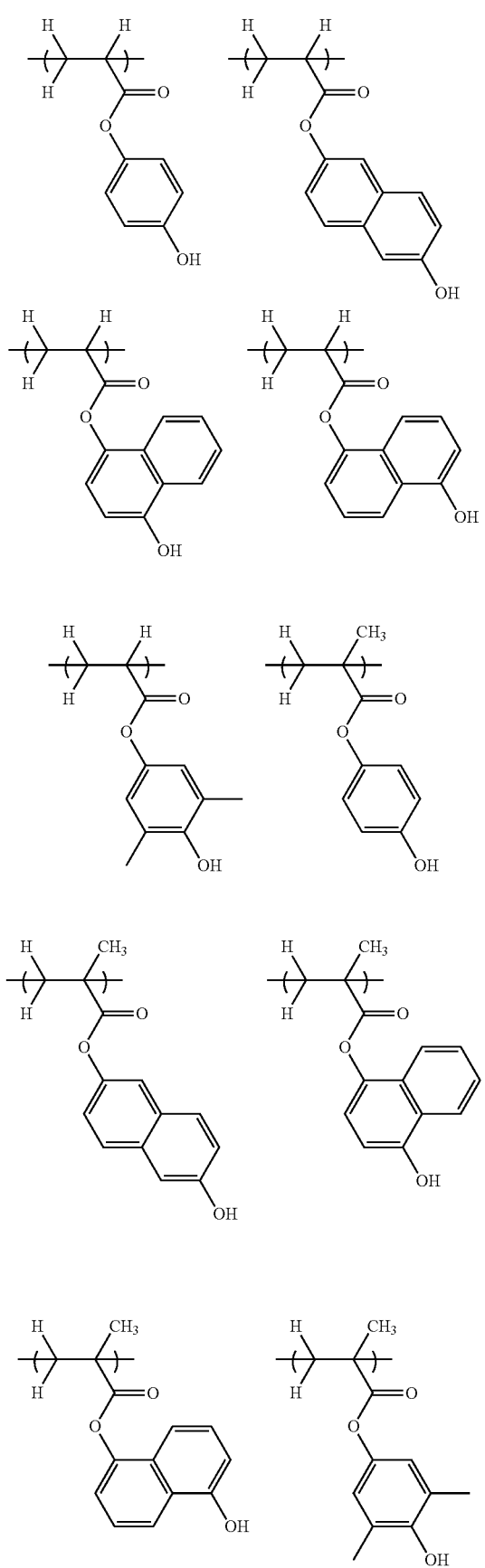
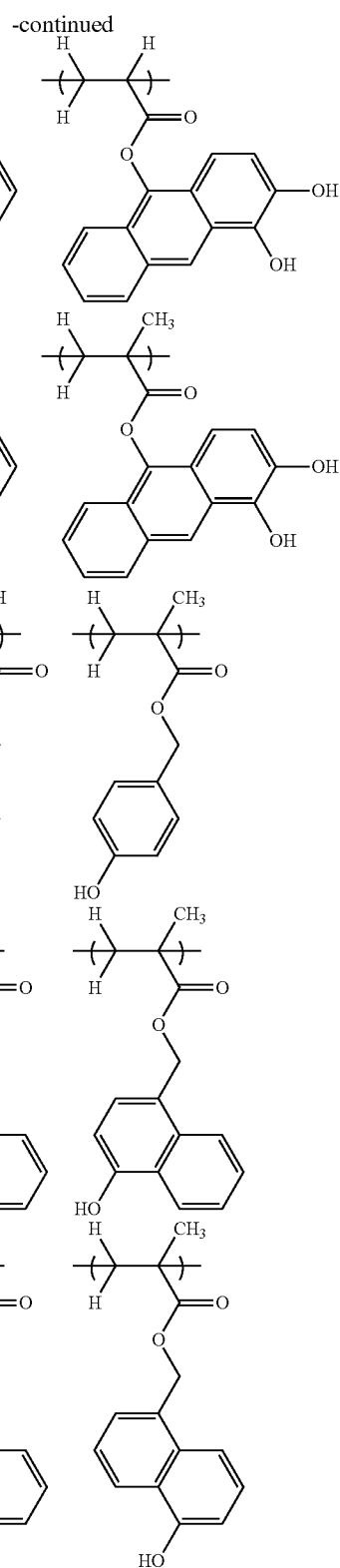
For the purpose of improving etch resistance, preferably the polymer (B) further comprises recurring units of at least one type selected from recurring units having the formula (B2), recurring units having the formula (B3) and recurring units having the formula (B4). Notably these units are simply referred to as recurring units (B2), (B3) and (B4).

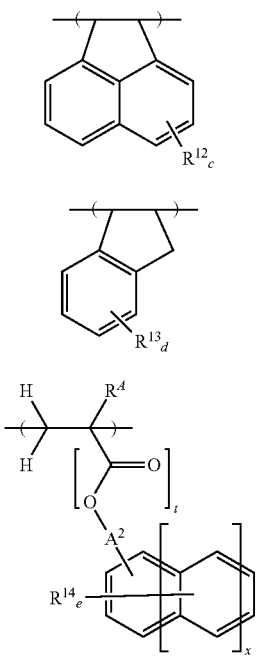

(B2)

(B3)

(B4)

Herein $R^A$ is as defined above. $R^{12}$ and $R^{13}$ are each independently a hydroxyl group, halogen atom, acetoxy group, optionally halogenated $C_2$-$C_8$ straight, branched or cyclic acyloxy group, optionally halogenated $C_1$-$C_8$ straight, branched or cyclic alkyl group, optionally halogenated $C_1$-$C_8$ straight, branched or cyclic alkoxy group, or optionally halogenated $C_2$-$C_8$ straight, branched or cyclic alkylcarbonyloxy group. $R^{14}$ is an acetyl group, acetoxy group, $C_1$-$C_{20}$ straight, branched or cyclic alkyl group, $C_1$-$C_{20}$ straight, branched or cyclic alkoxy group, $C_2$-$C_{20}$ straight, branched or cyclic acyloxy group, $C_2$-$C_{20}$ straight, branched or cyclic alkoxyalkyl group, $C_2$-$C_{20}$ alkylthioalkyl group, halogen atom, nitro group, cyano group, sulfinyl group, or sulfonyl group. $A^2$ is a single bond or $C_1$-$C_{10}$ straight, branched or cyclic alkylene group in which an ether bond may intervene in a carbon-carbon bond, c and d are each independently an integer of 0 to 4, e is an integer of 0 to 5, x is an integer of 0 to 2, and t is 0 or 1.

Preferred examples of the alkylene group represented by $A^2$ include methylene, ethylene, propylene, butylene, pentylene, hexylene and structural isomers of a carbon skeleton having branched or cyclic structure. For the alkylene group containing an ether bond, in case t=1 in formula (B4), the ether bond may be incorporated at any position excluding the position between the α- and β-carbons relative to the ester oxygen. In case t=0 in formula (B4), the atom in $A^2$ that bonds with the main chain becomes an ethereal oxygen atom, and a second ether bond may be incorporated at any position excluding the position between the α- and β-carbons relative to that ether bond. Alkylene groups having no more than 10 carbon atoms are desirable because of a high solubility in alkaline developer.

Preferred examples of the group $R^{14}$ include halogen atoms such as chlorine, bromine and iodine, alkyl groups such as methyl, ethyl, propyl, butyl, pentyl, hexyl and structural isomers thereof, cyclopentyl, cyclohexyl, methoxy, ethoxy, propoxy, butoxy, pentyloxy, hexyloxy and structural isomers of its hydrocarbon moiety, cyclopentyloxy, and cyclohexyloxy. Inter alia, methoxy and ethoxy are useful. An acyloxy group may be readily introduced into a polymer even after polymerization, by a chemical modification method and is advantageously utilized for fine adjustment of the solubility of the base polymer in alkaline developer. Preferred acyloxy groups include methylcarbonyloxy, ethylcarbonyloxy, propylcarbonyloxy, butylcarbonyloxy, pentylcarbonyloxy, hexylcarbonyloxy and structural isomers thereof, cyclopentylcarbonyloxy, cyclohexylcarbonyloxy, and benzoyloxy. As long as the carbon count is equal to or less than 20, an appropriate effect of controlling or adjusting (typically reducing) the solubility of the polymer in alkaline developer is obtainable, and the generation of scum or development defects may be suppressed. Of the foregoing preferred substituent groups, such substituent groups as chlorine, bromine, iodine, methyl, ethyl and methoxy are useful because corresponding monomers may be readily prepared.

In formula (B4), x is an integer of 0 to 2. The corresponding structure represents a benzene skeleton when x=0, a naphthalene skeleton when x=1, and an anthracene skeleton when x=2. In case x=0, preferably e is an integer of 0 to 3; in case x=1 or 2, preferably e is an integer of 0 to 4.

Preferred examples of the recurring units (B4) wherein t is 0 and $A^2$ is a single bond (meaning that the aromatic ring is directly bonded to the main chain of the polymer), that is, linker-free recurring units include units derived from styrene, 4-chlorostyrene, 4-bromostyrene, 4-methylstyrene, 4-methoxystyrene, 4-acetoxystyrene, 2-hydroxypropylstyrene, 2-vinylnaphthalene, and 3-vinylnaphthalene.

Preferred examples of the recurring units (B4) wherein t is 1, that is, having an ester structure as the linker are shown below, but not limited thereto.

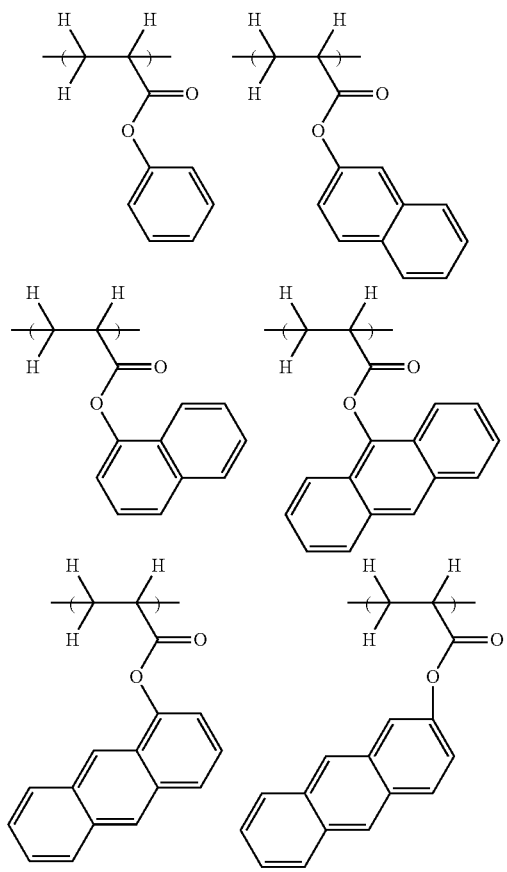

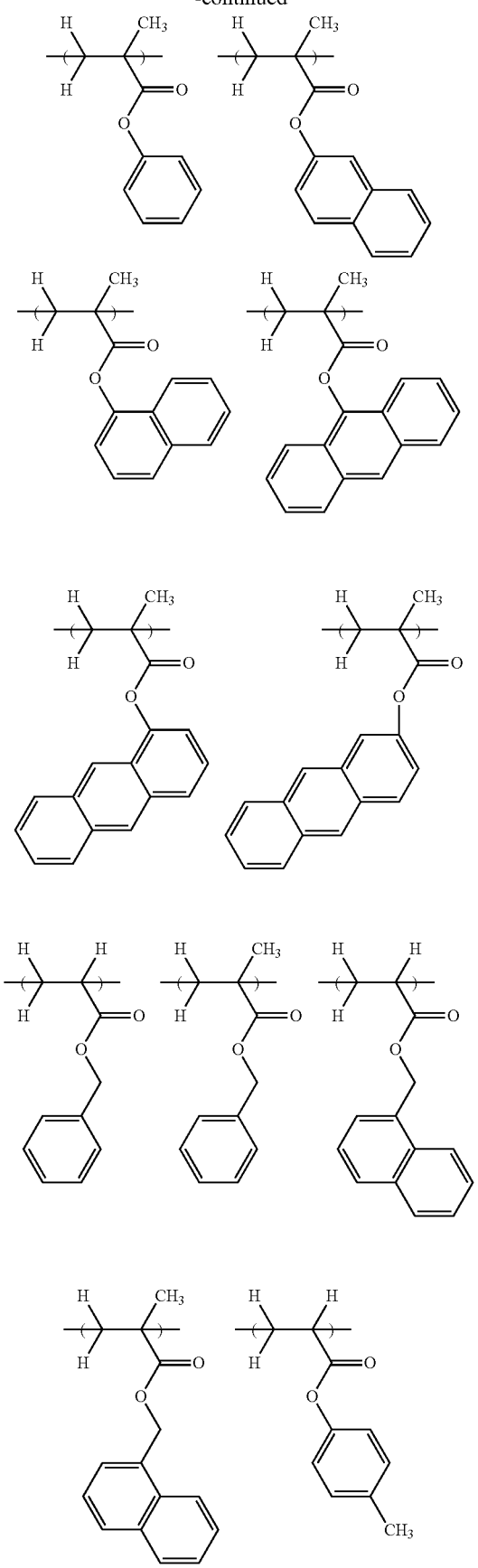

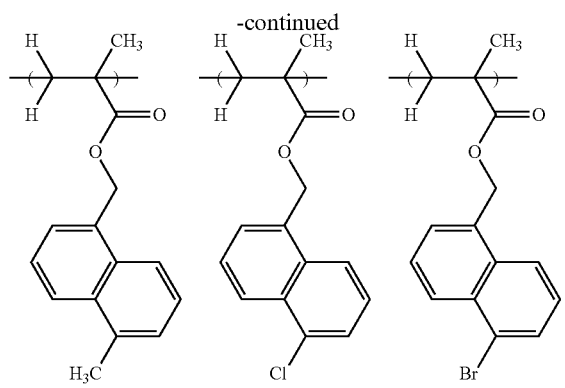

When recurring units of at least one type selected from recurring units (B2) to (B4) are incorporated, better performance is obtained because not only the aromatic ring possesses etching resistance, but the cyclic structure incorporated into the main chain also exerts the effect of improving resistance to EB irradiation during etching and pattern inspection steps.

The recurring units (B2) to (B4) may be of one type or a combination of plural types. The units (B2) to (B4) are preferably incorporated in a range of at least 2 mol %, more preferably at least 5 mol % and up to 35 mol %, more preferably up to 20 mol %, based on the overall recurring units of the polymer in order to exert an effect of improving etching resistance.

Also the polymer (B) may further comprise recurring units having the formula (B5). Notably the recurring units having formula (B5) are simply referred to as recurring units (B5), and of the polymers (B), a polymer further comprising recurring units (B5) is referred to as polymer (B').

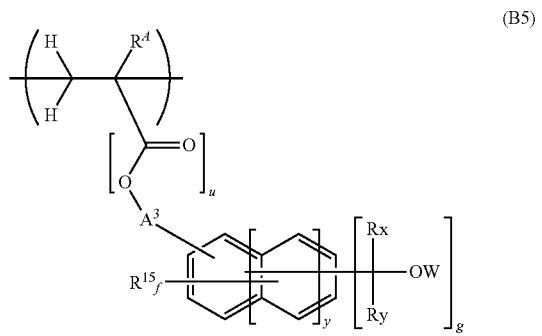

Herein $R^A$ is as defined above. $A^3$ is a single bond or $C_1$-$C_{10}$ straight, branched or cyclic alkylene group in which an ether bond may intervene in a carbon-carbon bond. $R^{15}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group. W is hydrogen, a $C_1$-$C_{10}$ straight, branched or cyclic monovalent aliphatic hydrocarbon group in which an ether, carbonyl or carbonyloxy moiety may intervene in a carbon-carbon bond, or an optionally substituted monovalent aromatic group. Rx and Ry are each independently hydrogen, a $C_1$-$C_{15}$ alkyl group which may be substituted with a hydroxy or alkoxy moiety, or an optionally substituted monovalent aromatic group, Rx and Ry may bond together to form a ring with the carbon atom to which they are attached, excluding that Rx and Ry are hydrogen at the same time, y is an integer of 0 to 2, u is 0 or 1, f is an integer in the range: 0≤f≤5+2y−g, and g is an integer of 1 to 3.

Upon exposure to high-energy radiation, the unit (B5) functions such that the acid-eliminatable group undergoes elimination reaction under the action of an acid which is generated by the acid generator. That is, the unit (B5) induces alkali insolubilization and crosslinking reaction between polymer molecules. Since the unit (B5) permits for more efficient progress of negative-working reaction, it is effective for improving the resolving performance.

Examples of the monovalent aliphatic hydrocarbon and monovalent aromatic groups represented by W include methyl, ethyl, propyl, isopropyl, cyclopentyl, cyclohexyl, adamantyl, methylcarbonyl and phenyl.

Preferred structures of Rx and Ry include methyl, ethyl, propyl, butyl and structural isomers thereof, and substituted forms of the foregoing in which at least one hydrogen is substituted by hydroxy or alkoxy.

The subscript y is an integer of 0 to 2. The structure represents a benzene ring when y=0, a naphthalene ring when y=1, and an anthracene ring when y=2.

Preferred examples of the alkylene group represented by $A^3$ include methylene, ethylene, propylene, butylene, pentylene, hexylene and structural isomers of a carbon skeleton having branched or cyclic structure. For the alkylene group containing an ether bond, in case u=1 in formula (B5), the ether bond may be incorporated at any position excluding the position between the α- and β-carbons relative to the ester oxygen. In case u=0, the atom in $A^3$ that bonds with the main chain becomes an ethereal oxygen atom, and a second ether bond may be incorporated at any position excluding the position between the α- and β-carbons relative to that ether bond.

Preferred examples of the recurring unit (B5) are recurring units of the formula (B5-1).

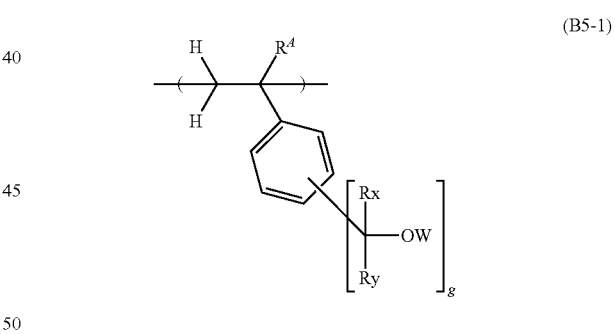

Herein $R^A$, Rx, Ry, W and g are as defined above.

Preferred examples of the recurring unit (B5) are given below, but not limited thereto.

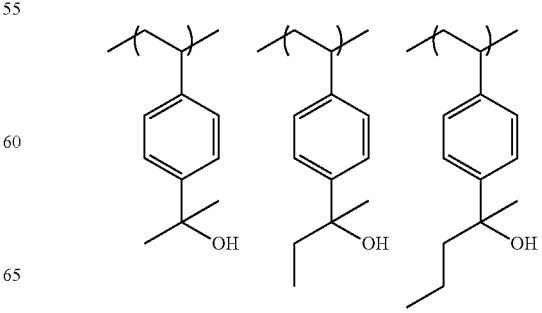

25
-continued
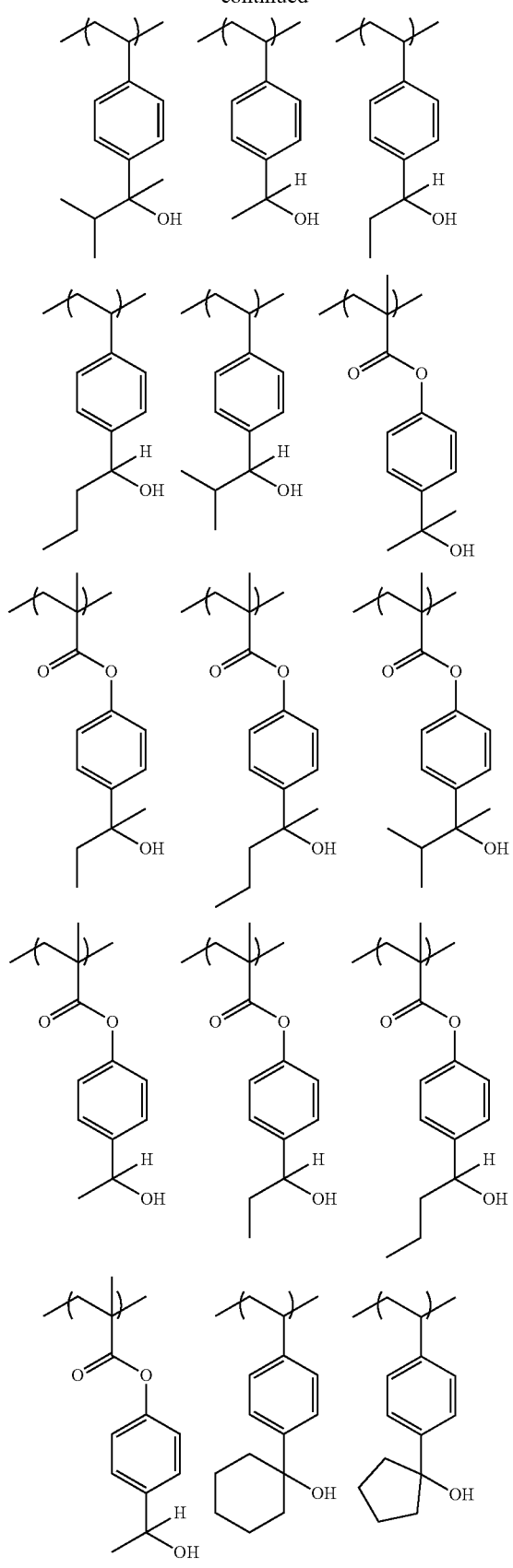
26
-continued
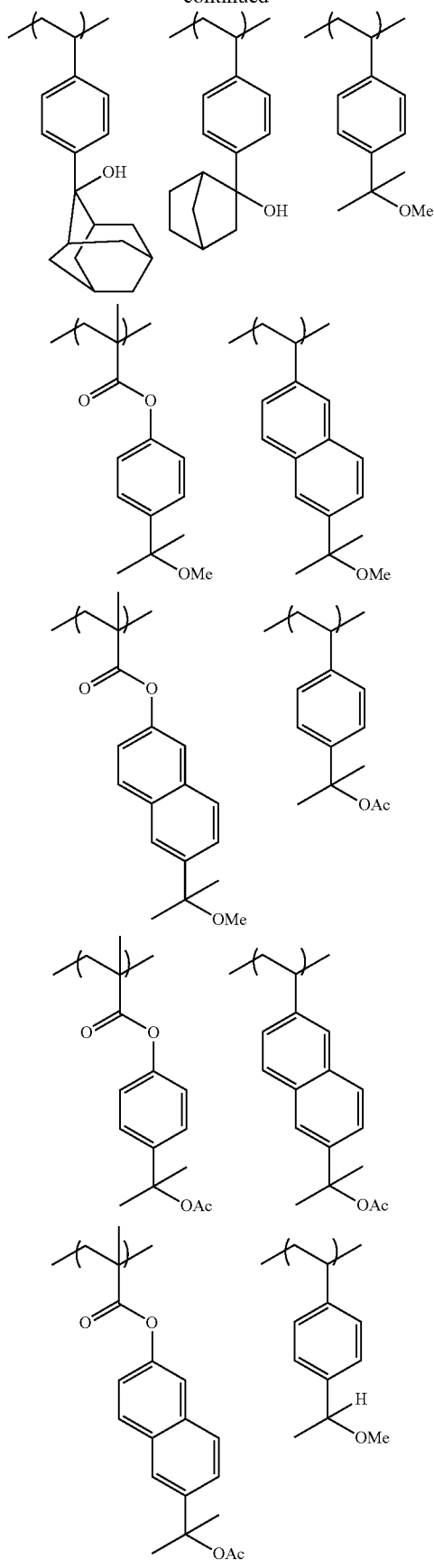

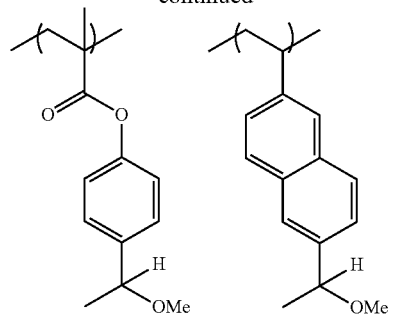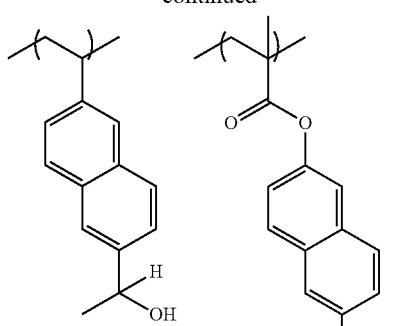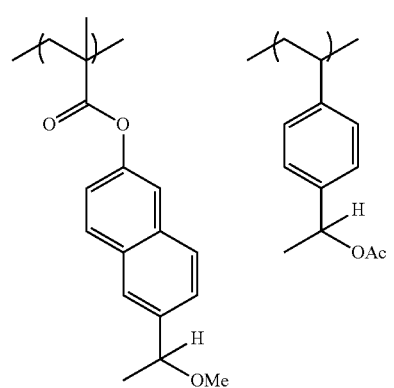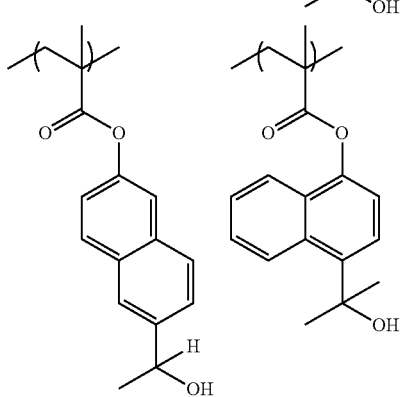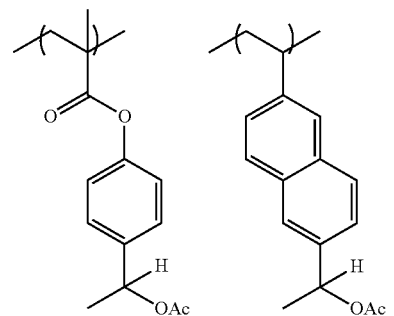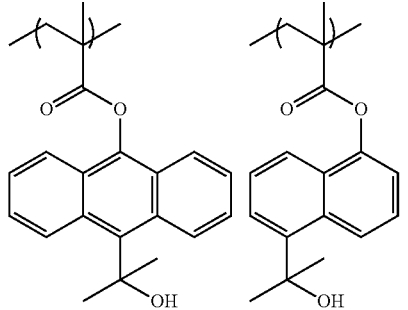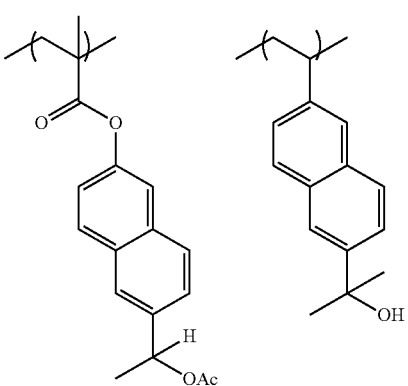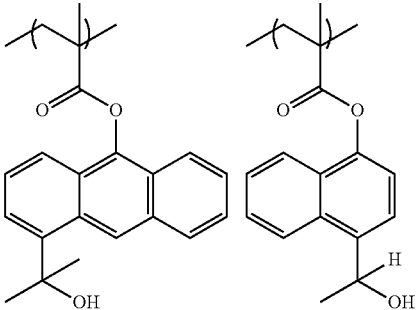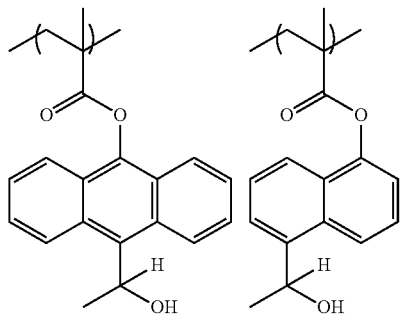

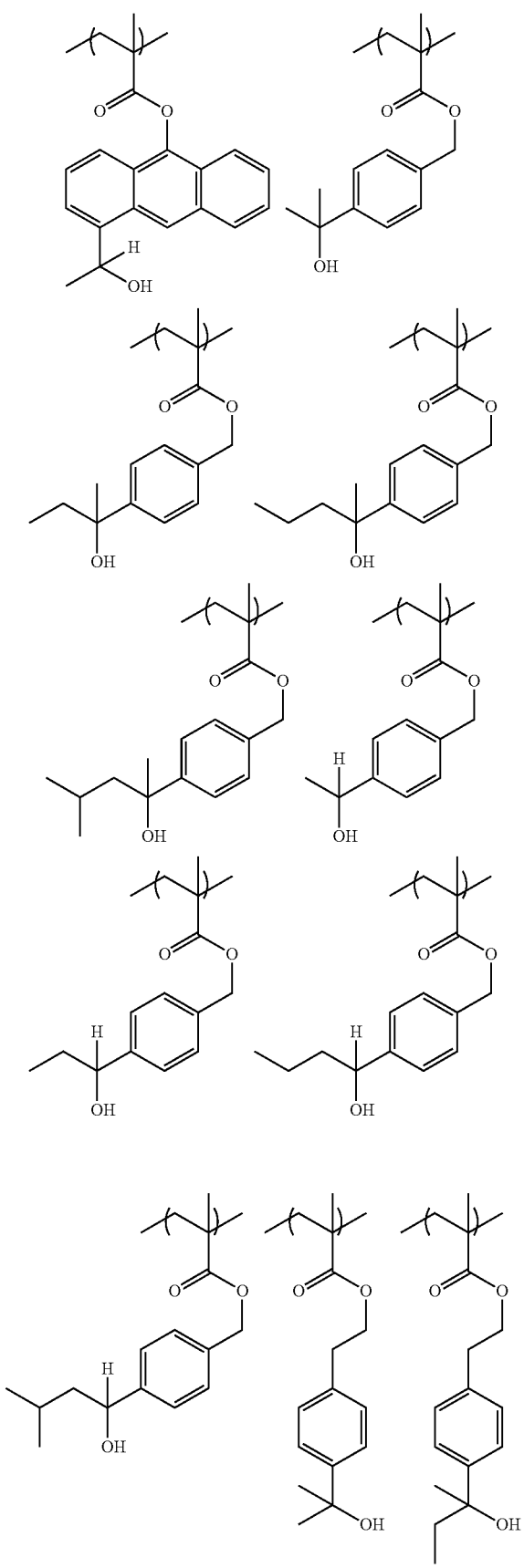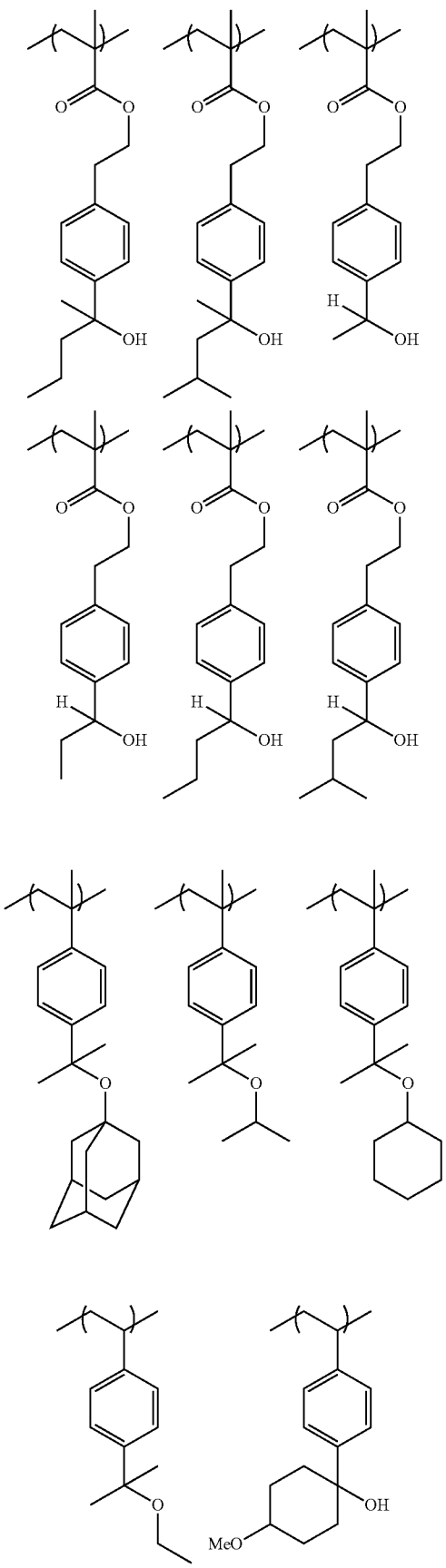

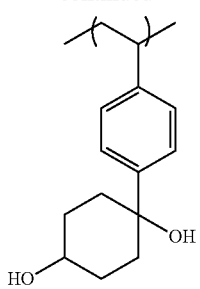

The recurring units (B5) are preferably incorporated in a range of at least 5 mol %, more preferably at least 10 mol % and up to 70 mol %, more preferably up to 60 mol %, based on the overall recurring units of the polymer.

Preferably recurring units (B1) to (B5) account for at least 60 mol %, and more preferably at least 70 mol %, based on the overall recurring units of the polymer because the range ensures that the negative resist composition has necessary properties.

The polymer (B') may further comprise recurring units of at least one type selected from recurring units having formulae (a1) to (a6). Notably these recurring units are simply referred to as recurring units (a1) to (a6).

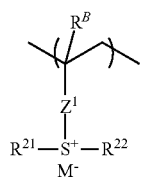
(a1)

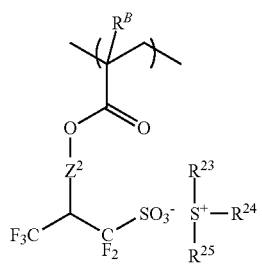
(a2)

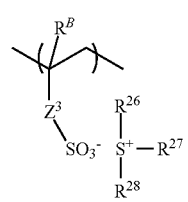
(a3)

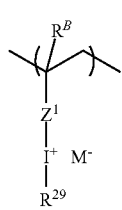
(a4)

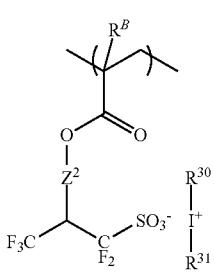
(a5)

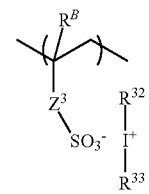
(a6)

Herein $R^B$ is each independently hydrogen or methyl. $Z^1$ is a single bond, phenylene group, —O—$Z^{12}$—, or —C(=O)—$Z^{11}$-$Z^{12}$—, wherein $Z^{11}$ is —O— or —NH—, $Z^{12}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety. $Z^2$ is a single bond or —$Z^{21}$—C(=O)—O—, wherein $Z^{21}$ is a $C_1$-$C_{20}$ straight, branched or cyclic divalent hydrocarbon group which may contain a heteroatom-containing moiety. $Z^3$ is a single bond, methylene, ethylene, phenylene, fluorinated phenylene, —O—$Z^{32}$—, or —C(=O)—$Z^{31}$-$Z^{32}$—, wherein $Z^{31}$ is —O— or —NH—, $Z^{32}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety. M⁻ is a non-nucleophilic counter ion. $R^{21}$ to $R^{33}$ are each independently a $C_1$-$C_{20}$ straight, branched or cyclic monovalent hydrocarbon group in which at least one hydrogen atom may be replaced by a moiety containing a heteroatom such as oxygen, sulfur, nitrogen or halogen, or in which at least one carbon atom may be replaced by a moiety containing a heteroatom such as oxygen, sulfur or nitrogen, so that the group may contain a hydroxy, cyano, carbonyl, ether bond, ester bond, sulfonic acid ester bond, carbonate bond, lactone ring, sultone ring, carboxylic anhydride, or haloalkyl moiety. $R^{21}$ and $R^{22}$ may bond together to form a ring with the sulfur atom to which they are attached, or any two of $R^{23}$, $R^{24}$ and $R^{25}$ or any two of $R^{26}$, $R^{27}$ and $R^{28}$ may bond together to form a ring with the sulfur atom to which they are attached.

In formulae (a2) and (a5) wherein $Z^2$ is —$Z^{21}$—C(=O)—O—, $Z^{21}$ is a divalent hydrocarbon group which may contain a heteroatom-containing moiety. Illustrative, non-limiting examples of the hydrocarbon group $Z^{21}$ are given below.

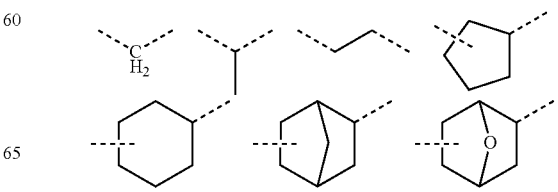

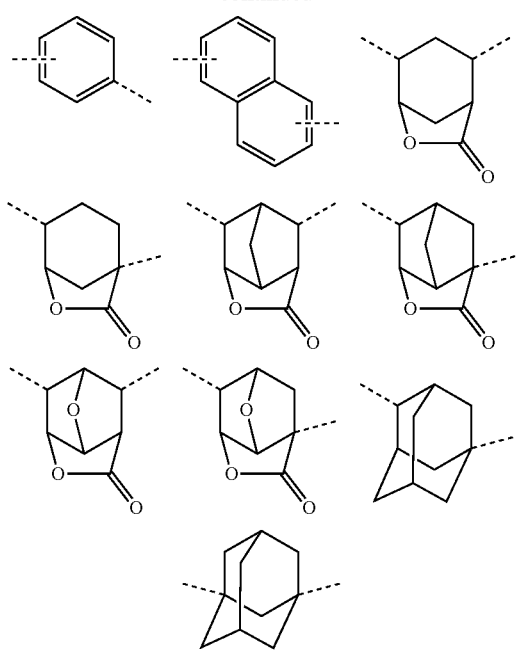

Examples of the sulfonium cation in formulae (a2) and (a3) wherein any two of $R^{23}$, $R^{24}$ and $R^{25}$ or any two of $R^{26}$, $R^{27}$ and $R^{28}$ bond together to form a ring with the sulfur atom to which they are attached, are shown below.

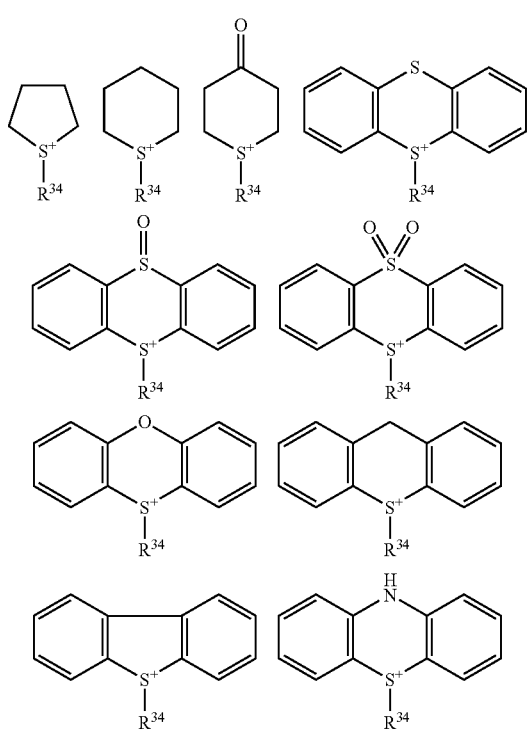

It is noted that $R^{34}$ is the same as defined and exemplified for $R^{21}$ to $R^{33}$ Specific examples of the sulfonium cation in formulae (a2) and (a3) are shown below, but not limited thereto.

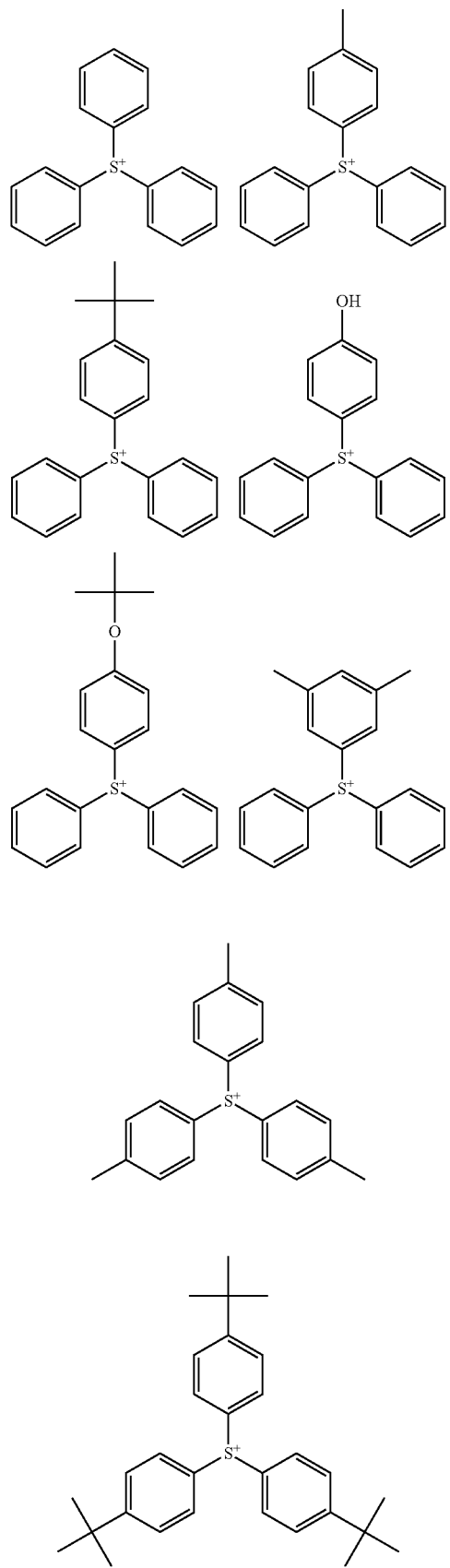

-continued
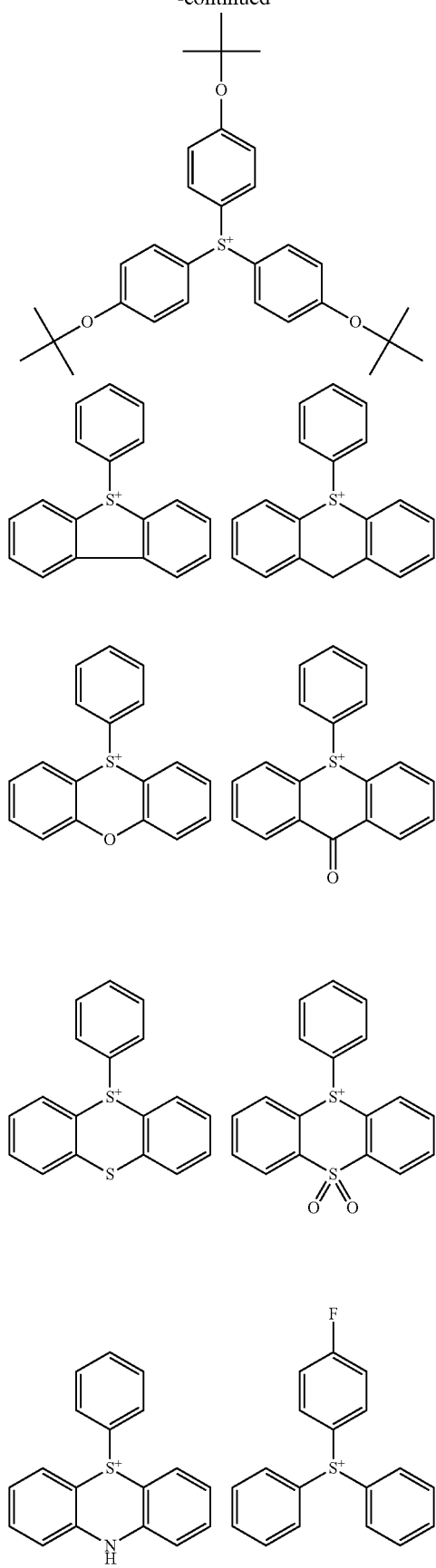
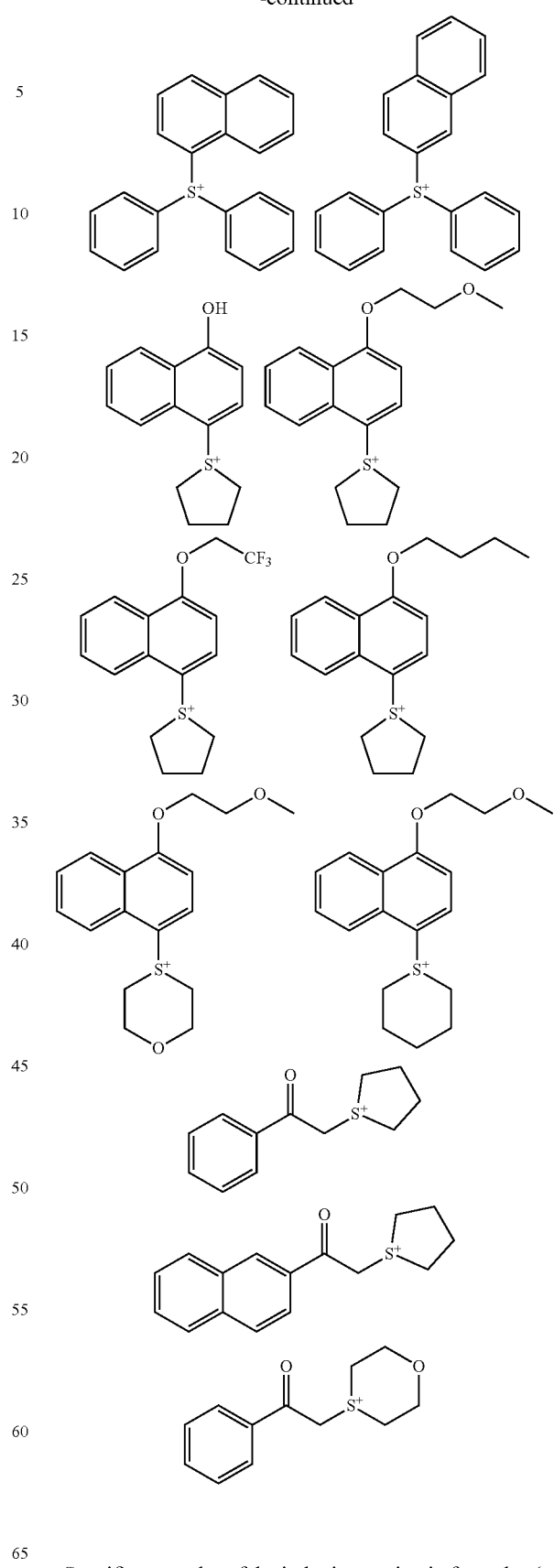
Specific examples of the iodonium cation in formulae (a5) and (a6) are shown below, but not limited thereto.

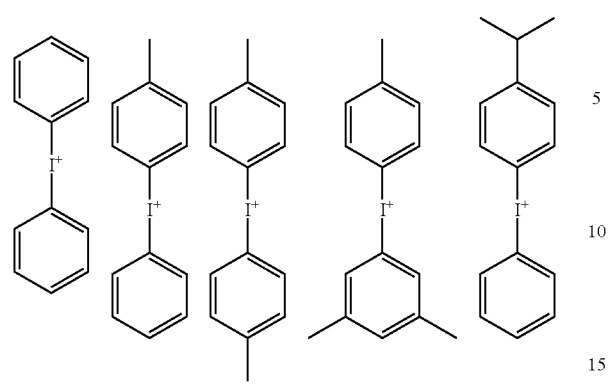
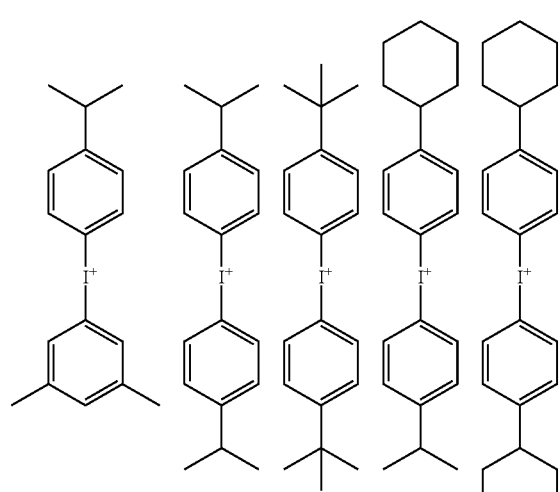
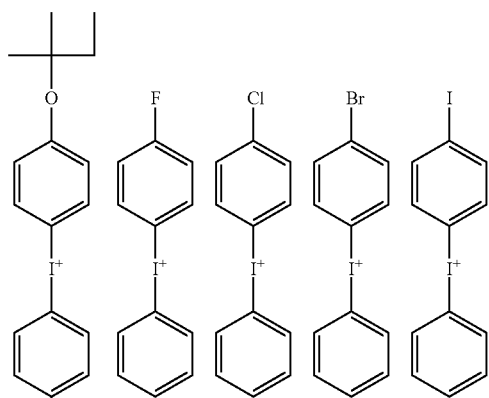
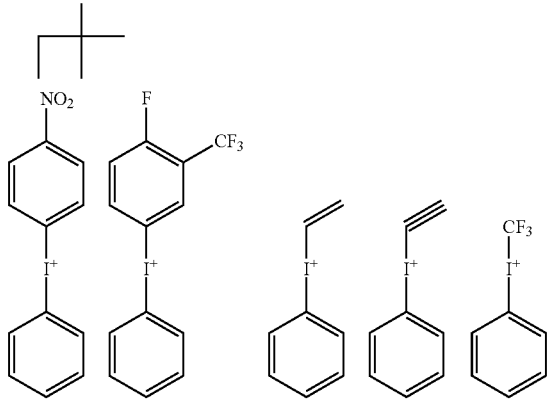
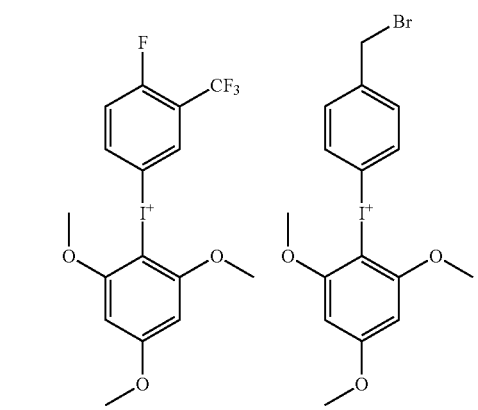
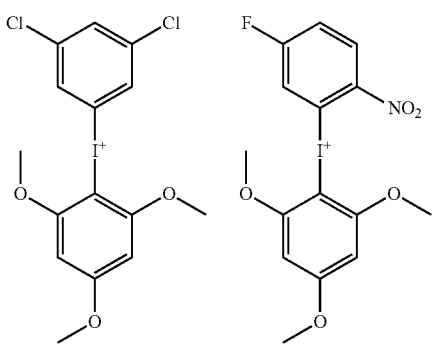

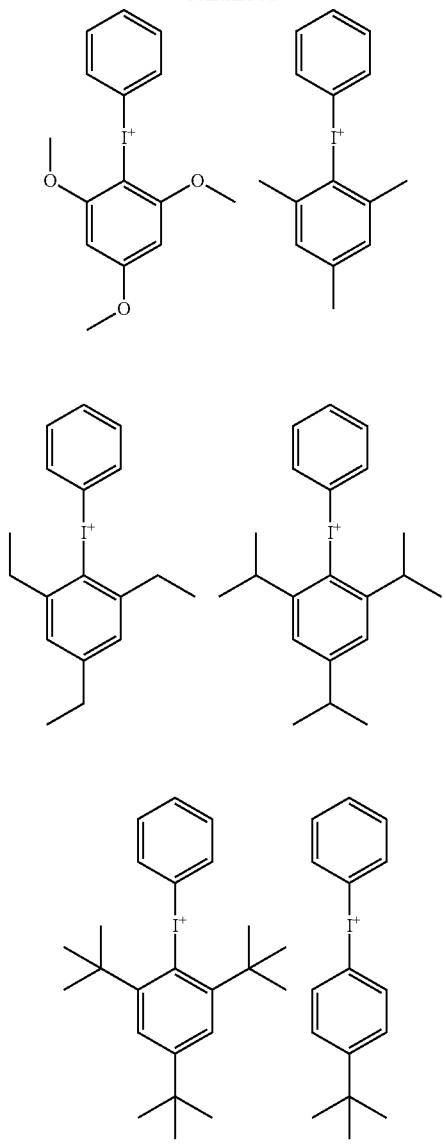

The recurring units (a1) to (a6) are units capable of generating an acid upon receipt of high-energy radiation. With the relevant units bound into a polymer, an appropriate control of acid diffusion becomes possible, and a pattern with minimal LER can be formed. Since the acid-generating unit is bound to a polymer, the phenomenon that acid volatilizes from the exposed region and re-deposits on the unexposed region during bake in vacuum is suppressed. This is effective for reducing LER and for suppressing unwanted negative tone reaction in the unexposed region for thereby reducing defects. The content of recurring units (a1) to (a6) is preferably 0.5 to 20 mol % based on the overall recurring units of polymer (B').

In the polymer, (meth)acrylate and other recurring units having an adhesive group such as lactone structure or hydroxyl group (other than phenolic hydroxyl group) may be incorporated for fine adjustment of properties of a resist film, though they are optional. Examples of the (meth) acrylate units having such an adhesive group include units having the formulae (b1) to (b3):

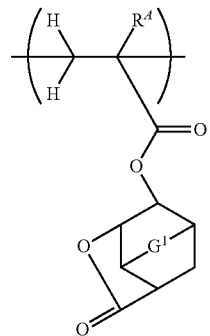

(b1)

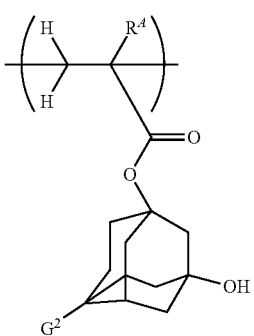

(b2)

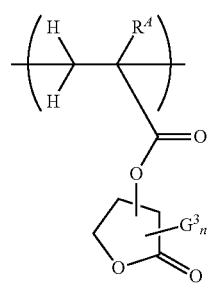

(b3)

wherein $R^A$ is as defined above, $G^1$ is —O— or methylene, $G^2$ is hydrogen or hydroxyl, $G^3$ is a $C_1$-$C_4$ straight, branched or cyclic alkyl group, and n is an integer of 0 to 3. These units do not exhibit acidity and may be used as supplemental units for imparting adhesion to substrates or for adjusting solubility.

In polymer (B), an appropriate content of recurring units (B1) is 50 to 95 mol %, more preferably 70 to 85 mol %; an appropriate content of recurring units (B2) to (B4) is 0 to 30 mol %, more preferably 3 to 20 mol %; an appropriate content of other recurring units is 0 to 30 mol %, more preferably 0 to 20 mol %.

Where the polymer (B') is free of recurring units (a1) to (a6), it is preferably a polymer comprising 25 to 95 mol %, more preferably 40 to 85 mol % of recurring units (B1), and 0 to 30 mol %, more preferably 3 to 20 mol % of recurring units (B2) to (B4). An appropriate content of recurring units (B5) is 5 to 70 mol %, more preferably 10 to 60 mol %. The other recurring units may be incorporated in a range of 0 to 30 mol %, preferably 0 to 20 mol %.

Where the polymer (B') contains recurring units (a1) to (a6), it is preferably a polymer comprising 25 to 94.5 mol %, more preferably 36 to 85 mol % of recurring units (B1), 0 to 30 mol %, more preferably 3 to 20 mol % of recurring units (B2) to (B4). An appropriate content of recurring units (B5) is 5 to 70 mol %, more preferably 10 to 60 mol %.

A total content of recurring units (B1) to (B5) is preferably 60 to 99.5 mol %. An appropriate content of recurring units (a1) to (a6) is 0.5 to 20 mol %, more preferably 1 to 10 mol %. The other recurring units may be incorporated in a range of 0 to 30 mol %, preferably 0 to 20 mol %.

As the polymer (B'), a polymer comprising recurring units having the formula (B1-1), recurring units having the formula (B5-1), and recurring units having the formula (a2) or (a5) is preferred.

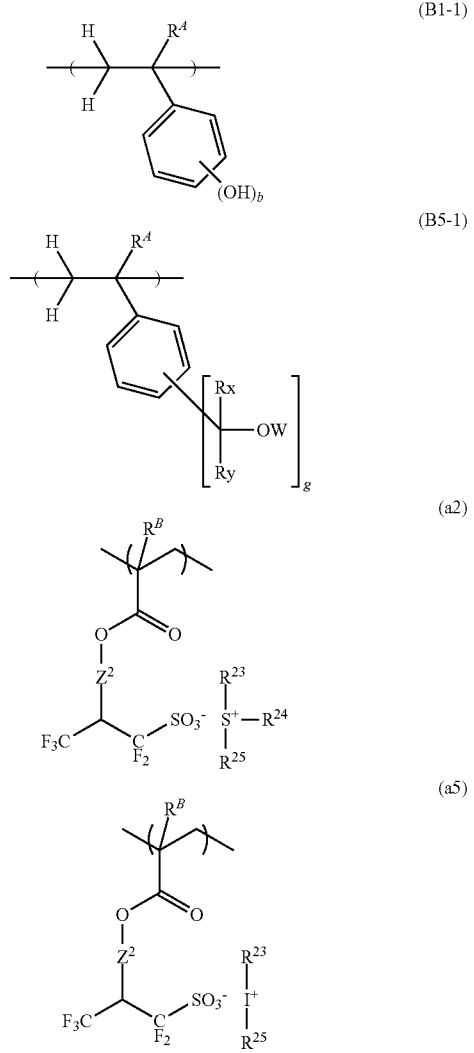

Herein $R^A$, $R^B$, $Z^2$, $R^{23}$, $R^{24}$, $R^{25}$, $R^{30}$, $R^{31}$, Rx, Ry, W, b, and g are as defined above.

Where the polymer (B') is used as the base polymer (B), it may be a mixture of a polymer free of recurring units (a1) to (a6) and a polymer comprising recurring units (a1) to (a6). In this embodiment, the polymer free of recurring units (a1) to (a6) is preferably used in an amount of 2 to 5,000 parts, more preferably 10 to 1,000 parts by weight per 100 parts by weight of the polymer comprising recurring units (a1) to (a6).

When the negative resist composition is used in the manufacture of photomasks, its coating thickness is up to 150 nm, preferably up to 100 nm in the lithography of advanced generation. In general, the dissolution rate in alkaline developer (typically 2.38 wt % TMAH aqueous solution) of the base polymer (used in the negative resist composition) is preferably set at 80 nm/sec or lower, more preferably at 50 nm/sec or lower, to form a fine size pattern, because an intense development process is often employed for minimizing defects due to resist residues. In the manufacture of a LSI chip from a wafer, for example, when the negative resist composition is processed by the EUV lithography process, the composition is often coated to a coating thickness of 100 nm or less because it is necessary to pattern fine lines of 50 nm or less. Because of a thin film, the pattern can be degraded by development. For this reason, the dissolution rate of the polymer is preferably set at 80 nm/sec or lower, more preferably at 50 nm/sec or lower. On the other hand, in the case of KrF lithography process, the resist composition is often coated as a thick film having a coating thickness of 200 nm or more, although the thickness varies with a particular purpose. In this case, the dissolution rate of the polymer is preferably designed at 90 nm/sec or higher.

The polymer may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to WO 2006/121096, JP-A 2004-115630, JP-A 2008-102383, and JP-A 2008-304590.

The polymer should preferably have a Mw of 1,000 to 50,000, and more preferably 2,000 to 20,000. A Mw of at least 1,000 eliminates the risk that pattern features are rounded at their top, inviting degradations of resolution and LER. A Mw of up to 50,000 eliminates the risk that LER is increased particularly when a pattern with a line width of up to 100 nm is formed. As used herein, Mw is measured by GPC versus polystyrene standards.

The polymer preferably has a narrow molecular weight distribution or dispersity (Mw/Mn) of 1.0 to 2.0, more preferably 1.0 to 1.8. A polymer with such a narrow dispersity eliminates any foreign particles left on the pattern or profile degradation of the pattern after development.

(C) Crosslinker

When only polymer (B) is used as the base polymer in the negative resist composition, a crosslinker is preferably added. When the base polymer contains polymer (B'), a crosslinker need not be added.

Suitable crosslinkers which can be used herein include melamine compounds, guanamine compounds, glycoluril compounds and urea compounds having substituted thereon at least one group selected from among methylol, alkoxymethyl and acyloxymethyl groups, epoxy compounds, isocyanate compounds, azide compounds, and compounds having a double bond such as an alkenyl ether group. These compounds may be used as an additive or introduced into a polymer side chain as a pendant. Hydroxy-containing compounds may also be used as the crosslinker.

Of the foregoing crosslinkers, examples of suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

These crosslinkers may be used alone or in admixture. An appropriate amount of the crosslinker used is 2 to 50 parts, and more preferably 5 to 30 parts by weight per 100 parts by weight of the base polymer. As long as the amount of the crosslinker is in the range, the risk of resolution being reduced by forming bridges between pattern features is mitigated.

(D) Fluorinated Polymer

The negative resist composition may further comprise (D) a fluorinated polymer comprising recurring units having the formula (D1) and recurring units of at least one type selected from recurring units having the formulae (D2), (D3), (D4), and (D5), for the purposes of enhancing contrast, preventing chemical flare of acid upon exposure to high-energy radiation, preventing mixing of acid from an anti-charging film in the step of coating an anti-charging film-forming material on a resist film, and suppressing unexpected unnecessary pattern degradation. Notably, recurring units having formulae (D1), (D2), (D3), (D4), and (D5) are simply referred to as recurring units (D1), (D2), (D3), (D4), and (D5), respectively. Since the fluorinated polymer also has a surface active function, it can prevent insoluble residues from re-depositing onto the substrate during the development step and is thus effective for preventing development defects.

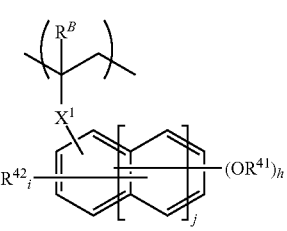

(D1)

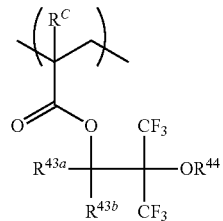

(D2)

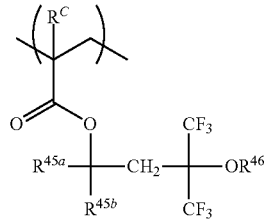

(D3)

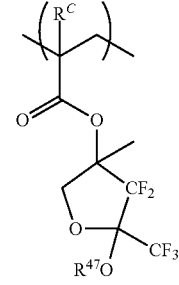

(D4)

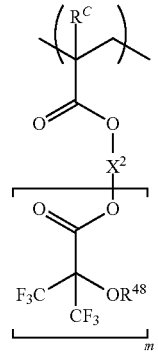

(D5)

Herein $R^B$ is each independently hydrogen or methyl. $R^C$ is each independently hydrogen, fluorine, methyl or trifluoromethyl. $R^{41}$ is hydrogen or a $C_1$-$C_5$ straight or branched monovalent hydrocarbon group in which a heteroatom may intervene in a carbon-carbon bond. $R^{42}$ is a $C_1$-$C_5$ straight or branched monovalent hydrocarbon group in which a heteroatom may intervene in a carbon-carbon bond. $R^{43a}$, $R^{43b}$, $R^{45a}$ and $R^{45b}$ are each independently hydrogen or a $C_1$-$C_{10}$ straight, branched or cyclic alkyl group. $R^{44}$, $R^{46}$, $R^{47}$ and $R^{48}$ are each independently hydrogen, a $C_1$-$C_{15}$ straight, branched or cyclic monovalent hydrocarbon group or monovalent fluorinated hydrocarbon group, or an acid labile group, with the proviso that an ether or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$. The subscript h is an integer of 1 to 3, i is an integer in the range: $0 \leq i \leq 5+2j-h$, j is 0 or 1, and m is an integer of 1 to 3. $X^1$ is a single bond, —C(=O)—O— or —C(=O)—NH—. $X^2$ is a $C_1$-$C_{20}$ straight, branched or cyclic (m+1)-valent hydrocarbon group or fluorinated hydrocarbon group.

Suitable monovalent hydrocarbon groups include alkyl, alkenyl and alkynyl groups, with the alkyl groups being preferred. Suitable alkyl groups include methyl, ethyl, n-propyl, isopropyl, n-butyl, isobutyl, sec-butyl, and n-pentyl. In these groups, a moiety containing a heteroatom such as oxygen, sulfur or nitrogen may intervene in a carbon-carbon bond.

In formula (D1), —$OR^{41}$ is preferably a hydrophilic group. In this case, $R^{41}$ is preferably hydrogen or a $C_1$-$C_5$ alkyl group in which oxygen intervenes in a carbon-carbon bond.

Examples of the recurring unit (D1) are given below, but not limited thereto. Herein $R^B$ is as defined above.

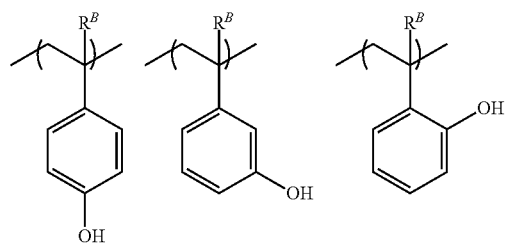

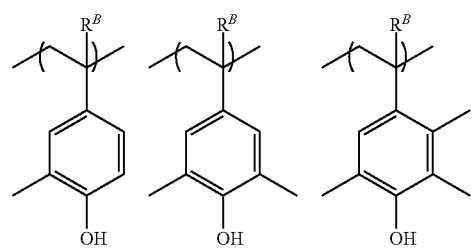

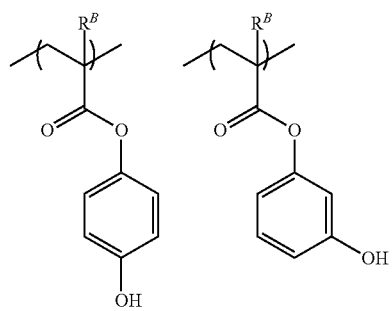

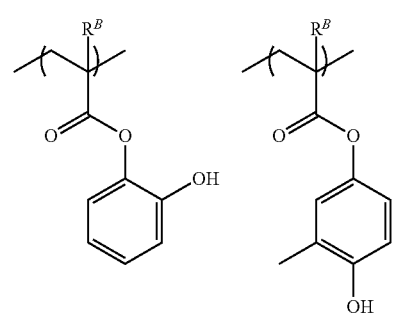

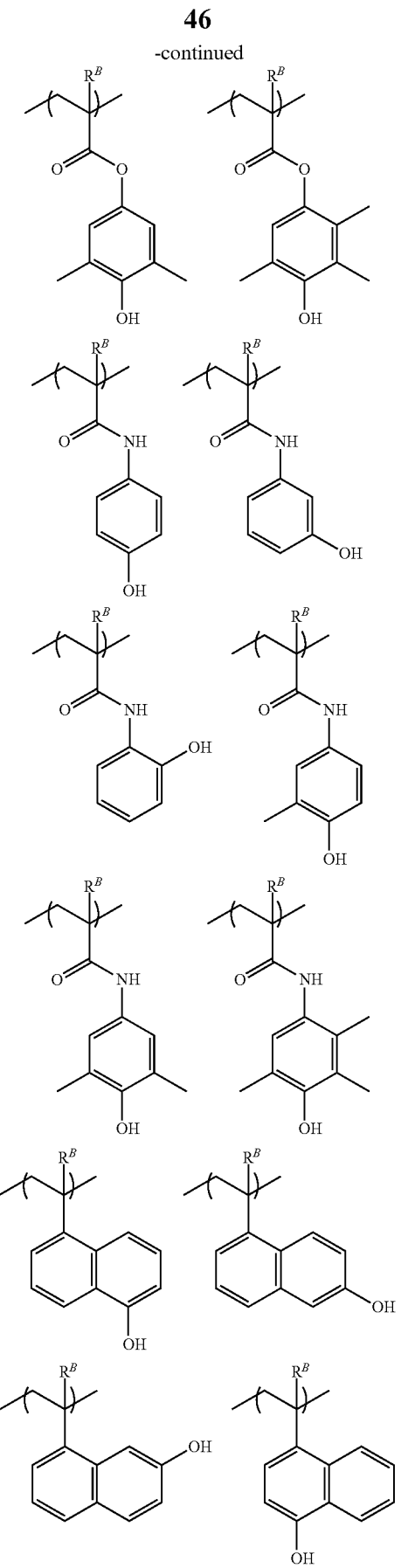

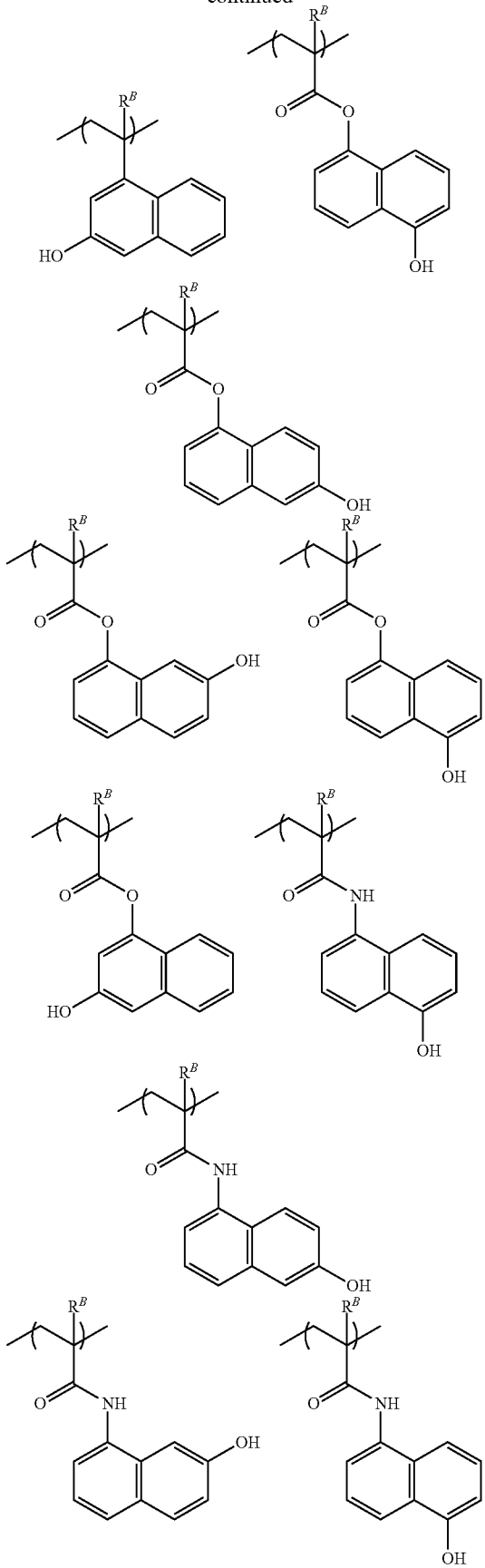

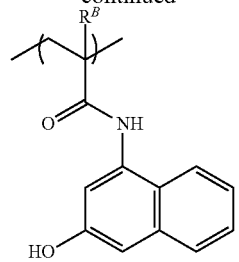

In formula (D1), $X^1$ is preferably —C(=O)—O— or —C(=O)—NH—. Also preferably $R^B$ is methyl. The inclusion of carbonyl in $X^1$ enhances the ability to trap the acid originating from the anti-charging film. A polymer wherein $R^B$ is methyl is a rigid polymer having a high glass transition temperature (Tg) which is effective for suppressing acid diffusion. As a result, the stability with time of a resist film is improved, and neither resolution nor pattern profile is degraded.

In formulae (D2) and (D3), examples of the alkyl group represented by $R^{43a}$, $R^{43b}R^{45a}$ and $R^{45b}$ include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbornyl. Inter alia, $C_1$-$C_6$ straight, branched or cyclic alkyl groups are preferred.

In formulae (D2) to (D5), examples of the monovalent hydrocarbon group represented by $R^{44}$, $R^{46}$, $R^{47}$ and $R^{48}$ include alkyl, alkenyl and alkynyl groups, with the alkyl groups being preferred. Suitable alkyl groups include n-undecyl, n-dodecyl, tridecyl, tetradecyl and pentadecyl as well as those exemplified above. The monovalent fluorinated hydrocarbon groups correspond to the foregoing monovalent hydrocarbon groups in which one or more or even all carbon-bonded hydrogen atoms are substituted by fluorine atoms.

Examples of the $C_1$-$C_{20}$ straight, branched or cyclic (m+1)-valent hydrocarbon group or fluorinated hydrocarbon group include the foregoing monovalent hydrocarbon groups and monovalent fluorinated hydrocarbon groups, with a number (m) of hydrogen atoms being eliminated.

Examples of the recurring units (D2) to (D5) are given below, but not limited thereto. Herein $R^C$ is as defined above.

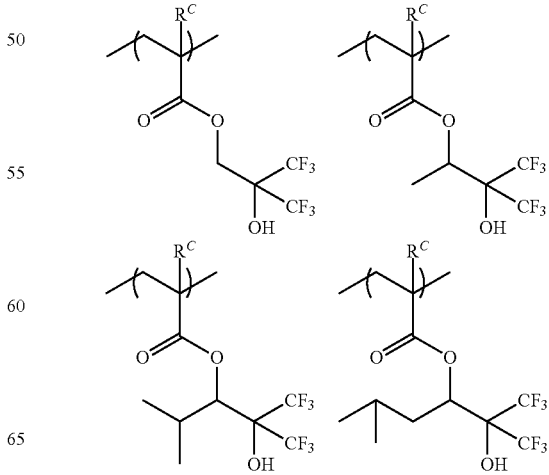

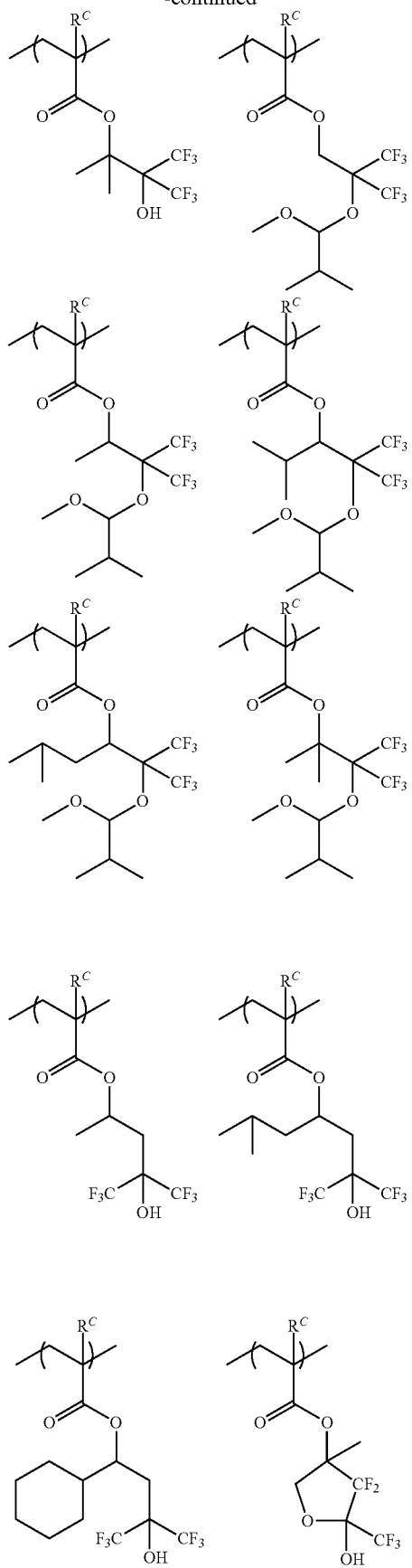
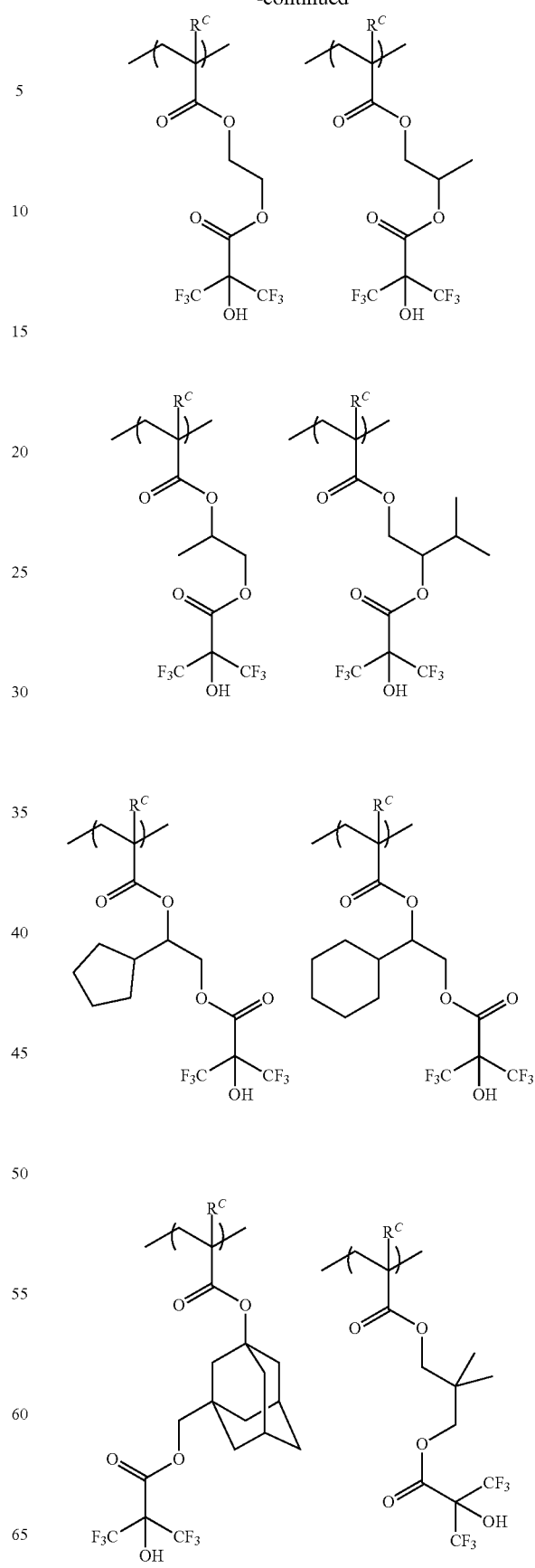

-continued

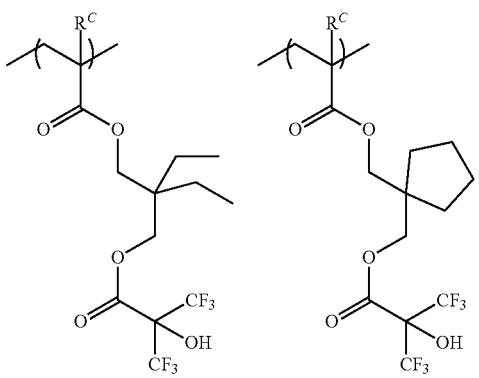

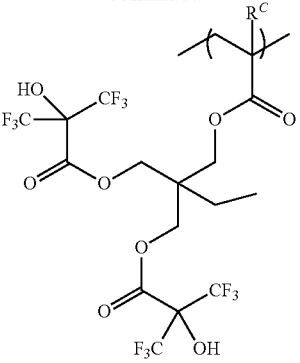

-continued

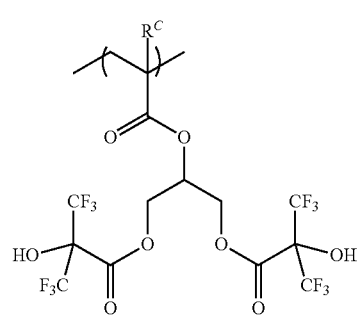

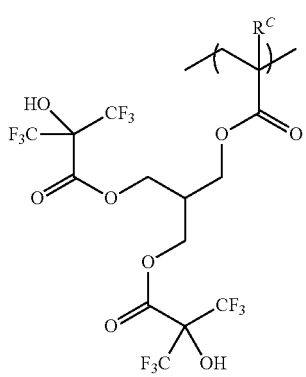

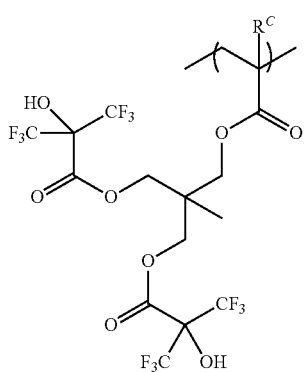

The recurring unit (D1) is preferably incorporated in an amount of 5 to 85 mol %, more preferably 15 to 80 mol % based on the overall recurring units of the fluorinated polymer (D). The recurring units (D2) to (D5), which may be used alone or in admixture, are preferably incorporated in an amount of 15 to 95 mol %, more preferably 20 to 85 mol % based on the overall recurring units of the fluorinated polymer (D).

The fluorinated polymer (D) may comprise additional recurring units as well as the recurring units (D1) to (D5). Suitable additional recurring units include those described in U.S. Pat. No. 9,091,918 (JP-A 2014-177407, paragraphs [0046]-[0078]). When the fluorinated polymer (D) comprises additional recurring units, their content is preferably up to 50 mol % based on the overall recurring units.

The fluorinated polymer (D) may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to JP-A 2004-115630.

The fluorinated polymer (D) should preferably have a Mw of 2,000 to 50,000, and more preferably 3,000 to 20,000. A fluorinated polymer with a Mw of less than 2,000 helps acid diffusion, degrading resolution and detracting from age stability. A polymer with too high Mw has a reduced solubility in solvent, leading to coating defects. The fluorinated polymer preferably has a dispersity (Mw/Mn) of 1.0 to 2.2, more preferably 1.0 to 1.7.

The fluorinated polymer (D) is preferably used in an amount of 0.01 to 30 parts, more preferably 0.1 to 20 parts by weight per 100 parts by weight of the base polymer (B).

(E) Organic Solvent

The negative resist composition may further comprise (E) an organic solvent. The organic solvent used herein is not particularly limited as long as the components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, propylene glycol monomethyl ether, cyclohexanone, ethyl lactate, γ-butyrolactone, and mixtures thereof.

An appropriate amount of the organic solvent (E) used is 200 to 10,000 parts, more preferably 400 to 5,000 parts by weight per 100 parts by weight of the base polymer (B).

(F) Acid Generator

The negative resist composition may further comprise (F) an acid generator in order that the composition function as a chemically amplified negative resist composition. The acid generator is typically a compound capable of generating acid in response to actinic light or radiation (known as photoacid generator). It may be any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. These PAGs may be used alone or in admixture of two or more.

Suitable PAGs include nonafluorobutane sulfonate, partially fluorinated sulfonates described in JP-A 2012-189977, paragraphs [0247]-[0251], partially fluorinated sulfonates described in JP-A 2013-101271, paragraphs [0261]-[0265], and those described in JP-A 2008-111103, paragraphs [0122]-[0142] and JP-A 2010-215608, paragraphs [0080]-[0081]. Among others, arylsulfonate and alkanesulfonate type PAGs are preferred because they generate acids having an appropriate strength to promote reaction of base polymer (B) with crosslinker (C). The PAG capable of generating an acid having a pKa value in the range of −3.0 to 1.5, more preferably −1.0 to 1.5 is preferred because the effect of improving LER by combining the generated acid with the sulfonium compound (A) to induce exchange reaction is achievable.

The preferred acid generators are compounds having a sulfonium anion of the structure shown below. Notably the cation that pairs with the anion is as exemplified for the sulfonium cation in formulae (a2) and (a3).

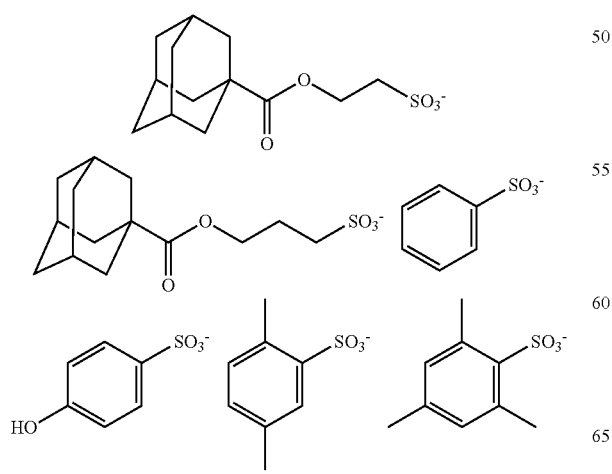

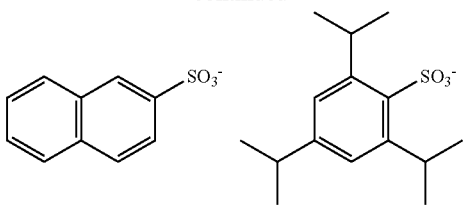

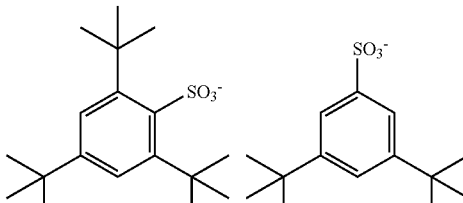

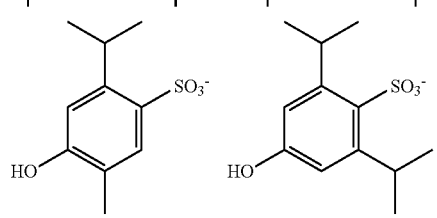

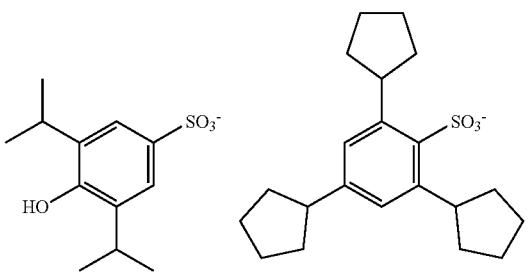

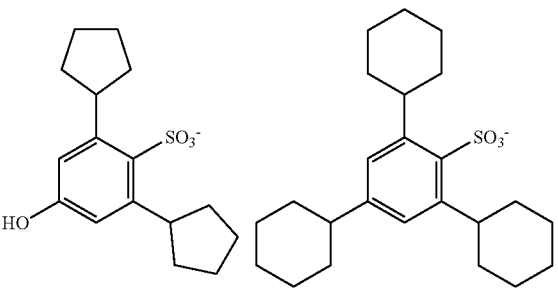

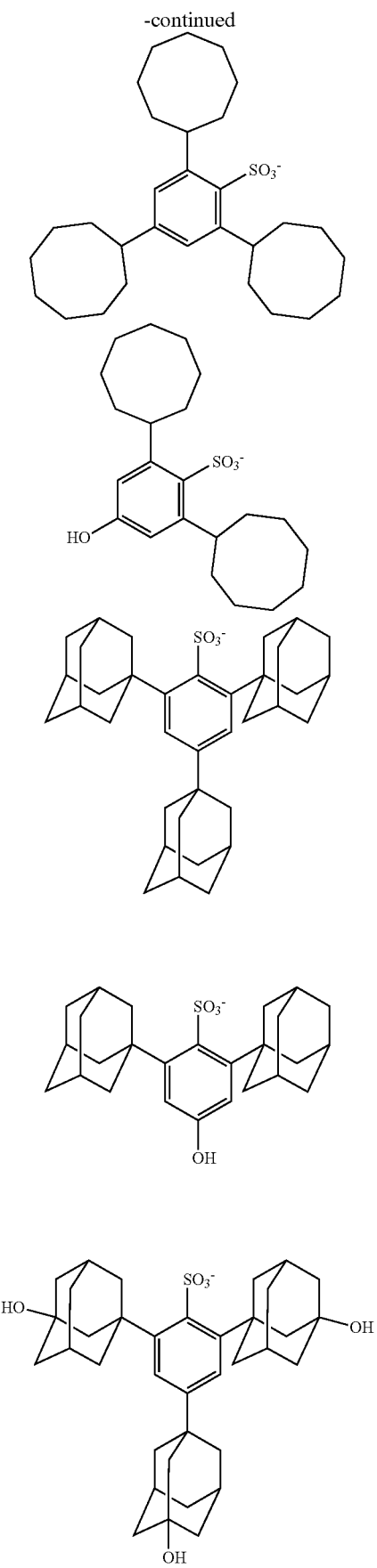
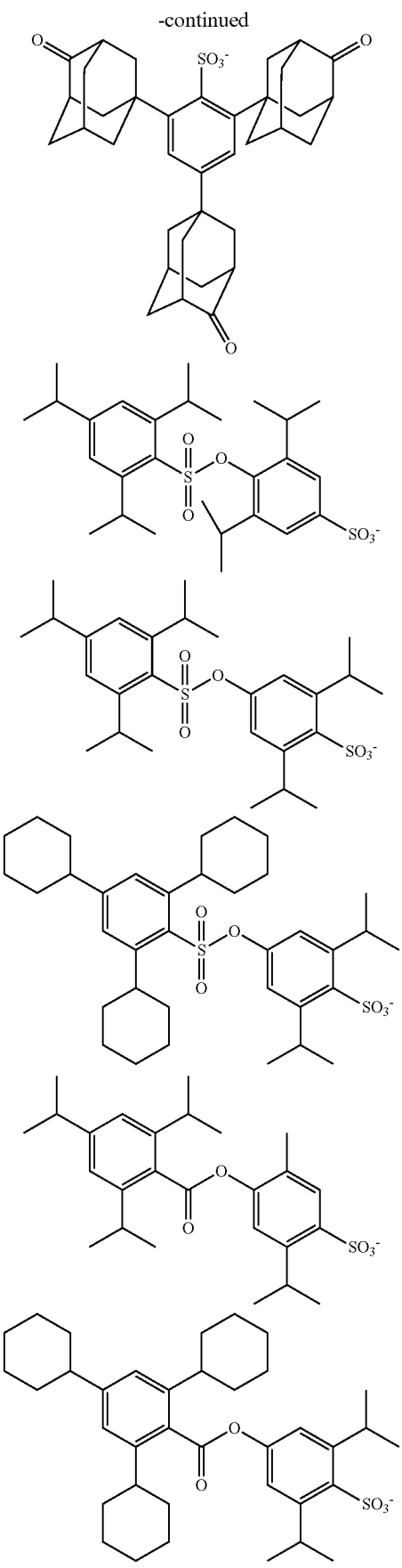

57
-continued
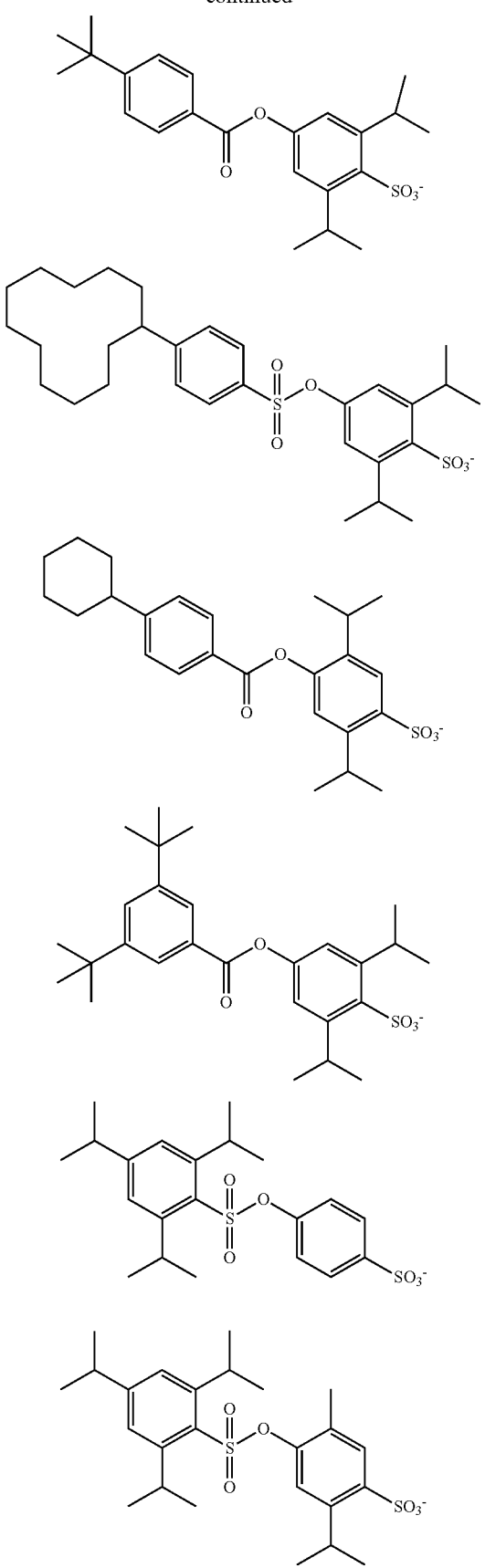
58
-continued
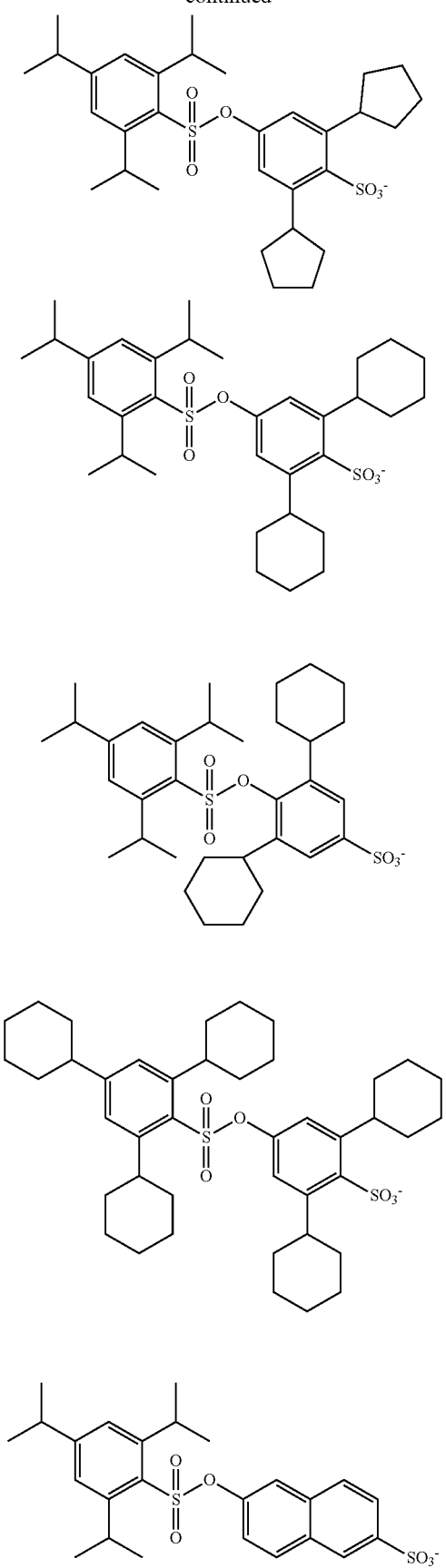

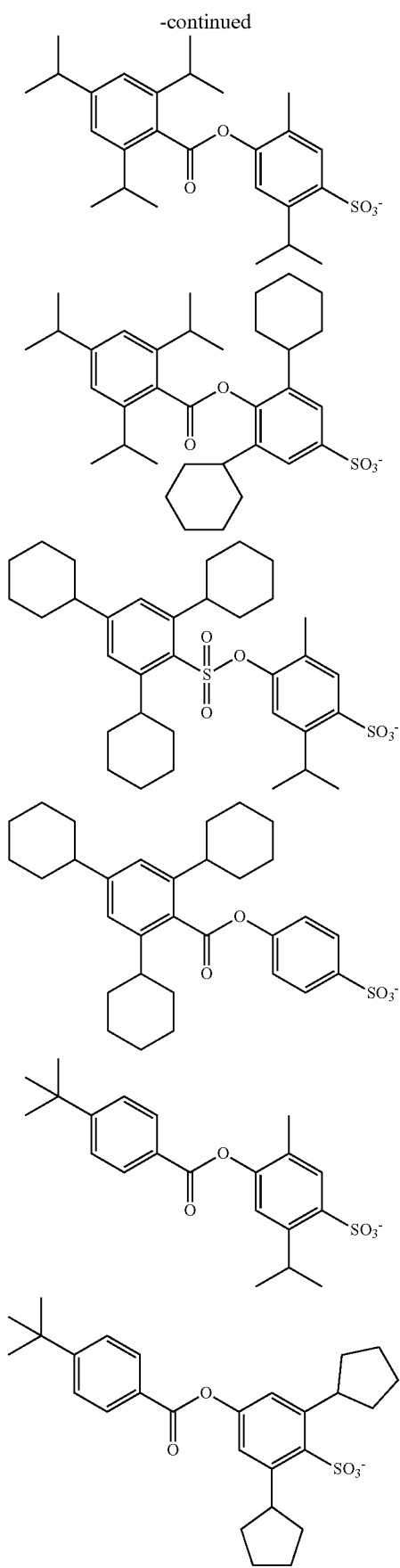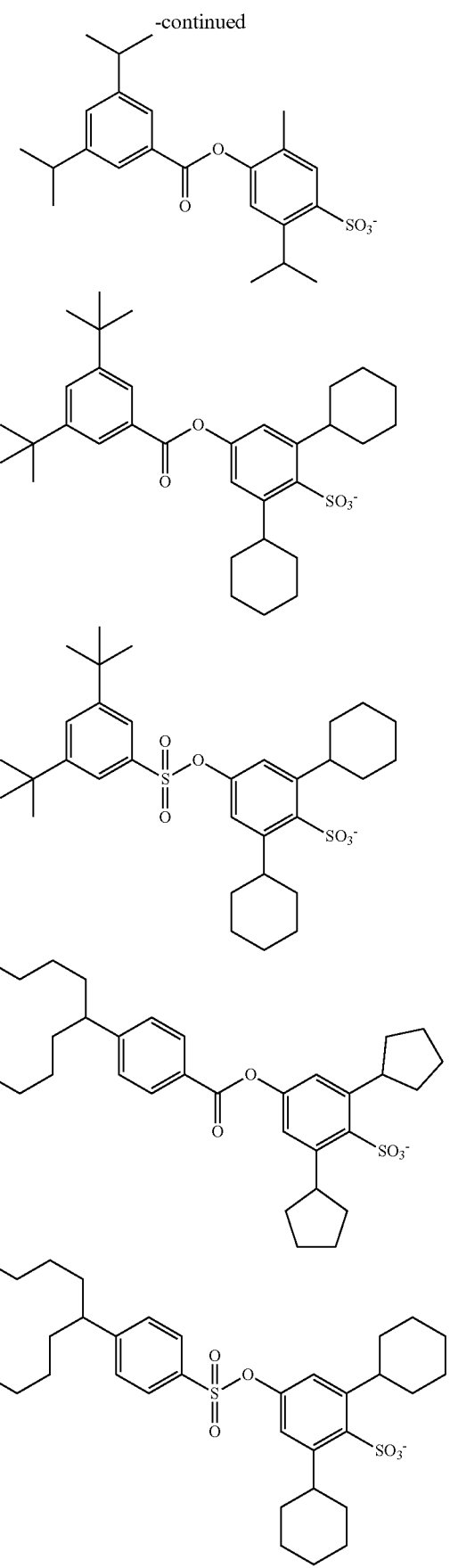

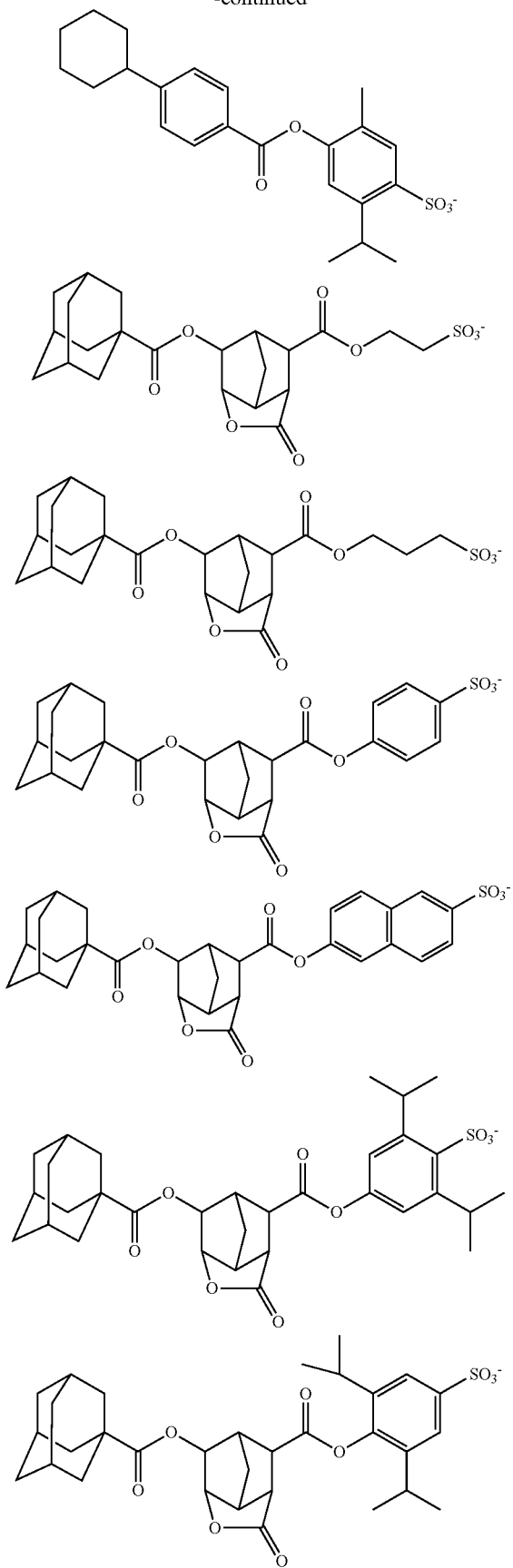
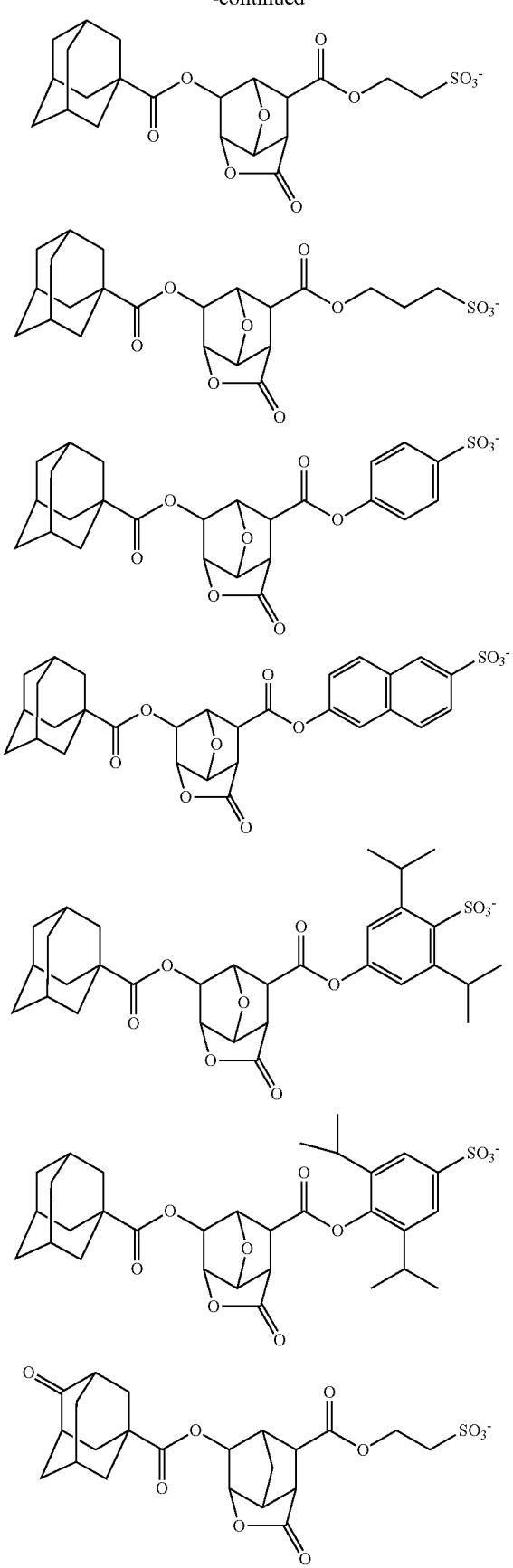

63
-continued
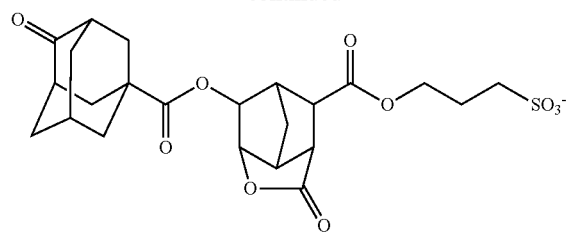
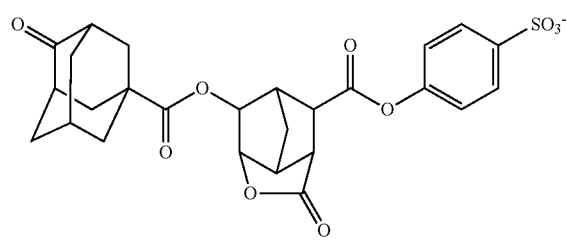
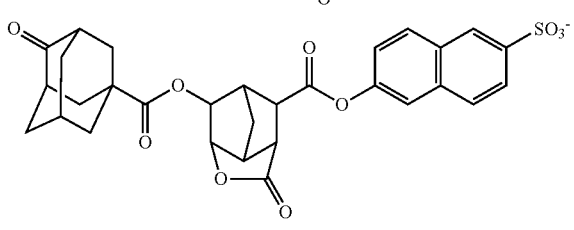
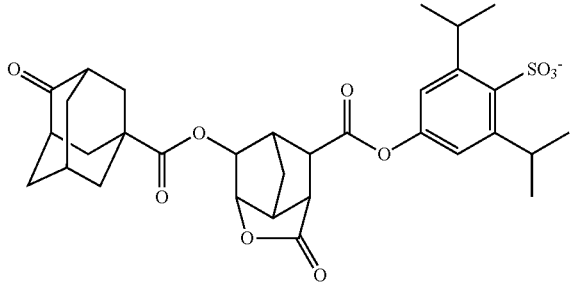
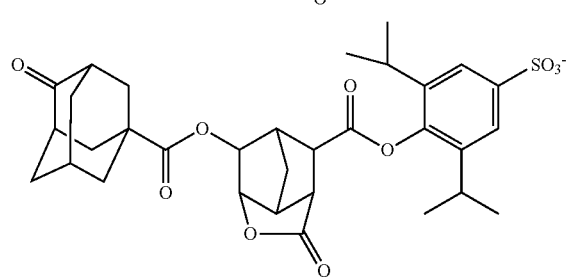
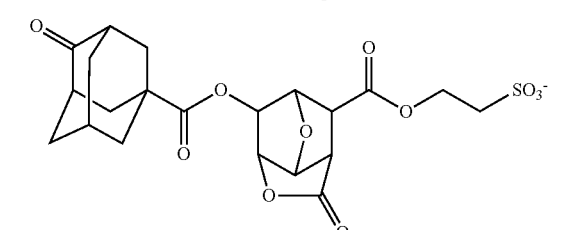
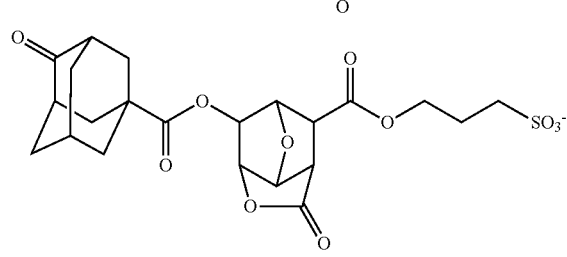
64
-continued
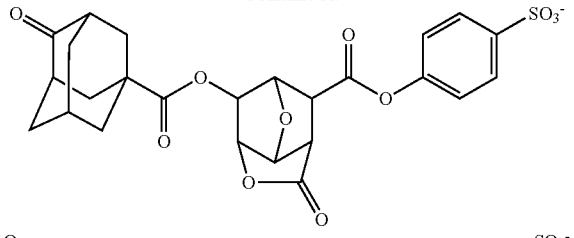
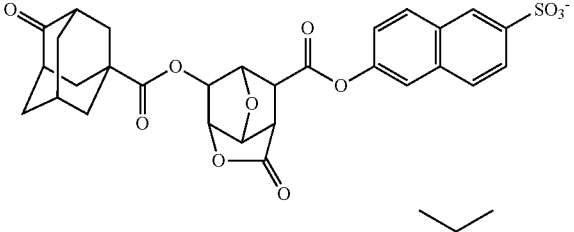
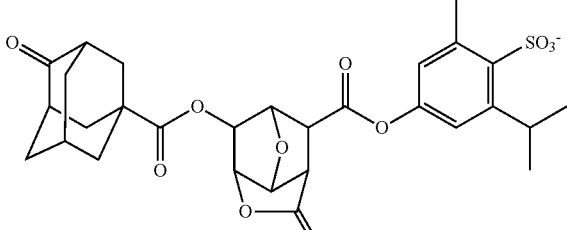
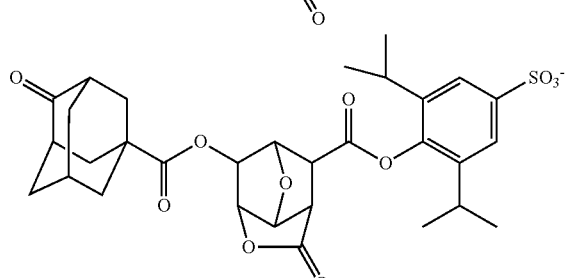
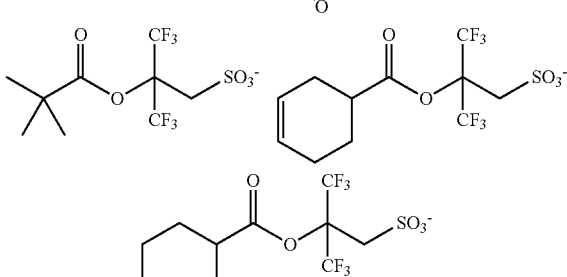
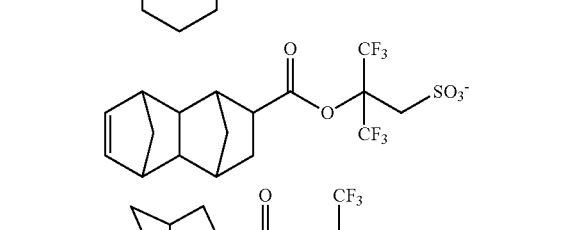
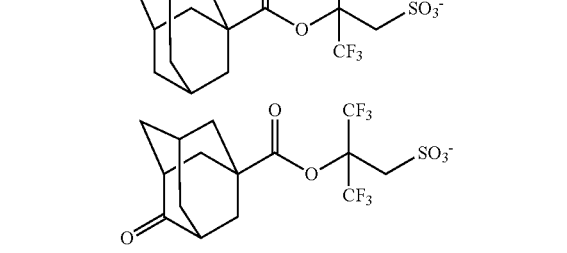

-continued

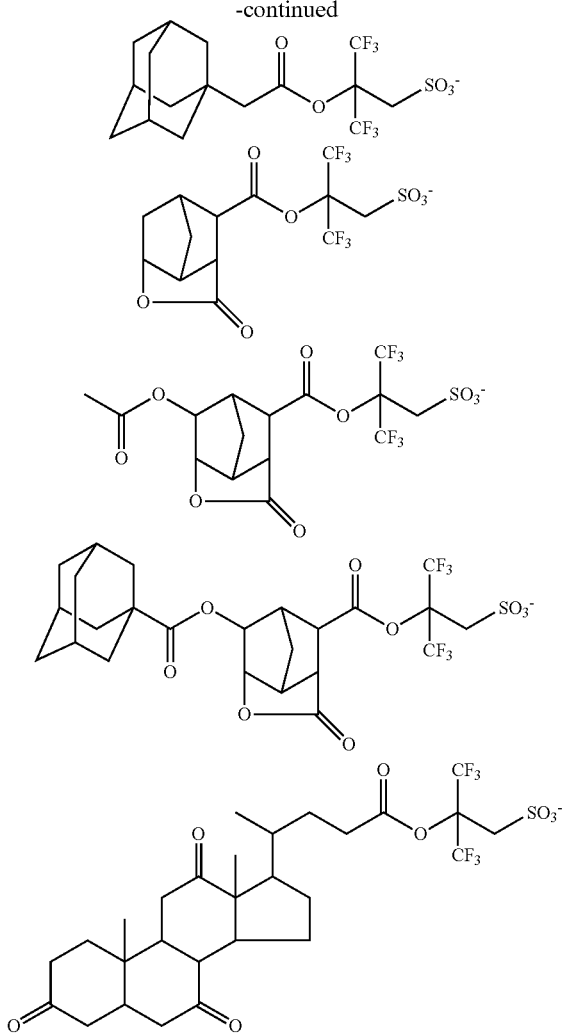

An appropriate amount of the acid generator (F) used is 2 to 20 parts, more preferably 5 to 15 parts by weight per 100 parts by weight of the base polymer (B). Where the base polymer contains recurring units (a1) to (a6), the acid generator (F) may be omitted.

(G) Basic Compound

In the resist composition, (G) a basic compound may be added as the acid diffusion inhibitor (other than component (A)) for the purpose of correcting a pattern profile or the like. The basic compound is effective for controlling acid diffusion. Even when the resist film is applied to a processable substrate having an outermost surface layer made of a chromium-containing material, the basic compound is effective for minimizing the influence of the acid generated in the resist film on the chromium-containing material. An appropriate amount of the basic compound added is 0 to 10 parts, and more preferably 0 to 5 parts by weight per 100 parts by weight of the base polymer (B).

Numerous basic compounds are known useful including primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts. Examples are described in Patent Document 9, for example, and any such compounds are useful. The basic compounds may be used alone or in admixture. Of the foregoing basic compounds, preferred are tris[2-(methoxymethoxy)ethyl]amine, tris[2-(methoxymethoxy)ethyl]amine-N-oxide, dibutylaminobenzoic acid, morpholine derivatives and imidazole derivatives.

(H) Surfactant

In the resist composition, any of surfactants commonly used for improving coating characteristics to the processable substrate may be added as an optional component. Numerous surfactants are known in the art including PF-636 (Omnova Solutions), FC-4430 (3M), and those described in JP-A 2004-115630, for example. A choice may be made with reference to such patent documents. An appropriate amount of the surfactant (H) used is 0 to 5 parts by weight per 100 parts by weight of the base polymer (B).

Process

A further embodiment of the invention is a resist pattern forming process comprising the steps of applying the resist composition defined above onto a processable substrate to form a resist film thereon, exposing the resist film patternwise to high-energy radiation, and developing the resist film in an alkaline developer to form a resist pattern.

Pattern formation using the negative resist composition of the invention may be performed by well-known lithography processes. In general, the resist composition is first applied onto a processable substrate such as a substrate for IC fabrication (e.g., Si, SiO, $SiO_2$, SiN, SiON, TiN, WSi, BPSG, SOG, organic antireflective coating, etc.) or a substrate for mask circuit fabrication (e.g., Cr, CrO, CrON, $MoSi_2$, Si, SiO, $SiO_2$, etc.) by a suitable coating technique such as spin coating. The coating is prebaked on a hotplate at a temperature of 60 to 150° C. for 1 to 20 minutes, preferably at 80 to 140° C. for 1 to 10 minutes to form a resist film of 0.03 to 2 m thick.

Then the resist film is exposed patternwise to high-energy radiation such as UV, deep UV, excimer laser, EUV, x-ray, γ-ray or synchrotron radiation through a mask having a desired pattern or directly by EB writing. The exposure dose is preferably 1 to 300 $mJ/cm^2$, more preferably 10 to 200 $mJ/cm^2$ in the case of high-energy radiation or 1 to 300 $\mu C/cm^2$, more preferably 10 to 200 $\mu C/cm^2$ in the case of EB. The resist composition of the invention is especially effective on patternwise exposure to KrF, EUV or EB. The exposure may be performed by conventional lithography whereas the immersion lithography of holding a liquid between the mask and the resist film may be employed if desired. When the immersion lithography is applied, a protective film which is insoluble in water may be formed on the resist film.

The resist film is then baked (PEB) on a hotplate at 60 to 150° C. for 1 to 20 minutes, preferably at 80 to 140° C. for 1 to 10 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

From the resist composition, a pattern with a high resolution and minimal LER may be formed. The resist composition is effectively applicable to a processable substrate, specifically a substrate having a surface layer of material to which a resist film is less adherent and which is likely to invite pattern stripping or pattern collapse, and particularly a substrate having sputter deposited thereon metallic chromium or a chromium compound containing at least one light element selected from oxygen, nitrogen and carbon or a substrate having an outermost surface layer of SiO$_x$. The invention is especially effective for pattern formation on a photomask blank as the substrate.

Even on use of a processable substrate having an outermost surface layer made of a chromium or silicon-containing material which tends to adversely affect the profile of resist pattern, typically photomask blank, the resist pattern forming process is successful in forming a pattern with a high resolution and reduced LER via exposure to high-energy to radiation because the resist composition is effective for controlling acid diffusion at the substrate interface.

EXAMPLE

Examples of the invention are given below by way of illustration and not by way of limitation. The abbreviation "pbw" is parts by weight. THF is tetrahydrofuran. The copolymer composition is expressed by a molar ratio. Mw is measured by GPC versus polystyrene standards. Analytic instruments are as shown below.

IR: NICOLET 6700 by Thermo Fisher Scientific Inc.
$^1$H-NMR: ECA-500 by JEOL Ltd.
$^{19}$F-NMR: ECA-500 by JEOL Ltd.
LC-MS: ACQUITY UPLC H-Class system and ACQUITY QDa by Waters.

1) Synthesis of Sulfonium Compounds

Synthesis Example 1

Synthesis of 2-(diphenylsulfonio)phenolate Q-1

Synthesis Example 1-1

Synthesis of (2-tert-butoxyphenyl)diphenylsulfonium chloride (Intermediate A)

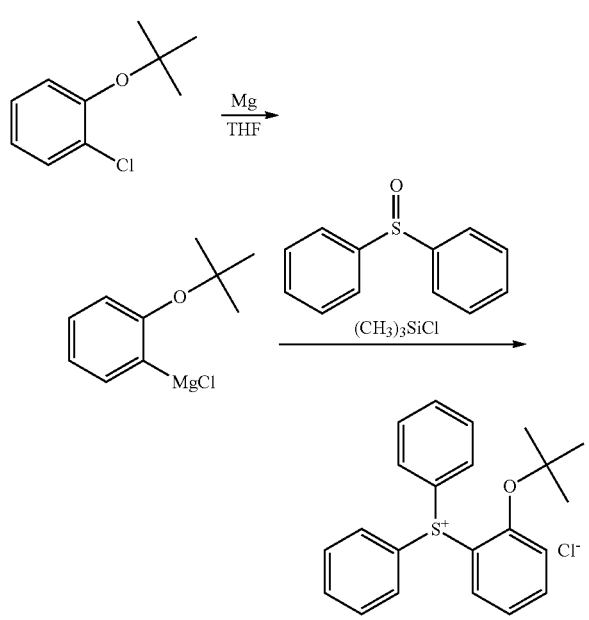

A Grignard reagent was prepared in THF by the standard method using 2.6 g of magnesium and 16 g of 2-tert-butoxychlorobenzene. To the Grignard reagent were added 6.1 g of diphenyl sulfoxide and 27 g of THF. Then 9.8 g of chlorotrimethylsilane was added dropwise at room temperature to the solution, which was aged for 3 hours. After aging, a saturated ammonium chloride aqueous solution was added to quench the reaction, and 100 g of water was added to the reaction solution, which was washed with diisopropyl ether, yielding an aqueous solution of the target compound, (2-tert-butoxyphenyl)diphenylsulfonium chloride, designated Intermediate A. The compound was fed to the next step without isolation.

Synthesis Example 1-2

Synthesis of (2-hydroxyphenyl)diphenylsulfonium tosylate (Intermediate B)

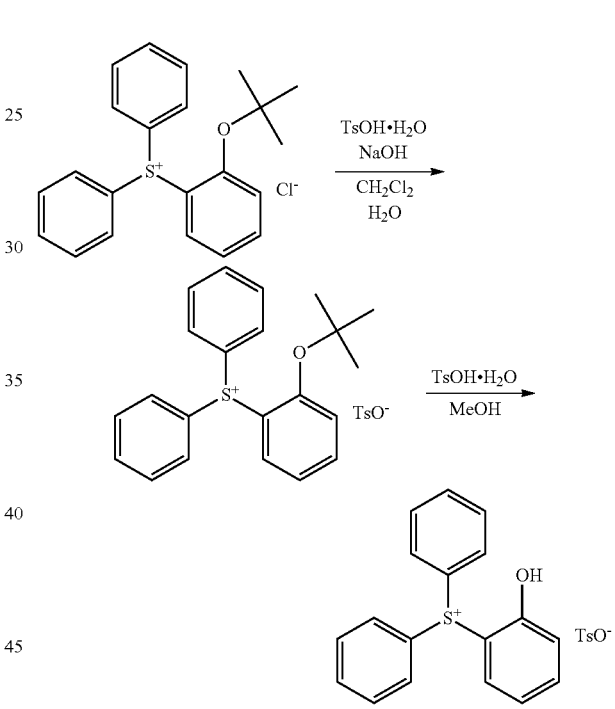

To the entire amount of the Intermediate A solution, 6.8 g of p-toluenesulfonic acid monohydrate, 6.1 g of 25 wt % sodium hydroxide aqueous solution, 30 g of water and 150 g of methylene chloride were added and stirred for 30 minutes. The organic layer was taken out, washed with water, and concentrated under reduced pressure to remove methylene chloride, yielding a crude form of (2-tert-butoxyphenyl)diphenylsulfonium tosylate. To the crude form were added 6 g of p-toluenesulfonic acid monohydrate and 50 g of methanol. The solution was held at 80° C. for 14 hours for deprotection reaction. The reaction solution was concentrated at 60° C. under reduced pressure, methylene chloride was added, and the organic layer was washed with ultrapure water. After washing, the organic layer was concentrated under reduced pressure. To the residue, tert-butyl methyl ether was added for recrystallization. The resulting crystal was collected and dried in vacuum, obtaining the target compound, (2-hydroxyphenyl)diphenylsulfonium tosylate,

Synthesis Example 1-3

Synthesis of 2-(diphenylsulfonio)phenolate Q-1

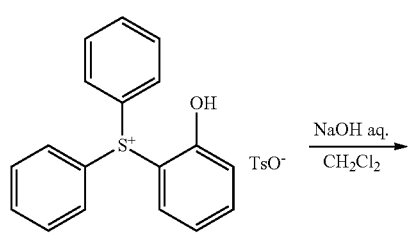

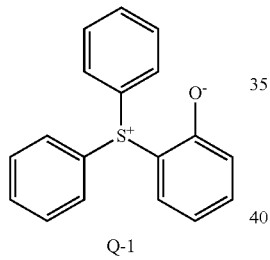

Q-1

To a solution of 4.5 g of Intermediate B in 22 g of methylene chloride, 1.6 g of 25 wt % sodium hydroxide aqueous solution and 10 g of pure water were added and stirred for 30 minutes. After stirring, 1-pentanol was added, and the organic layer was taken out, washed with water, and concentrated under reduced pressure. Methyl isobutyl ketone was added to the concentrate, which was concentrated under reduced pressure again. To the residue, diisopropyl ether was added for recrystallization. The resulting crystal was collected and dried in vacuum, obtaining the target compound, 2-(diphenylsulfonio)phenolate Q-1. Amount 2.5 g, yield 91%.

The target compound was analyzed by spectroscopy. The NMR spectrum, $^1$H-NMR in DMSO-$d_6$ is shown in FIG. 1. In $^1$H-NMR analysis, minute amounts of residual solvents (diisopropyl ether, methyl isobutyl ketone) and water were observed.

IR (D-ATR): ν=2990, 1580, 1485, 1478, 1442, 1360, 1285, 1007, 997, 840, 745, 724, 687 cm$^1$

LC-MS: Positive [M+H]$^+$ 279 (corresponding to $C_{18}H_{15}OS^+$)

Synthesis Example 2

Synthesis of 2-(diphenylsulfonio)-5-fluorophenolate Q-2

Synthesis Example 2-1

Synthesis of 1-bromo-2-tert-butoxy-4-fluorobenzene (Intermediate C)

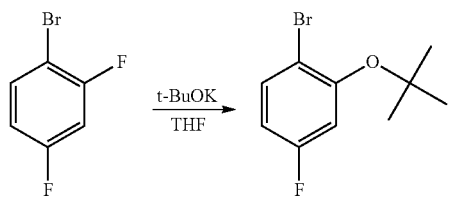

With heating at 50° C., 1 kg of 1-bromo-2,4-difluorobenzene was added dropwise to a solution of 553 g of potassium tert-butoxide in 4 kg of THF, which was aged at 50° C. for 20 hours. The reaction solution was concentrated under reduced pressure, after which 3.5 kg of hexane and 3 kg of pure water were added to the concentrate. The organic layer was taken out, washed with water, and concentrated under reduced pressure. Methanol was added to the residue for recrystallization. The resulting crystal was collected by filtration and heat dried in vacuum, obtaining the target compound, 1-bromo-2-tert-butoxy-4-fluorobenzene, designated Intermediate C. Amount 815 g, yield 66%.

Synthesis Example 2-2

Synthesis of (2-hydroxy-4-fluorophenyl)diphenylsulfonium tosylate (Intermediate D)

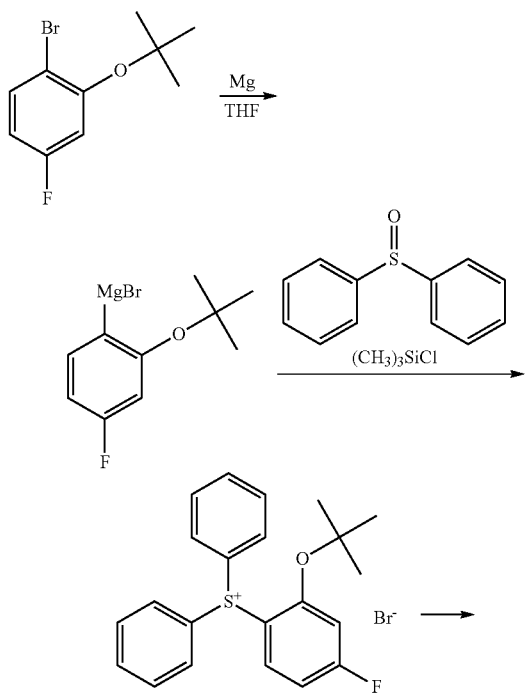

-continued

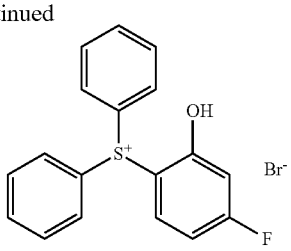

A Grignard reagent was prepared in THF by the standard method using 72 g of magnesium and 741 g of Intermediate C. To the Grignard reagent were added 202 g of diphenyl sulfoxide and 400 g of THF. With heating at 60° C., 325 g of chlorotrimethylsilane was added dropwise to the solution, which was aged for 15 hours. After aging, the reaction solution was ice cooled, and 104 g of 35 wt % hydrochloric acid and 2,300 g of pure water were added to quench the reaction. Thereafter, 2.5 kg of diisopropyl ether was added to the reaction solution, from which the water layer was taken out. The water layer was combined with 200 g of 35 wt % hydrochloric acid and aged at 60° C. for 5 hours, allowing crystals to precipitate. The crystal precipitate was collected by filtration, washed with diisopropyl ether, and heat dried under reduced pressure, obtaining 229 g (yield 59%) of the target compound, (2-hydroxy-4-fluorophenyl) diphenylsulfonium tosylate, designated Intermediate D.

Synthesis Example 2-3

Synthesis of 2-(diphenylsulfonio)-5-fluorophenolate Q-2

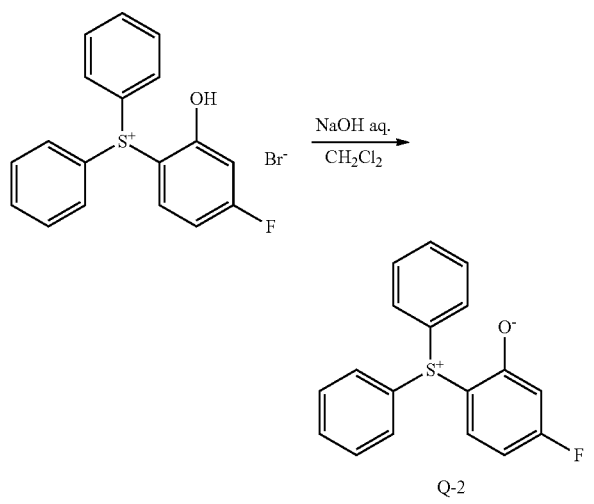

A mixture of 3.0 g of Intermediate D, 1.2 g of 25 wt % sodium hydroxide aqueous solution, 50 g of methylene chloride and 20 g of pure water was stirred for 10 minutes. Thereafter, the organic layer was taken out, washed with pure water, and concentrated under reduced pressure. Diisopropyl ether was added to the concentrate for recrystallization. The resulting crystal was collected and dried in vacuum, obtaining the target compound, 2-(diphenylsulfonio)-5-fluorophenolate Q-2. Amount 1.5 g, yield 66%.

Figure 2:
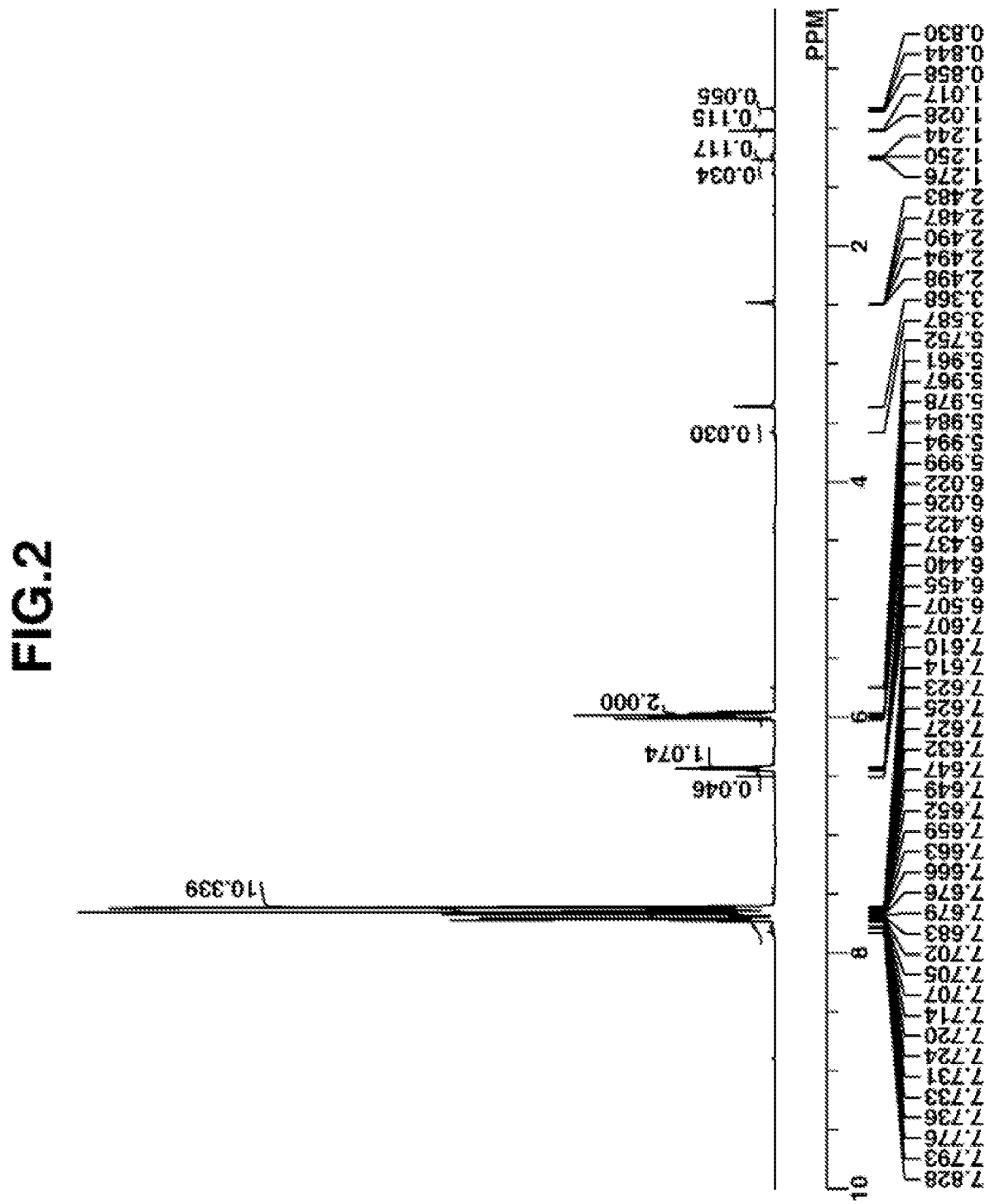
FIG. 2 is a diagram showing $^1$H-NMR spectrum of Compound Q-2 in Example 1-2.

The target compound was analyzed by spectroscopy. The NMR spectra, $^1$H-NMR and $^{19}$F-NMR in DMSO-$d_6$ are shown in FIGS. 2 and 3. In $^1$H-NMR analysis, minute amounts of residual solvents (diisopropyl ether, methyl isobutyl ketone) and water were observed.

IR (D-ATR): ν=2992, 1590, 1530, 1488, 1478, 1446, 1317, 1284, 1148, 1115, 964, 834, 763, 755, 688 cm$^{-1}$

LC-MS: Positive [M+H]$^+$ 297 (corresponding to $C_{18}H_{14}OFS^+$)

2) Synthesis of Polymers

Synthesis Example 3-1

Synthesis of Polymer 1

A 3-L flask was charged with 314.4 g of 5-acetoxyacenaphthylene, 22.0 g of 4-chlorostyrene, 190.7 g of indene, and 675 g of toluene as solvent. The reactor was cooled at −70° C. in a nitrogen atmosphere, after which vacuum pumping and nitrogen flow were repeated three times. The reactor was warmed up to room temperature, whereupon 40.5 g of 2,2'-azobis(2,4-dimethylvaleronitrile) (V-65 by Wako Pure Chemical Industries, Ltd.) was added as polymerization initiator. The reactor was heated at 45° C., whereupon reaction ran for 20 hours. The temperature was raised to 55° C., at which reaction ran for a further 20 hours. The reaction solution was concentrated to ½ in volume and poured into 15 L of methanol for precipitation. The white solid was filtered and dried in vacuum at 40° C., yielding 309 g of a white polymer.

The polymer was dissolved in 488 g of methanol and 540 g of THF again, to which 162 g of triethylamine and 32 g of water were added. The solution was kept at 60° C. for 40 hours for deprotection reaction to take place. The reaction solution was concentrated, and dissolved in 870 g of ethyl acetate. The solution was subjected to once neutralization/separatory washing with a mixture of 250 g water and 98 g acetic acid, once separatory washing with a mixture of 225 g water and 75 g pyridine, and 4 times separatory washing with 225 g water. Thereafter, the upper layer or ethyl acetate solution was concentrated, dissolved in 250 g of acetone, and poured into 15 L of water for precipitation. The precipitate was filtered and dried in vacuum at 50° C. for 40 hours, yielding 223 g of a white polymer. The polymer, designated Polymer 1, was analyzed by $^{13}$C-NMR, $^1$H-NMR and GPC, with the results shown below.

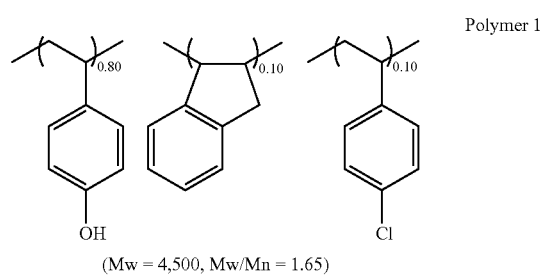

Polymer 1

(Mw = 4,500, Mw/Mn = 1.65)

Synthesis Example 3-2

Synthesis of Polymer 8

In nitrogen atmosphere, 890 g of 50.0 wt % PGMEA solution of 4-hydroxystyrene, 47.7 g of acenaphthylene, 310 g of 54.7 wt % PGMEA solution of 4-(2-hydroxy-2-propyl) styrene, 87.0 g of triphenylsulfonium 1,1,3,3,3-pentafluoro-2-methacryloyloxypropane-1-sulfonate, 96.1 g of dimethyl 2,2'-azobis(2-methylpropionate) (V-601 by Wako Pure Chemical Industries, Ltd.), and 360 g of γ-butyrolactone and 220 g of PGMEA as solvent were fed into a 3000-mL dropping cylinder to form a monomer solution. In nitrogen atmosphere, a 5000-mL polymerization flask was charged with 580 g of γ-butyrolactone, which was heated at 80° C. The monomer solution was added dropwise from the dropping cylinder to the flask over 4 hours. After the completion of dropwise addition, the polymerization solution was continuously stirred for 18 hours while maintaining its temperature at 80° C. The polymerization solution was cooled to room temperature and added dropwise to 22.5 kg of diisopropyl ether whereupon the copolymer agglomerated. Diisopropyl ether was decanted off, and the copolymer was dissolved in 2,250 g of acetone. The acetone solution was added dropwise to 22.5 kg of diisopropyl ether whereupon the copolymer precipitated. The copolymer precipitate was collected by filtration and dissolved in 2,250 g of acetone again. The acetone solution was added dropwise to 22.5 kg of water. The copolymer precipitate was collected by filtration and dried at 40° C. for 40 hours, obtaining 700 g of a white polymer. The polymer designated Polymer 8 was analyzed by $^{13}$C-NMR, $^{1}$H-NMR and GPC, with the results shown below.

Polymer 8

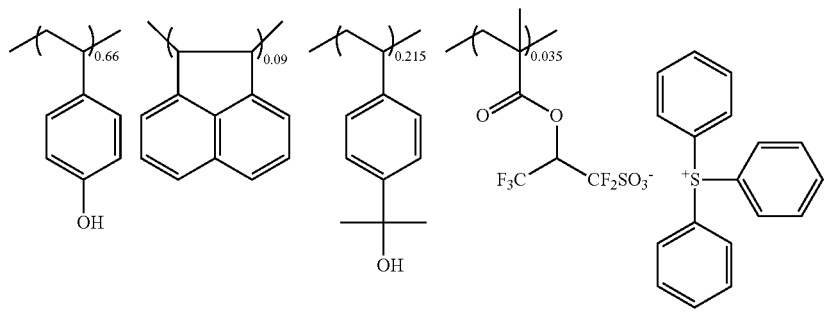

(Mw = 13,000, Mw/Mn = 1.62)

Synthesis Examples 3-3 to 3-29

Synthesis of Polymers 2 to 7, 9 to 29

Polymers 2 to 7 and 9 to 29 were synthesized by the same procedures as Polymers 1 and 8 except that the type and amount (molar ratio) of monomers were changed. For Polymers 1 to 29, the type and molar ratio of monomers are tabulated in Table 1. The structures of recurring units incorporated in the polymers are shown in Tables 2 to 6. Notably, Mw of Polymers 1 to 7, 17, 18, 20, 22 to 25, and 27 was measured versus polystyrene standards by GPC using THF solvent, and Mw of Polymers 8 to 16, 19, 21, 26, 28, and 29 was measured versus polystyrene standards by GPC using dimethylformamide solvent.

TABLE 1

| | | Unit 1 | Ratio (mol %) | Unit 2 | Ratio (mol %) | Unit 3 | Ratio (mol %) | Unit 4 | Ratio (mol %) | Unit 5 | Ratio (mol %) | Mw | Mw/Mn |
|---|---|---|---|---|---|---|---|---|---|---|---|---|---|
| Polymer | 1 | A-1 | 80.0 | B-1 | 10.0 | B-5 | 10.0 | | | | | 4,500 | 1.65 |
| | 2 | A-1 | 80.0 | B-2 | 8.0 | B-4 | 12.0 | | | | | 4,400 | 1.64 |
| | 3 | A-1 | 60.0 | B-2 | 10.0 | C-1 | 30.0 | | | | | 3,700 | 1.62 |
| | 4 | A-1 | 70.0 | B-2 | 7.0 | C-2 | 23.0 | | | | | 3,600 | 1.63 |
| | 5 | A-1 | 70.0 | B-2 | 10.0 | C-3 | 20.0 | | | | | 3,900 | 1.65 |
| | 6 | A-1 | 70.0 | B-2 | 10.0 | C-4 | 20.0 | | | | | 4,200 | 1.64 |
| | 7 | A-1 | 55.0 | B-3 | 10.0 | C-1 | 35.0 | | | | | 4,000 | 1.63 |
| | 8 | A-1 | 66.0 | B-2 | 9.0 | C-1 | 21.5 | P-1 | 3.5 | | | 13,000 | 1.62 |
| | 9 | A-1 | 60.0 | B-2 | 4.0 | C-1 | 24.0 | P-1 | 12.0 | | | 15,000 | 1.65 |
| | 10 | A-1 | 67.0 | B-2 | 10.0 | C-1 | 18.5 | P-2 | 4.5 | | | 14,000 | 1.63 |
| | 11 | A-1 | 67.0 | B-2 | 9.3 | C-1 | 20.0 | P-3 | 3.7 | | | 13,500 | 1.63 |
| | 12 | A-1 | 67.3 | B-2 | 10.0 | C-1 | 17.5 | P-4 | 5.2 | | | 13,200 | 1.64 |
| | 13 | A-1 | 64.1 | B-2 | 9.5 | C-1 | 22.0 | P-5 | 4.4 | | | 12,800 | 1.62 |
| | 14 | A-1 | 64.0 | B-2 | 10.0 | C-1 | 22.8 | P-6 | 3.2 | | | 13,500 | 1.63 |
| | 15 | A-1 | 62.0 | B-3 | 10.0 | C-1 | 24.3 | P-1 | 3.7 | | | 12,400 | 1.66 |
| | 16 | A-2 | 60.5 | B-4 | 10.0 | C-1 | 24.4 | P-2 | 5.1 | | | 12,300 | 1.65 |
| | 17 | A-1 | 80.0 | C-1 | 20.0 | | | | | | | 4,200 | 1.69 |
| | 18 | A-1 | 80.0 | B-2 | 5.0 | C-1 | 15.0 | | | | | 4,300 | 1.67 |
| | 19 | A-1 | 80.0 | B-2 | 2.5 | C-1 | 15.0 | P-1 | 2.5 | | | 12,100 | 1.69 |
| | 20 | A-2 | 50.0 | C-1 | 30.0 | F-1 | 20.0 | | | | | 4,600 | 1.67 |
| | 21 | A-2 | 50.0 | B-2 | 2.5 | C-1 | 30.0 | F-1 | 15.0 | P-1 | 2.5 | 12,700 | 1.73 |

TABLE 1-continued
| | Unit 1 | Ratio (mol %) | Unit 2 | Ratio (mol %) | Unit 3 | Ratio (mol %) | Unit 4 | Ratio (mol %) | Unit 5 | Ratio (mol %) | Mw | Mw/Mn |
|---|---|---|---|---|---|---|---|---|---|---|---|---|
| 22 | A-2 | 50.0 | C-1 | 30.0 | F-2 | 20.0 | | | | | 5,400 | 1.72 |
| 23 | A-2 | 50.0 | C-1 | 30.0 | F-3 | 20.0 | | | | | 6,100 | 1.73 |
| 24 | A-2 | 50.0 | C-1 | 30.0 | F-4 | 20.0 | | | | | 7,000 | 1.76 |
| 25 | A-1 | 67.5 | B-2 | 2.5 | C-1 | 30.0 | | | | | 4,100 | 1.65 |
| 26 | A-1 | 57.5 | B-2 | 2.5 | C-1 | 30.0 | P-5 | 10.0 | | | 11,000 | 1.65 |
| 27 | A-1 | 70.0 | C-1 | 30.0 | | | | | | | 4,000 | 1.71 |
| 28 | A-1 | 65.0 | C-1 | 25.0 | P-7 | 10.0 | | | | | 12,500 | 1.80 |
| 29 | A-1 | 65.0 | C-1 | 25.0 | P-8 | 10.0 | | | | | 13,000 | 1.77 |
TABLE 2
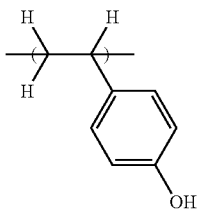
A-1
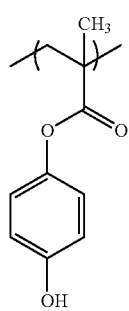
A-2
TABLE 3
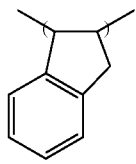
B-1
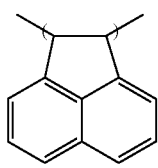
B-2
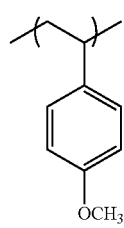
B-3
TABLE 3-continued
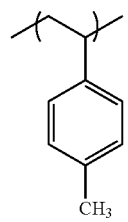
B-4
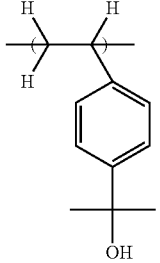
B-5
TABLE 4
C-1
C-2
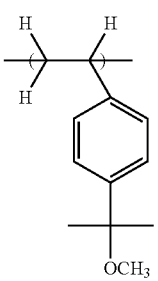

TABLE 4-continued
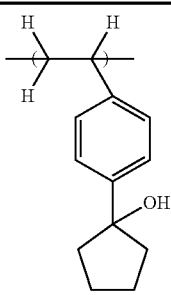 C-3
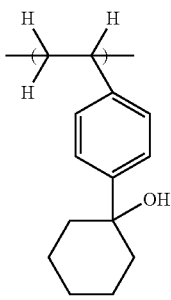 [SMILES: CCC(C)c1ccc(C2(O)CCCCC2)cc1] C-4
TABLE 5
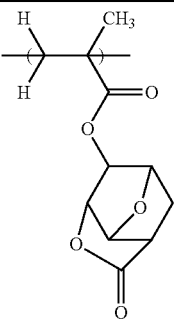 F-1
TABLE 5-continued
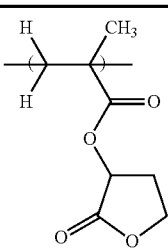 F-2
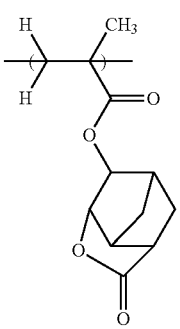 [SMILES: CCC(C)(C)C(=O)OC1C2CC3C(=O)OC1C3C2] F-3
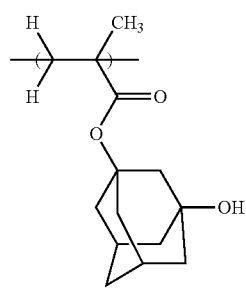 [SMILES: CCC(C)(C)C(=O)OC12CC3CC(CC(O)(C3)C1)C2] F-4
TABLE 6
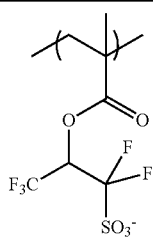 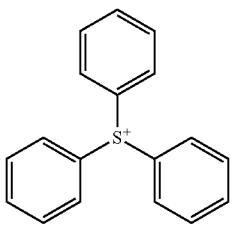 P-1
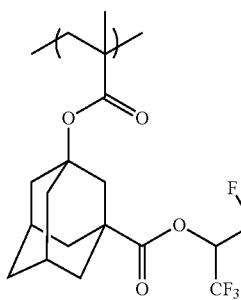 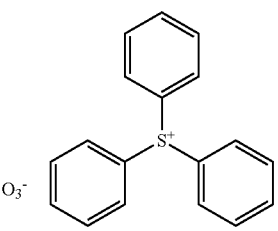 P-2

TABLE 6-continued
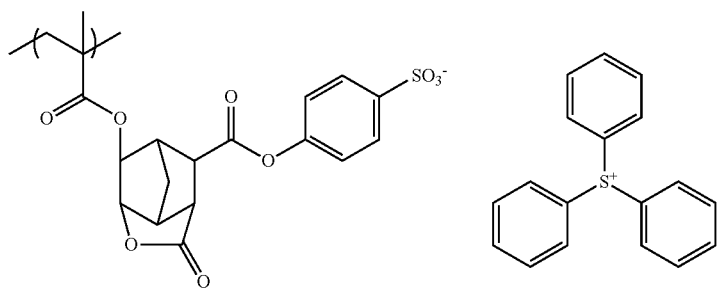
P-3
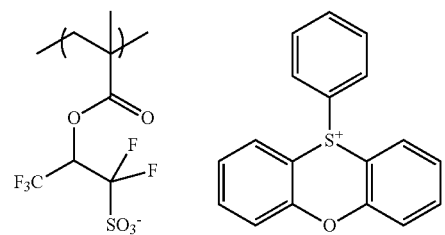
P-4
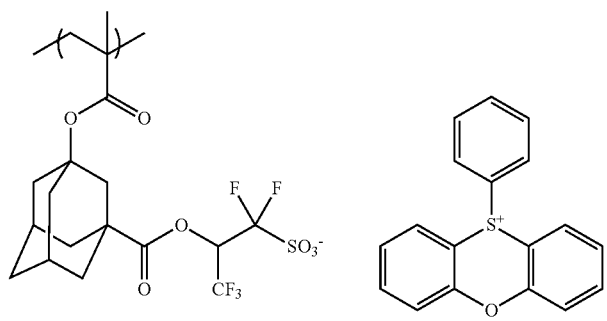
P-5
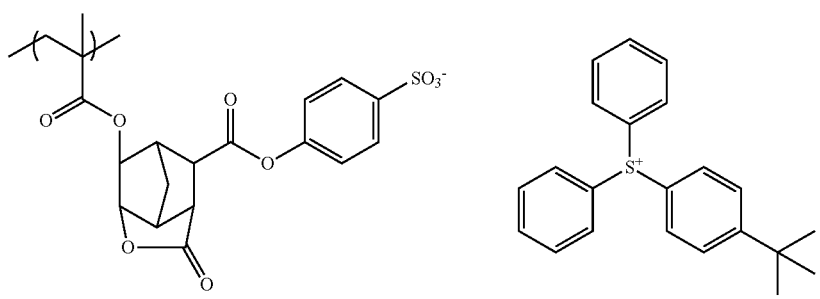
P-6
P-7
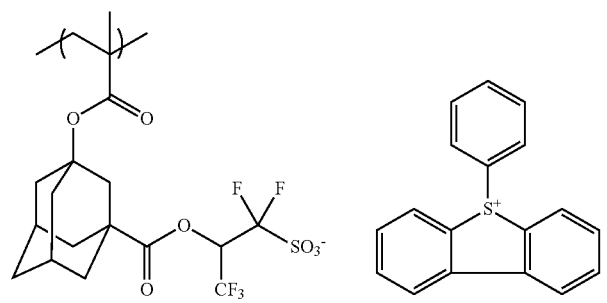

TABLE 6-continued

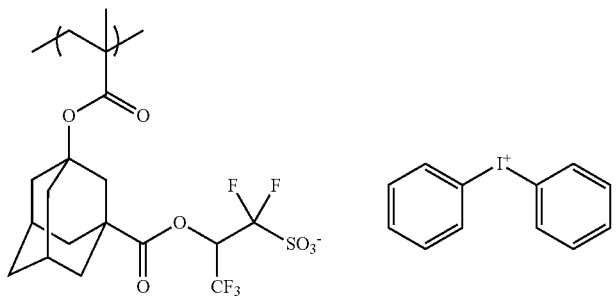

P-8

3) Preparation of Negative Resist Compositions

Examples 1-1 to 1-57 and Comparative Examples 1-1 to 1-8

Negative resist compositions (R-1 to R-57, CR-1 to CR-8) in solution form were prepared by dissolving a polymer (Polymers 1 to 24), an acid generator (PAG-A to F), and a sulfonium compound (Q-1, Q-2) of formula (A) synthesized in Synthesis Examples or comparative compound (Q-3, Q-4) as acid diffusion inhibitor in an organic solvent in accordance with the formulation shown in Tables 7 and 8, and filtering through a UPE filter and/or nylon filter with a pore size of 0.02 μm. For the resist compositions of Examples 1-1 to 1-48 and Comparative Examples 1-1 to 1-4, the organic solvent was a mixture of 1,204 pbw of PGMEA (propylene glycol monomethyl ether acetate), 1,204 pbw of EL (ethyl lactate), and 1,606 pbw of PGME (propylene glycol monomethyl ether). For the resist compositions of Examples 1-49 to 1-57 and Comparative Examples 1-5 to 1-8, the organic solvent was a mixture of 249 pbw of PGMEA and 655 pbw of EL. To some compositions, a fluorinated polymer D (Polymer D1 to D3) as additive and tetramethoxymethylglycoluril (TMGU) as crosslinker were added. Also some compositions contained surfactant PF-636 (Omnova Solutions).

The components in Tables 7 and 8 are identified below.

Q-3

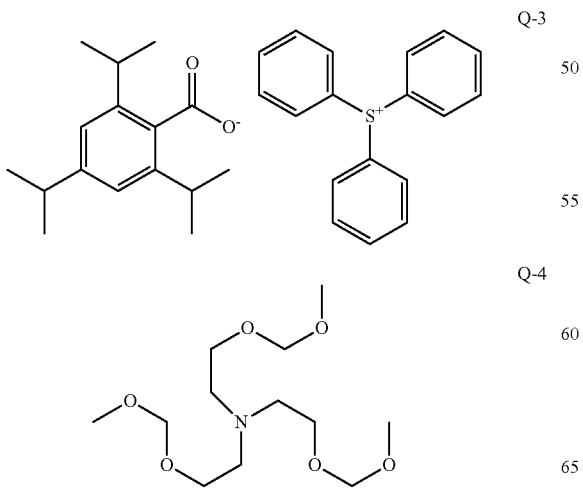

Q-4

PAG-A

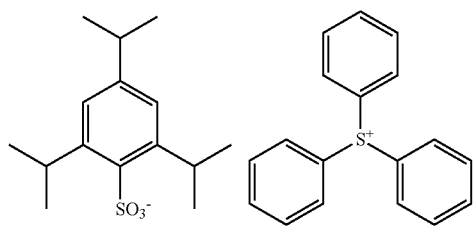

PAG-B

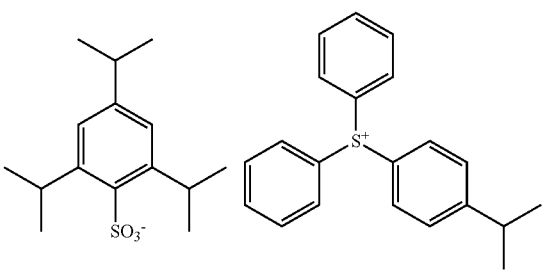

PAG-C

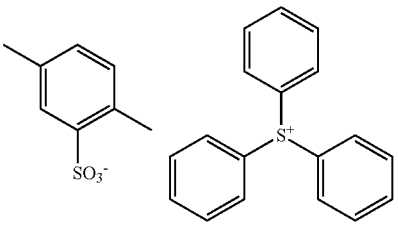

PAG-D

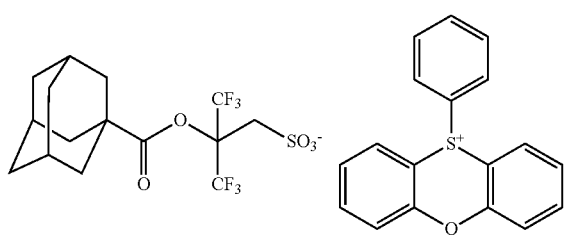

-continued

PAG-E

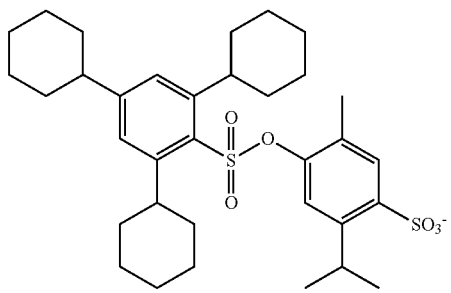

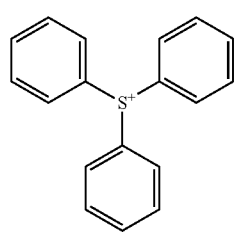

PAG-F

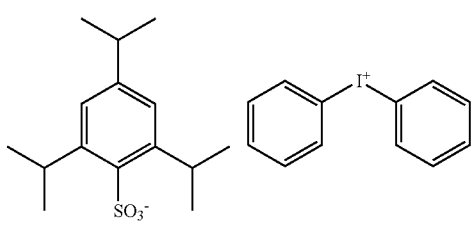

-continued

Polymer D1

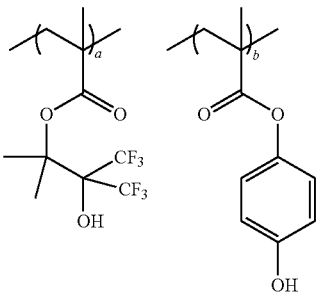

(a = 0.80, b = 0.20, Mw = 6,000)

Polymer D2

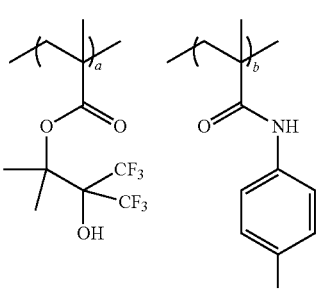

(a = 0.80, b = 0.20, Mw = 6,400)

Polymer D3

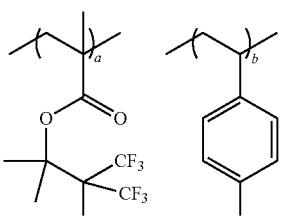

(a = 0.80, b = 0.20, Mw = 6,500)

TABLE 7

|  | Resist composition | Acid diffusion inhibitor (pbw) | Resin 1 (pbw) | Resin 2 (pbw) | Acid generator (pbw) | Crosslinker (pbw) | Additive (pbw) | Surfactant (pbw) |
|---|---|---|---|---|---|---|---|---|
| Example 1-1 | R-1 | Q-1 (2.7) | Polymer 1 (80) |  | PAG-A (2) PAG-C (8) | TMGU (8.154) |  | PF-636 (0.075) |
| 1-2 | R-2 | Q-1 (2.6) | Polymer 1 (80) |  | PAG-A (2) PAG-C (8) | TMGU (8.154) | Polymer D1 (3) | PF-636 (0.075) |
| 1-3 | R-3 | Q-1 (2.6) | Polymer 1 (80) |  | PAG-A (2) PAG-C (8) | TMGU (8.154) | Polymer D2 (3) | PF-636 (0.075) |
| 1-4 | R-4 | Q-1 (2.6) | Polymer 1 (80) |  | PAG-A (2) PAG-C (8) | TMGU (8.154) | Polymer D3 (3) | PF-636 (0.075) |
| 1-5 | R-5 | Q-1 (3.0) | Polymer 2 (80) |  | PAG-A (2) PAG-C (8) | TMGU (8.154) |  | PF-636 (0.075) |
| 1-6 | R-6 | Q-1 (2.5) | Polymer 3 (80) |  | PAG-A (10) |  |  |  |
| 1-7 | R-7 | Q-1 (2.4) | Polymer 3 (80) |  | PAG-A (10) |  | Polymer D1 (3) |  |
| 1-8 | R-8 | Q-1 (2.4) | Polymer 4 (80) |  | PAG-A (10) |  |  |  |
| 1-9 | R-9 | Q-1 (2.4) | Polymer 5 (80) |  | PAG-A (10) |  |  |  |
| 1-10 | R-10 | Q-1 (2.3) | Polymer 6 (80) |  | PAG-A (10) |  |  |  |
| 1-11 | R-11 | Q-1 (2.4) | Polymer 7 (80) |  | PAG-A (10) |  |  |  |
| 1-12 | R-12 | Q-1 (2.0) | Polymer 8 (80) |  | PAG-D (5) |  |  |  |
| 1-13 | R-13 | Q-1 (1.8) | Polymer 9 (80) |  |  |  |  |  |
| 1-14 | R-14 | Q-1 (2.7) | Polymer 9 (80) |  | PAG-D (5) |  |  |  |
| 1-15 | R-15 | Q-1 (2.6) | Polymer 10 (80) |  | PAG-D (5) |  |  |  |
| 1-16 | R-16 | Q-1 (2.4) | Polymer 11 (80) |  | PAG-D (5) |  |  |  |

TABLE 7-continued

| | Resist compo-sition | Acid diffusion inhibitor (pbw) | Resin 1 (pbw) | Resin 2 (pbw) | Acid generator (pbw) | Crosslinker (pbw) | Additive (pbw) | Surfactant (pbw) |
|---|---|---|---|---|---|---|---|---|
| 1-17 | R-17 | Q-1 (2.6) | Polymer 12 (80) | | PAG-D (5) | | | |
| 1-18 | R-18 | Q-1 (2.4) | Polymer 13 (80) | | PAG-D (5) | | | |
| 1-19 | R-19 | Q-1 (2.4) | Polymer 14 (80) | | PAG-D (5) | | | |
| 1-20 | R-20 | Q-1 (2.4) | Polymer 15 (80) | | PAG-D (5) | | | |
| 1-21 | R-21 | Q-1 (2.5) | Polymer 16 (80) | | PAG-D (5) | | | |
| 1-22 | R-22 | Q-1 (2.8) | Polymer 8 (40) | Polymer 3 (40) | PAG-A (5) | | | |
| 1-23 | R-23 | Q-1 (3.1) | Polymer 8 (40) | Polymer 3 (40) | PAG-A (5) PAG-B (2) | | | |
| 1-24 | R-24 | Q-1 (2.7) | Polymer 8 (40) | Polymer 3 (40) | PAG-D (7) | | | |
| 1-25 | R-25 | Q-1 (2.6) | Polymer 8 (40) | Polymer 3 (40) | PAG-D (7) | | Polymer D1 (3) | |
| 1-26 | R-26 | Q-1 (2.5) | Polymer 8 (40) | Polymer 3 (40) | PAG-D (7) | | Polymer D1 (5) | |
| 1-27 | R-27 | Q-1 (2.6) | Polymer 8 (40) | Polymer 3 (40) | PAG-E (7) | | | |
| 1-28 | R-28 | Q-1 (2.5) | Polymer 8 (40) | Polymer 3 (40) | PAG-E (7) | | Polymer D1 (3) | |
| 1-29 | R-29 | Q-1 (2.5) | Polymer 8 (40) | Polymer 3 (40) | PAG-E (7) | | Polymer D2 (3) | |
| 1-30 | R-30 | Q-1 (2.5) | Polymer 8 (40) | Polymer 3 (40) | PAG-E (7) | | Polymer D3 (3) | |
| 1-31 | R-31 | Q-1 (2.7) | Polymer 8 (40) | Polymer 4 (40) | PAG-E (7) | | | |
| 1-32 | R-32 | Q-1 (2.4) | Polymer 8 (40) | Polymer 5 (40) | PAG-E (7) | | | |
| 1-33 | R-33 | Q-1 (2.5) | Polymer 8 (40) | Polymer 6 (40) | PAG-E (7) | | | |
| 1-34 | R-34 | Q-1 (2.3) | Polymer 8 (40) | Polymer 6 (40) | PAG-E (7) | | | |
| 1-35 | R-35 | Q-1 (2.2) | Polymer 9 (30) | Polymer 3 (50) | PAG-D (3) | | | |
| 1-36 | R-36 | Q-1 (2.5) | Polymer 10 (40) | Polymer 3 (40) | PAG-D (5) | | | |
| 1-37 | R-37 | Q-1 (2.4) | Polymer 11 (40) | Polymer 3 (40) | PAG-D (5) | | | |
| 1-38 | R-38 | Q-1 (2.4) | Polymer 12 (40) | Polymer 3 (40) | PAG-D (5) | | | |
| 1-39 | R-39 | Q-1 (2.5) | Polymer 13 (40) | Polymer 3 (40) | PAG-D (5) | | | |
| 1-40 | R-40 | Q-1 (2.4) | Polymer 14 (40) | Polymer 3 (40) | PAG-D (5) | | | |

TABLE 8

| | | Resist compo-sition | Acid diffusion inhibitor (pbw) | Resin 1 (pbw) | Resin 2 (pbw) | Acid generator (pbw) | Crosslinker (pbw) | Additive (pbw) | Surfactant (pbw) |
|---|---|---|---|---|---|---|---|---|---|
| Example | 1-41 | R-41 | Q-1 (2.8) | Polymer 15 (40) | Polymer 3 (40) | PAG-D (5) | | | |
| | 1-42 | R-42 | Q-1 (2.6) | Polymer 16 (40) | Polymer 3 (40) | PAG-D (5) | | | |
| | 1-43 | R-43 | Q-2 (2.9) | Polymer 1 (80) | | PAG-A (2) PAG-C (8) | TMGU (8.154) | | PF-636 (0.075) |
| | 1-44 | R-44 | Q-2 (2.9) | Polymer 1 (80) | | PAG-A (2) PAG-C (8) | TMGU (8.154) | Polymer D1 (3) | PF-636 (0.075) |
| | 1-45 | R-45 | Q-2 (2.7) | Polymer 8 (40) | Polymer 3 (40) | PAG-D (7) | | | |
| | 1-46 | R-46 | Q-2 (2.6) | Polymer 8 (40) | Polymer 3 (40) | PAG-D (7) | | Polymer D1 (3) | |
| | 1-47 | R-47 | Q-2 (2.4) | Polymer 8 (40) | Polymer 3 (40) | PAG-E (7) | | | |
| | 1-48 | R-48 | Q-2 (2.3) | Polymer 8 (40) | Polymer 3 (40) | PAG-E (7) | | Polymer D1 (3) | |
| | 1-49 | R-49 | Q-1 (1.0) | Polymer 17 (80) | | PAG-A (4) | | | |
| | 1-50 | R-50 | Q-1 (1.0) | Polymer 17 (80) | | PAG-A (4) | | Polymer D1 (3) | |
| | 1-51 | R-51 | Q-1 (1.0) | Polymer 18 (80) | | PAG-A (4) | | | |
| | 1-52 | R-52 | Q-1 (1.0) | Polymer 19 (80) | | PAG-A (4) | | | |
| | 1-53 | R-53 | Q-1 (1.0) | Polymer 20 (80) | | PAG-A (4) | | | |
| | 1-54 | R-54 | Q-1 (1.0) | Polymer 21 (80) | | PAG-A (4) | | | |
| | 1-55 | R-55 | Q-1 (1.0) | Polymer 22 (80) | | PAG-A (4) | | | |
| | 1-56 | R-56 | Q-1 (1.0) | Polymer 23 (80) | | PAG-A (4) | | | |
| | 1-57 | R-57 | Q-1 (1.0) | Polymer 24 (80) | | PAG-A (4) | | | |
| Comparative Example | 1-1 | CR-1 | Q-3 (5.5) | Polymer 1 (80) | | PAG-A (2) PAG-C (8) | TMGU (8.154) | | PF-636 (0.075) |
| | 1-2 | CR-2 | Q-3 (5.0) | Polymer 8 (40) | Polymer 3 (40) | PAG-D (7) | | | |
| | 1-3 | CR-3 | Q-4 (2.5) | Polymer 1 (80) | | PAG-A (2) PAG-C (8) | TMGU (8.154) | | PF-636 (0.075) |
| | 1-4 | CR-4 | Q-4 (1.8) | Polymer 8 (40) | Polymer 3 (40) | PAG-D (7) | | | |
| | 1-5 | CR-5 | Q-3 (1.0) | Polymer 19 (80) | | PAG-A (4) | | | |
| | 1-6 | CR-6 | Q-4 (0.5) | Polymer 19 (80) | | PAG-A (4) | | | |
| | 1-7 | CR-7 | Q-3 (1.0) | Polymer 20 (80) | | PAG-A (4) | | | |
| | 1-8 | CR-8 | Q-4 (0.5) | Polymer 20 (80) | | PAG-A (4) | | | |

4) EB Writing Test

Examples 2-1 to 2-48 and Comparative Examples 2-1 to 2-4

Using a coater/developer system ACT-M (Tokyo Electron Ltd.), each of the negative resist compositions (R-1 to R-48 and CR-1 to CR-4) was spin coated on a mask blank of 152 mm squares having a silicon oxide film at the outermost surface, which had been vapor primed with hexamethyldisilazane (HMDS), and prebaked on a hotplate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000Plus (NuFlare Technology Inc., accelerating voltage 50 kV), then baked (PEB) at 120° C. for 600 seconds, and developed in a 2.38 wt % tetramethylammonium hydroxide (TMAH) aqueous solution, thereby yielding negative patterns.

The patterned mask blank was observed under a top-down scanning electron microscope (TDSEM). The optimum dose (Eop) was defined as the exposure dose ($\mu C/cm^2$) which provided a 1:1 resolution at the top and bottom of a 200-nm 1:1 line-and-space pattern. The LS resolution (or maximum resolution) was defined as the minimum line width of a L/S pattern that could be resolved at the optimum dose. The dot resolution (or maximum resolution) was defined as the minimum size of a pattern that could be resolved at the exposure dose capable of resolving a dot (line width) of 200 nm squares to square. The LER of a 200-nm L/S pattern was measured under SEM. The pattern was visually observed to judge whether or not the pattern profile was rectangular. Using the dose providing 1:1 resolution as reference, a change of CD per C was determined from the dose curve. The test results are shown in Table 9.

TABLE 9

| | | Resist composition | Eop ($\mu C/cm^2$) | Maximum resolution L/S (nm) | Maximum resolution dot (nm) | CD change (nm) | LER (nm) | Pattern profile |
|---|---|---|---|---|---|---|---|---|
| Example | 2-1 | R-1 | 50 | 50 | 80 | 1.13 | 5.1 | rectangular |
| | 2-2 | R-2 | 51 | 50 | 80 | 1.11 | 5.2 | rectangular |
| | 2-3 | R-3 | 52 | 50 | 80 | 1.16 | 5.1 | rectangular |
| | 2-4 | R-4 | 48 | 50 | 80 | 1.11 | 5.1 | rectangular |
| | 2-5 | R-5 | 49 | 50 | 80 | 1.12 | 5.2 | rectangular |
| | 2-6 | R-6 | 49 | 40 | 70 | 1.09 | 4.8 | rectangular |
| | 2-7 | R-7 | 50 | 40 | 70 | 1.06 | 4.9 | rectangular |
| | 2-8 | R-8 | 50 | 40 | 70 | 1.05 | 4.8 | rectangular |
| | 2-9 | R-9 | 51 | 40 | 70 | 1.05 | 4.7 | rectangular |
| | 2-10 | R-10 | 50 | 40 | 70 | 1.06 | 4.7 | rectangular |
| | 2-11 | R-11 | 49 | 40 | 70 | 1.06 | 4.8 | rectangular |
| | 2-12 | R-12 | 48 | 40 | 70 | 1.05 | 4.7 | rectangular |
| | 2-13 | R-13 | 48 | 40 | 70 | 1.07 | 4.8 | rectangular |
| | 2-14 | R-14 | 49 | 40 | 70 | 1.07 | 4.8 | rectangular |
| | 2-15 | R-15 | 50 | 40 | 70 | 1.07 | 4.8 | rectangular |
| | 2-16 | R-16 | 50 | 40 | 70 | 1.05 | 4.9 | rectangular |
| | 2-17 | R-17 | 51 | 40 | 70 | 1.06 | 4.9 | rectangular |
| | 2-18 | R-18 | 52 | 40 | 70 | 1.06 | 4.8 | rectangular |
| | 2-19 | R-19 | 52 | 40 | 70 | 1.05 | 4.9 | rectangular |
| | 2-20 | R-20 | 49 | 40 | 70 | 1.05 | 4.8 | rectangular |
| | 2-21 | R-21 | 50 | 40 | 70 | 1.05 | 4.7 | rectangular |
| | 2-22 | R-22 | 50 | 40 | 70 | 1.08 | 4.7 | rectangular |
| | 2-23 | R-23 | 49 | 40 | 70 | 1.05 | 4.8 | rectangular |
| | 2-24 | R-24 | 52 | 37 | 65 | 1.01 | 4.5 | rectangular |
| | 2-25 | R-25 | 51 | 37 | 65 | 0.99 | 4.5 | rectangular |
| | 2-26 | R-26 | 51 | 37 | 65 | 1.01 | 4.6 | rectangular |
| | 2-27 | R-27 | 51 | 37 | 65 | 1.06 | 4.6 | rectangular |
| | 2-28 | R-28 | 52 | 37 | 65 | 1.04 | 4.6 | rectangular |
| | 2-29 | R-29 | 50 | 37 | 65 | 1.03 | 4.7 | rectangular |
| | 2-30 | R-30 | 49 | 37 | 65 | 1.06 | 4.7 | rectangular |
| | 2-31 | R-31 | 49 | 37 | 65 | 1.05 | 4.6 | rectangular |
| | 2-32 | R-32 | 50 | 37 | 65 | 1.05 | 4.7 | rectangular |
| | 2-33 | R-33 | 52 | 37 | 65 | 1.07 | 4.6 | rectangular |
| | 2-34 | R-34 | 50 | 37 | 65 | 1.08 | 4.7 | rectangular |
| | 2-35 | R-35 | 50 | 40 | 70 | 1.07 | 4.7 | rectangular |
| | 2-36 | R-36 | 51 | 40 | 70 | 1.05 | 4.6 | rectangular |
| | 2-37 | R-37 | 51 | 40 | 70 | 1.06 | 4.7 | rectangular |
| | 2-38 | R-38 | 52 | 40 | 70 | 1.06 | 4.7 | rectangular |
| | 2-39 | R-39 | 49 | 40 | 70 | 1.04 | 4.6 | rectangular |
| | 2-40 | R-40 | 49 | 40 | 70 | 1.05 | 4.7 | rectangular |
| | 2-41 | R-41 | 48 | 40 | 70 | 1.05 | 4.7 | rectangular |
| | 2-42 | R-42 | 50 | 40 | 70 | 1.05 | 4.7 | rectangular |
| | 2-43 | R-43 | 50 | 50 | 80 | 1.05 | 5.2 | rectangular |
| | 2-44 | R-44 | 51 | 50 | 80 | 1.06 | 5.2 | rectangular |
| | 2-45 | R-45 | 52 | 40 | 70 | 1.06 | 4.8 | rectangular |
| | 2-46 | R-46 | 49 | 40 | 70 | 1.08 | 4.9 | rectangular |
| | 2-47 | R-47 | 49 | 45 | 75 | 1.07 | 4.8 | rectangular |
| | 2-48 | R-48 | 48 | 45 | 75 | 1.06 | 4.8 | rectangular |

TABLE 9-continued

|  |  | Resist compo-sition | Eop (μC/cm$^2$) | Maximum resolution L/S (nm) | Maximum resolution dot (nm) | CD change (nm) | LER (mn) | Pattern profile |
|---|---|---|---|---|---|---|---|---|
| Comparative Example | 2-1 | CR-1 | 50 | 65 | 100 | 1.55 | 6.2 | undercut |
|  | 2-2 | CR-2 | 49 | 60 | 95 | 1.57 | 5.9 | footing |
|  | 2-3 | CR-3 | 51 | 65 | 110 | 1.46 | 6.4 | undercut |
|  | 2-4 | CR-4 | 51 | 60 | 95 | 1.44 | 6.2 | footing |

All the inventive resist compositions (R-1 to R-48) comprising the sulfonium compounds having formula (A) show satisfactory results with respect to resolution, dose margin, rectangular pattern profile, and LER. The comparative resist compositions (CR-1 to CR-4) are inferior in resolution and LER. This is because the acid generated upon EB writing diffuses to the unexposed region where negative working reaction takes place to some extent, leading to a decline of contrast.

Since the inventive resist compositions comprising the sulfonium compounds having formula (A) have a higher acid-trapping ability than the resist compositions comprising the salts of Comparative Examples 2-1 and 2-2, they are less susceptible to the unwanted reaction than the comparative resist compositions. After image writing, the sulfonium compound having formula (A) converts to a phenolic compound, losing the acid diffusion controlling ability. As a result, the reaction contrast between the exposed (imaged) region and the unexposed (unimaged) region is increased. Comparative resist compositions (CR-3 and CR-4) show a low reaction contrast because the inhibitor Q-4 maintains its acid diffusion controlling ability even after image writing. Consequently, from the inventive resist compositions comprising the sulfonium compounds, patterns with satisfactory resolution and reduced edge roughness are formed.

5) KrF Lithography Test

Examples 3-1 to 3-9 and Comparative Examples 3-1 to 3-4

Each of the resist compositions (R-49 to R-57 and CR-5 to CR-8) was spin coated on a silicon wafer having an antireflective coating (DUV42 by Nissan Chemical Industries, Ltd.) of 61 nm thick, and baked on a hotplate at 100° C. for 60 seconds to form a resist film of 240 nm thick. The resist film was exposed to KrF laser radiation by means of KrF excimer laser scanner NSR-S206D (Nikon Corp., NA=0.80), then baked (PEB) for 60 seconds, and puddle developed in a 2.38 wt % TMAH aqueous solution for 60 seconds, thereby yielding a negative 1:1 line-and-space pattern. In the PEB step, an optimum temperature for a particular resist composition was employed.

The patterned wafer was observed under TD-SEM. When a dark pattern of 150 nm line/300 nm pitch was observed under SEM, the exposure dose (mJ/cm$^2$) which finished to a size of 150 nm on SEM observation was defined as the optimum dose (Eop). Also a bright pattern of 150 nm line/150 nm pitch printed at the optimum dose was observed under SEM. A size difference (dark pattern size–bright pattern size, nm) was computed. A smaller difference indicates less chemical flare or better performance. For numerically expressing the roughness of a pattern at the optimum dose, a variation of line width (30 points measured, 30 value computed) was determined and reported as LWR (nm). The pattern profile was visually judged by top-down observation and cross-sectional observation under SEM. As used herein, the "dark pattern" refers to a layout that a resist pattern is formed around a test pattern (area surrounding the test pattern is also exposed), and inversely, "bright pattern" refers to a layout that no resist pattern is formed around a test pattern (only the test pattern is exposed). The results are shown in Table 10.

TABLE 10

|  |  | Resist compo-sition | PEB (° C.) | Eop (mJ/cm$^2$) | Size difference (nm) | LWR (nm) | Pattern profile |
|---|---|---|---|---|---|---|---|
| Example | 3-1 | R-49 | 130 | 46 | 5.9 | 4.2 | rectangular |
|  | 3-2 | R-50 | 130 | 55 | 6.0 | 4.0 | rectangular |
|  | 3-3 | R-51 | 130 | 43 | 6.8 | 5.2 | rectangular |
|  | 3-4 | R-52 | 120 | 37 | 3.1 | 3.8 | rectangular |
|  | 3-5 | R-53 | 130 | 72 | 3.8 | 4.1 | rectangular |
|  | 3-6 | R-54 | 120 | 49 | 3.3 | 3.7 | rectangular |
|  | 3-7 | R-55 | 130 | 72 | 4.3 | 4.2 | rectangular |
|  | 3-8 | R-56 | 130 | 79 | 3.2 | 4.5 | rectangular |
|  | 3-9 | R-57 | 130 | 74 | 4.5 | 5.4 | rectangular |
| Com-parative Example | 3-1 | CR-5 | 120 | 44 | 16.5 | 8.2 | top reduced |
|  | 3-2 | CR-6 | 120 | 29 | 22.8 | 7.6 | footing |
|  | 3-3 | CR-7 | 130 | 53 | 12.9 | 6.5 | top reduced |
|  | 3-4 | CR-8 | 130 | 35 | 17.0 | 5.9 | footing |

It is evident from Table 10 that the inventive resist composition possesses improved lithography performance as demonstrated by little influence of chemical flare and a good pattern profile with reduced roughness.

6) EUV Lithography Test

Examples 4-1 to 4-8 and Comparative Examples 4-1 to 4-8

A resist composition was prepared by dissolving a polymer (Polymer 25 to 29), acid generator and acid diffusion inhibitor in a solvent in accordance with the recipe shown in Table 11, and filtering through a Teflon® filter having a pore size of 0.2 m. After a silicon wafer was baked at 200° C. for drying and vapor primed with HMDS at 100° C. for 90 seconds, the resist composition was spin coated on the silicon wafer and prebaked on a hotplate at 110° C. for 60 seconds to form a resist film of 30 nm thick. Using a scanner NXE3300 (ASML, NA 0.33, dipole 90), the resist film was exposed to EUV. The resist film was baked (PEB) at 120° C. for 60 seconds and puddle developed in a 2.38 wt % TMAH aqueous solution for 60 seconds to form a negative line-and-space pattern.

The resist pattern was evaluated. The patterned wafer was observed under TD-SEM. The exposure dose capable of resolving a 22-nm L/S pattern at 1:1 is reported as sensitivity. The minimum size at that dose is reported as resolution. For numerically expressing the roughness of a 22-nm L/S pattern at the optimum dose, a variation of line width (30 points measured, 3σ value computed) was determined and reported as LWR (nm). The results are shown in Table 11.

The resist pattern was evaluated. The resist pattern-bearing wafer was observed under a TD-SEM. The optimum

TABLE 11

|  |  | Polymer (pbw) | Acid generator (pbw) | Acid diffusion inhibitor (pbw) | Organic solvent (pbw) | PEB temp. (° C.) | Sensitivity (mJ/cm$^2$) | Resolution (nm) | LWR (nm) |
|---|---|---|---|---|---|---|---|---|---|
| Example | 4-1 | Polymer 25 (80) | PAG-A (4) | Q-1 (4.0) | PGMEA (1,780) EL (1,920) PGME (2,800) | 120 | 42 | 20 | 4.1 |
|  | 4-2 | Polymer 26 (80) | — | Q-1 (4.0) | PGMEA (1,780) EL (1,920) PGME (2,800) | 120 | 48 | 21 | 3.8 |
|  | 4-3 | Polymer 25 (80) | PAG-A (4) | Q-1 (4.0) | PGMEA (5,525) GBL (975) | 120 | 43 | 20 | 4.2 |
|  | 4-4 | Polymer 26 (80) | — | Q-1 (4.0) | PGMEA (5,525) GBL (975) | 120 | 49 | 22 | 3.8 |
|  | 4-5 | Polymer 27 (80) | PAG-A (8) | Q-1 (8.0) | PGMEA (5,525) GBL (975) | 120 | 41 | 19 | 4.0 |
|  | 4-6 | Polymer 27 (80) | PAG-F (8) | Q-1 (8.0) | PGMEA (5,525) GBL (975) | 120 | 33 | 22 | 4.5 |
|  | 4-7 | Polymer 28 (80) | — | Q-1 (4.0) | PGMEA (5,525) GBL (975) | 120 | 47 | 21 | 3.9 |
|  | 4-8 | Polymer 29 (80) | — | Q-1 (4.0) | PGMEA (5,525) GBL (975) | 120 | 32 | 22 | 4.3 |
| Comparative Example | 4-1 | Polymer 25 (80) | PAG-A (4) | Q-3 (4.0) | PGMEA (1,780) EL (1,920) PGME (2,800) | 120 | 41 | 20 | 6.0 |
|  | 4-2 | Polymer 25 (80) | PAG-A (4) | Q-4 (2.0) | PGMEA (1,780) EL (1,920) PGME (2,800) | 120 | no pattern resolved | — | — |
|  | 4-3 | Polymer 26 (80) | — | Q-3 (4.0) | PGMEA (1,780) EL (1,920) PGME (2,800) | 120 | 39 | 22 | 5.6 |
|  | 4-4 | Polymer 26 (80) | — | Q-4 (2.0) | PGMEA (1,780) EL (1,920) PGME (2,800) | 120 | 40 | 22 | 6.6 |
|  | 4-5 | Polymer 25 (80) | PAG-A (4) | Q-3 (4.0) | PGMEA (5,525) GBL (975) | 120 | 42 | 20 | 5.9 |
|  | 4-6 | Polymer 27 (80) | PAG-F (8) | Q-3 (8.0) | PGMEA (5,525) GBL (975) | 120 | 31 | 22 | 6.1 |
|  | 4-7 | Polymer 28 (80) | — | Q-3 (4.0) | PGMEA (5,525) GBL (975) | 120 | 42 | 21 | 5.1 |
|  | 4-8 | Polymer 29 (80) | — | Q-3 (4.0) | PGMEA (5,525) GBL (975) | 120 | 27 | 22 | 5.5 |

It is evident from Table 11 that the inventive negative resist composition has improved EUV lithography performance as demonstrated by improved resolution and reduced roughness.

7) EB Writing Test after Anti-Charging Film Coating

Examples 5-1 to 5-7 and Comparative Examples 5-1 to 5-4

Each of the negative resist compositions (R-1 to R-4, R-24 to R-26, CR-1 to CR-4) was spin coated on a 6-inch silicon wafer and baked at 110° C. for 240 seconds to form a resist film of 80 nm thick. Using a system Mark 8 (Tokyo Electron Ltd.), an electroconductive polymer composition was dispensed and spin coated over the resist film and baked on a hotplate at 90° C. for 90 seconds to form an anti-charging film of 60 nm thick. The electroconductive polymer composition used was a water dispersion of polystyrene-doped polyaniline as described in Proc. of SPIE Vol. 8522, 852200-1. Using a system HL-800D (Hitachi High-Technologies Corp.) at an accelerating voltage of 50 kV, the resist film was exposed to EB, baked (PEB) at 110° C. for 240 seconds, and developed in a 2.38 wt % TMAH aqueous solution for 80 seconds, thereby yielding a negative pattern.

dose (Eop) was defined as the exposure dose (C/cm$^2$) which provided a 1:1 resolution of a 400-nm 1:1 line-and-space pattern. The resolution (or maximum resolution) was defined as the minimum line width of a L/S pattern that could be resolved at the optimum dose. The results are shown in Table 12.

TABLE 12

|  |  | Resist composition | Eop (μC/cm$^2$) | Maximum resolution (nm) |
|---|---|---|---|---|
| Example | 5-1 | R-1 | 56 | 70 |
|  | 5-2 | R-2 | 58 | 65 |
|  | 5-3 | R-3 | 58 | 65 |
|  | 5-4 | R-4 | 57 | 65 |
|  | 5-5 | R-24 | 56 | 55 |
|  | 5-6 | R-25 | 57 | 50 |
|  | 5-7 | R-26 | 58 | 50 |
| Comparative Example | 5-1 | CR-1 | 59 | 80 |
|  | 5-2 | CR-2 | 58 | 75 |
|  | 5-3 | CR-3 | 58 | 80 |
|  | 5-4 | CR-4 | 57 | 75 |

All the inventive resist compositions of Examples 5-1 to 5-7 comprising the sulfonium compounds having formula (A) show satisfactory resolution. The comparative resist compositions are inferior in resolution. This is because the acid migrates from the anti-charging film to the resist film to cause intermixing, whereby the unwanted negative working reaction takes place in the unexposed (unimaged) region to some extent.

Since the inventive resist compositions comprising the sulfonium compounds having formula (A) have a higher salt exchange efficiency than comparative resist compositions CR-1 and CR-2, and are reduced in intermixing of acid between anti-charging film and resist film as compared with comparative resist compositions CR-3 and CR-4, they are less susceptible to the unwanted reaction than the resist compositions of Comparative Examples. As a result, patterns with satisfactory resolution are formed. A comparison of Examples 5-1 to 5-4 with Examples 5-5 to 5-7 reveals an improvement in resolution by the fluorinated polymer (D) exerting the effect of suppressing acid mixing.

8) Evaluation of Development Residue

Examples 6-1 to 6-7 and Comparative Examples 6-1 to 6-2

Using a coater/developer system ACT-M (Tokyo Electron Ltd.), each of the negative resist compositions (R-1 to R-4, R-24 to R-26, CR-3 to CR-4) was spin coated onto a mask blank of 152 mm squares having a chromium oxynitride film at the outermost surface and prebaked on a hotplate at 110° C. for 600 seconds to form a resist film of 80 nm thick. The resist film was directly (i.e., imagewise exposure omitted) baked at 120° C. for 600 seconds and puddle developed in a 2.38 wt % TMAH aqueous solution for 60 seconds. Using a mask defect monitor M2351 (Lasertec Corp.), development residues were counted. The total count of defects after development is reported in Table 13.

TABLE 13

| | | Resist composition | Total count of defects after development |
|---|---|---|---|
| Example | 6-1 | R-1 | 520 |
| | 6-2 | R-2 | 210 |
| | 6-3 | R-3 | 200 |
| | 6-4 | R-4 | 210 |
| | 6-5 | R-24 | 510 |
| | 6-6 | R-25 | 200 |
| | 6-7 | R-26 | 210 |
| Comparative Example | 6-1 | CR-3 | 520 |
| | 6-2 | CR-4 | 530 |

The resist compositions (R-2 to R-4, R-25, R-26) comprising the fluorinated polymer (D) are smaller in defect count than the resist compositions free of the fluorinated polymer. It is believed that the fluorinated polymer (D) allows a trace of negative-working matter (which will form defects upon high-temperature bake) to be washed away during development.

It has been demonstrated that by using the inventive resist composition to form a resist film and exposing it via EB, KrF excimer laser or EUV lithography, a pattern having high resolution, a small line width variation with respect to dose changes and pattern layout dependence, and a minimal LER is formed. The resist pattern forming process using the inventive resist composition is useful in the photolithography for the fabrication of microelectronic devices, especially processing of photomask blanks and wafers.

Japanese Patent Application No. 2016-255025 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A negative resist composition comprising (A) a sulfonium compound having the formula (A), (B) a base polymer containing a polymer comprising recurring units having the formula (B1), (C) a crosslinker, and (E) an acid generator,

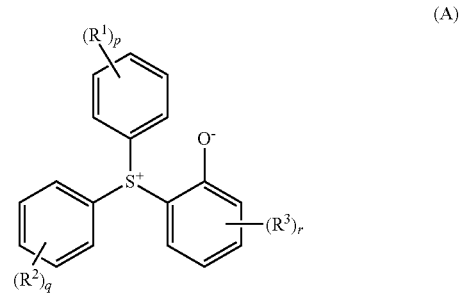

wherein $R^1$, $R^2$, and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^3$ may bond together to form a ring with the carbon atoms to which they are attached,

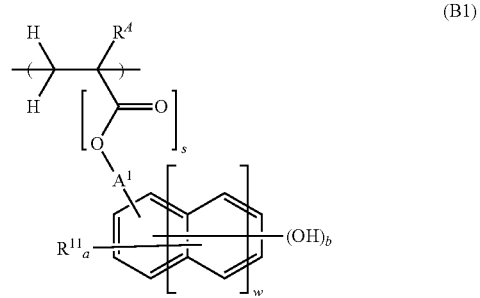

wherein $R^A$ is hydrogen, fluorine, methyl or trifluoromethyl, $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, $A^1$ is a single bond or $C_1$-$C_{10}$ straight, branched or cyclic alkylene group in which an ether bond may intervene in a carbon-carbon bond, s is 0 or 1, w is an integer of 0 to 2, a is an integer satisfying 0≤a≤5+2w−b, and b is an integer of 1 to 3.

2. The negative resist composition of claim 1 wherein the polymer further comprises recurring units of at least one type selected from recurring units having the formulae (B2), (B3) and (B4):

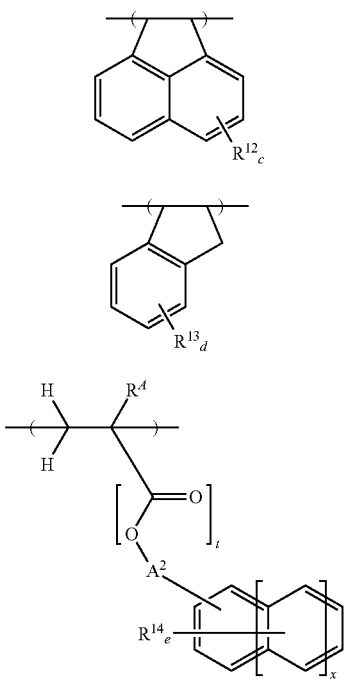

(B2)

(B3)

(B4)

wherein $R^A$ is as defined above, $R^{12}$ and $R^{13}$ are each independently hydroxyl, halogen, acetoxy, an optionally halogenated $C_2$-$C_8$ straight, branched or cyclic acyloxy group, optionally halogenated $C_1$-$C_8$ straight, branched or cyclic alkyl group, optionally halogenated $C_1$-$C_8$ straight, branched or cyclic alkoxy group, or optionally halogenated $C_2$-$C_8$ straight, branched or cyclic alkylcarbonyloxy group, $R^{14}$ is an acetyl group, acetoxy group, $C_1$-$C_{20}$ straight, branched or cyclic alkyl group, $C_1$-$C_{20}$ straight, branched or cyclic alkoxy group, $C_2$-$C_{20}$ straight, branched or cyclic acyloxy group, $C_2$-$C_{20}$ straight, branched or cyclic alkoxyalkyl group, $C_2$-$C_{20}$ alkylthioalkyl group, halogen atom, nitro group, cyano group, sulfinyl group, or sulfonyl group, $A^2$ is a single bond or $C_1$-$C_{10}$ straight, branched or cyclic alkylene group in which an ether bond may intervene in a carbon-carbon bond, c and d are each independently an integer of 0 to 4, e is an integer of 0 to 5, x is an integer of 0 to 2, and t is 0 or 1.

3. A negative resist composition comprising (A) a sulfonium compound having the formula (A), (B) a base polymer containing a polymer comprising recurring units having the formula (B1), and (E) an acid generator,

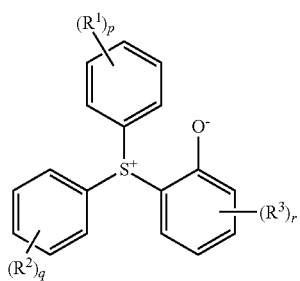

(A)

wherein $R^1$, $R^2$, and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^3$ may bond together to form a ring with the carbon atoms to which they are attached,

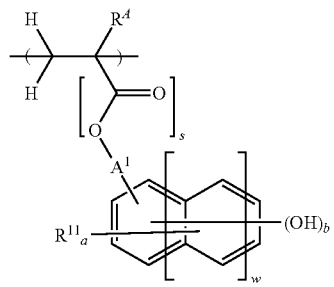

(B1)

wherein $R^A$ is hydrogen, fluorine, methyl or trifluoromethyl, $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, $A^1$ is a single bond or $C_1$-$C_{10}$ straight, branched or cyclic alkylene group in which an ether bond may intervene in a carbon-carbon bond, s is 0 or 1, w is an integer of 0 to 2, a is an integer satisfying $0 \le a \le 5+2w-b$, and b is an integer of 1 to 3, wherein the polymer further comprises recurring units having the formula (B5):

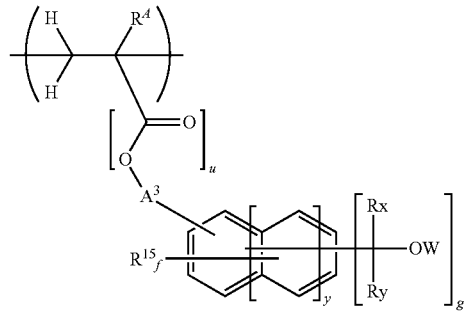

(B5)

wherein $R^A$ is as defined above, $A^3$ is a single bond or $C_1$-$C_{10}$ straight, branched or cyclic alkylene group in which an ether bond may intervene in a carbon-carbon bond, $R^{15}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, W is hydrogen, a $C_1$-$C_{10}$ straight, branched or cyclic monovalent aliphatic hydrocarbon group in which an ether, carbonyl or carbonyloxy moiety may intervene in a carbon-carbon bond, or an optionally substituted monovalent aromatic ring group, Rx and Ry are each independently hydrogen, an optionally hydroxy or alkoxy-substituted $C_1$-$C_{15}$ alkyl group or an optionally substituted monovalent aromatic ring group, with the proviso that both Rx and Ry are not hydrogen at the same time, Rx and Ry may bond together to form a ring with the carbon atom to which they are attached, y is an integer of 0 to 2, u is 0 or 1, f is an integer satisfying 0≤f≤5+2y−g, and g is an integer of 1 to 3.

4. A negative resist composition comprising (A) a sulfonium compound having the formula (A) and (B) a base polymer containing a polymer comprising recurring units having the formula (B1),

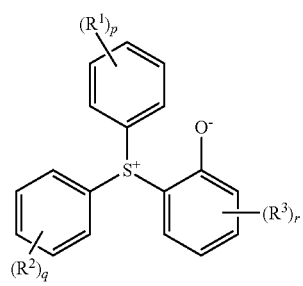
(A)

wherein $R^1$, $R^2$, and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, in case of r=2 to 4, two adjoining groups $R^3$ may bond together to form a ring with the carbon atoms to which they are attached,

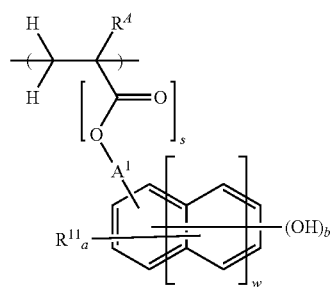
(B1)

wherein $R^A$ is hydrogen, fluorine, methyl or trifluoromethyl, $R^{11}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, $A^1$ is a single bond or $C_1$-$C_{10}$ straight, branched or cyclic alkylene group in which an ether bond may intervene in a carbon-carbon bond, s is 0 or 1, w is an integer of 0 to 2, a is an integer satisfying 0≤a≤5+2w−b, and b is an integer of 1 to 3, wherein the polymer further comprises recurring units having the formula (B5):

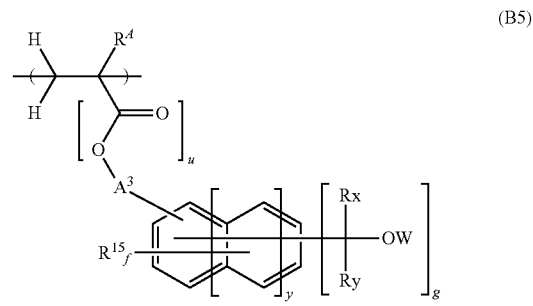
(B5)

wherein $R^A$ is as defined above, $A^3$ is a single bond or $C_1$-$C_{10}$ straight, branched or cyclic alkylene group in which an ether bond may intervene in a carbon-carbon bond, $R^{15}$ is each independently halogen, an optionally halogenated $C_2$-$C_8$ straight, branched or cyclic acyloxy group, optionally halogenated $C_1$-$C_6$ straight, branched or cyclic alkyl group, or optionally halogenated $C_1$-$C_6$ straight, branched or cyclic alkoxy group, W is hydrogen, a $C_1$-$C_{10}$ straight, branched or cyclic monovalent aliphatic hydrocarbon group in which an ether, carbonyl or carbonyloxy moiety may intervene in a carbon-carbon bond, or an optionally substituted monovalent aromatic ring group, Rx and Ry are each independently hydrogen, an optionally hydroxy or alkoxy-substituted $C_1$-$C_{15}$ alkyl group or an optionally substituted monovalent aromatic ring group, with the proviso that both Rx and Ry are not hydrogen at the same time, Rx and Ry may bond together to form a ring with the carbon atom to which they are attached, y is an integer of 0 to 2, u is 0 or 1, f is an integer satisfying 0 f 5+2y−g, and g is an integer of 1 to 3, wherein the polymer further comprises recurring units of at least one type selected from units having the formulae (a1) to (a6):

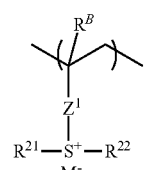
(a1)

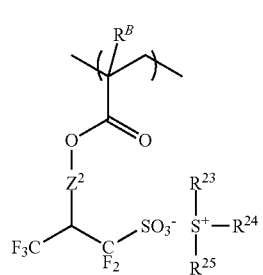
(a2)

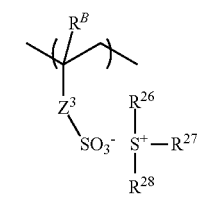
(a3)

(a4)

(a5)

(a6)

wherein $R^B$ is each independently hydrogen or methyl, $Z^1$ is a single bond, phenylene group, —O—$Z^{12}$—, or —C(=O)—$Z^{11}$-$Z^{12}$—, $Z^{11}$ is —O— or —NH—, $Z^{12}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety, $Z^2$ is a single bond or —$Z^{21}$—C(=O)—O—, $Z^{21}$ is a $C_1$-$C_{20}$ straight, branched or cyclic divalent hydrocarbon group which may contain a heteroatom-containing moiety, $Z^3$ is a single bond, methylene, ethylene, phenylene, fluorinated phenylene, —O—$Z^{32}$—, or —C(=O)—$Z^{31}$-$Z^{32}$—, $Z^{31}$ is —O— or —NH—, $Z^{32}$ is a $C_1$-$C_6$ straight, branched or cyclic alkylene, $C_2$-$C_6$ straight, branched or cyclic alkenylene or phenylene group, which may contain a carbonyl, ester, ether or hydroxy moiety, $M^-$ is a non-nucleophilic counter ion, $R^{21}$ to $R^{33}$ are each independently a $C_1$-$C_{20}$ straight, branched or cyclic monovalent hydrocarbon group which may contain a heteroatom-containing moiety, or $R^{21}$ and $R^{22}$ may bond together to form a ring with the sulfur atom to which they are attached, or any two of $R^{23}$, $R^{24}$ and $R^{25}$, or any two of $R^{26}$, $R^{27}$ and $R^{28}$ may bond together to form a ring with the sulfur atom to which they are attached.

5. The negative resist composition of claim 4 wherein the polymer comprises recurring units having the formula (B1-1), recurring units having the formula (B5-1), and recurring units having the formula (a2) or (a5):

(B1-1)

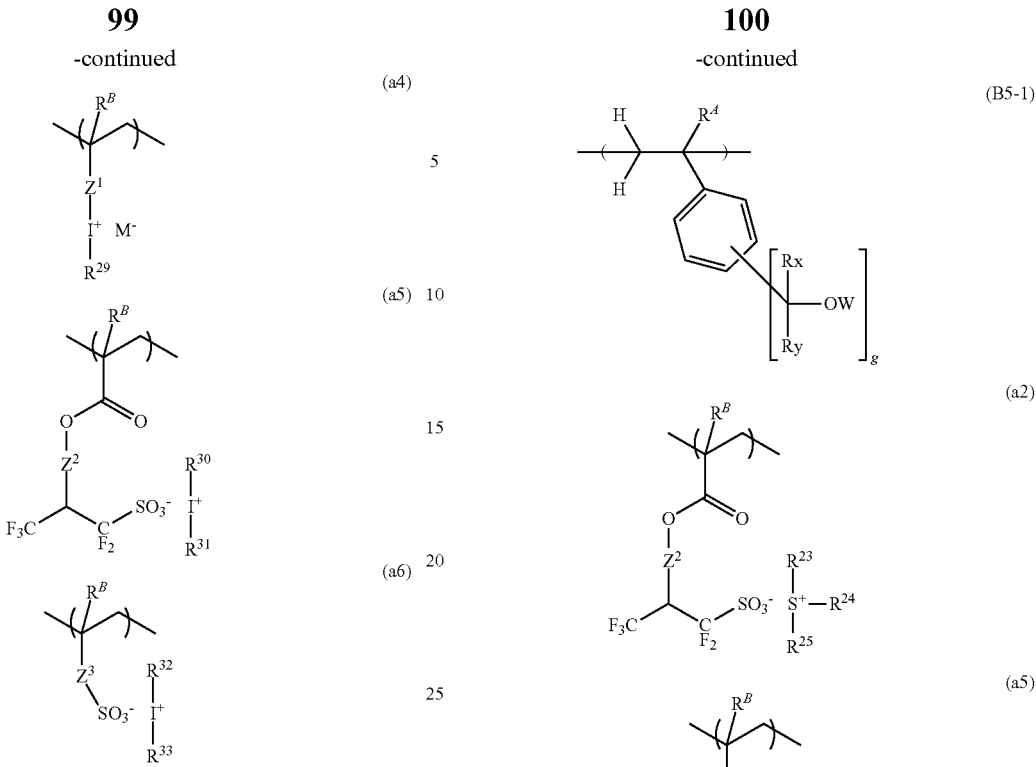

wherein $R^A$, $R^B$, $Z^2$, $R^{23}$, $R^{24}$, $R^{25}$, $R^{30}$, $R^{31}$, Rx, Ry, W, b, and g are as defined above.

6. The negative resist composition of claim 4 wherein the base polymer (B) further contains a polymer comprising recurring units having the formula (B1) and recurring units having the formula (B5), being free of recurring units having the formulae (a1) to (a6).

7. The negative resist composition of claim 3, which is free of a crosslinker.

8. The negative resist composition of claim 1, further comprising (D) a fluorinated polymer comprising recurring units having the formula (D1), and recurring units of at least one type selected from units having the formulae (D2), (D3), (D4) and (D5):

(D1)

-continued

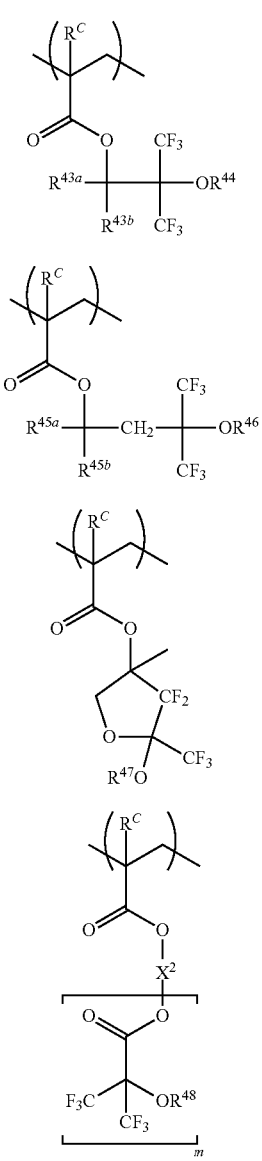

wherein $R^B$ is each independently hydrogen or methyl, $R^C$ is each independently hydrogen, fluorine, methyl or trifluoromethyl, $R^{41}$ is hydrogen or a $C_1$-$C_5$ straight or branched monovalent hydrocarbon group in which a heteroatom may intervene in a carbon-carbon bond, $R^{42}$ is a $C_1$-$C_5$ straight or branched monovalent hydrocarbon group in which a heteroatom may intervene in a carbon-carbon bond, $R^{43a}$, $R^{43b}$, $R^{45a}$ and $R^{45b}$ are each independently hydrogen or a $C_1$-$C_{10}$ straight, branched or cyclic alkyl group, $R^{44}$, $R^{46}$, $R^{47}$ and $R^{48}$ are each independently hydrogen, a $C_1$-$C_{15}$ straight, branched or cyclic monovalent hydrocarbon group or monovalent fluorinated hydrocarbon group, or an acid labile group, with the proviso that an ether or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$, h is an integer of 1 to 3, i is an integer satisfying: $0 \leq i \leq 5+2j-h$, j is 0 or 1, m is an integer of 1 to 3, $X^1$ is a single bond, —C(=O)—O— or —C(=O)—NH—, and $X^2$ is a $C_1$-$C_{20}$ straight, branched or cyclic (m+1)-valent hydrocarbon group or fluorinated hydrocarbon group.

9. The negative resist composition of claim 4, further comprising (E) an acid generator.

10. A resist pattern forming process comprising the steps of:
applying the negative resist composition of claim 1 onto a processable substrate to form a resist film thereon,
exposing the resist film patternwise to high-energy radiation, and
developing the resist film in an alkaline developer to form a resist pattern.

11. The process of claim 10 wherein the high-energy radiation is KrF excimer laser, EUV or EB.

12. The process of claim 10 wherein the processable substrate is a photomask blank.

13. The negative resist composition of claim 4, which is free of a crosslinker.

14. The negative resist composition of claim 3, further comprising (D) a fluorinated polymer comprising recurring units having the formula (D1), and recurring units of at least one type selected from units having the formulae (D2), (D3), (D4) and (D5):

103

-continued (D5)

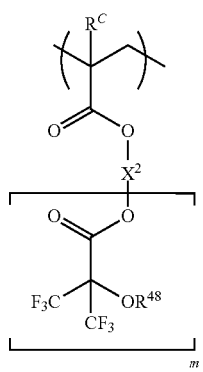

wherein $R^B$ is each independently hydrogen or methyl, $R^C$ is each independently hydrogen, fluorine, methyl or trifluoromethyl, $R^{41}$ is hydrogen or a $C_1$-$C_5$ straight or branched monovalent hydrocarbon group in which a heteroatom may intervene in a carbon-carbon bond, $R^{42}$ is a $C_1$-$C_5$ straight or branched monovalent hydrocarbon group in which a heteroatom may intervene in a carbon-carbon bond, $R^{43a}$, $R^{43b}$, $R^{45a}$ and $R^{45b}$ are each independently hydrogen or a $C_1$-$C_{10}$ straight, branched or cyclic alkyl group, $R^{44}$, $R^{46}$, $R^{47}$ and $R^{48}$ are each independently hydrogen, a $C_1$-$C_{15}$ straight, branched or cyclic monovalent hydrocarbon group or monovalent fluorinated hydrocarbon group, or an acid labile group, with the proviso that an ether or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$, h is an integer of 1 to 3, i is an integer satisfying: $0 \leq i \leq 5+2j-h$, j is 0 or 1, m is an integer of 1 to 3, $X^1$ is a single bond, —C(=O)—O— or —C(=O)—NH—, and $X^2$ is a $C_1$-$C_{20}$ straight, branched or cyclic (m+1)-valent hydrocarbon group or fluorinated hydrocarbon group.

15. The negative resist composition of claim 4, further comprising (D) a fluorinated polymer comprising recurring units having the formula (D1), and recurring units of at least one type selected from units having the formulae (D2), (D3), (D4) and (D5):

(D1)

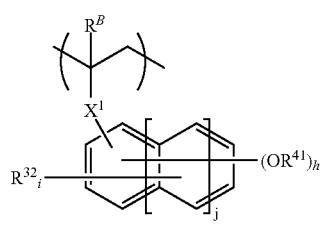

(D2)

104

-continued (D3)

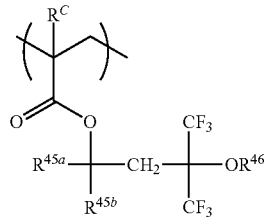

(D4)

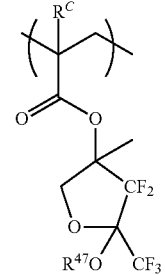

(D5)

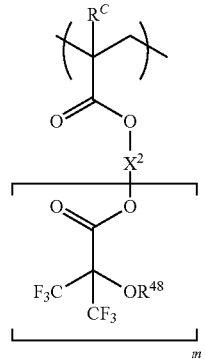

wherein $R^B$ is each independently hydrogen or methyl, $R^C$ is each independently hydrogen, fluorine, methyl or trifluoromethyl, $R^{41}$ is hydrogen or a $C_1$-$C_5$ straight or branched monovalent hydrocarbon group in which a heteroatom may intervene in a carbon-carbon bond, $R^{42}$ is a $C_1$-$C_5$ straight or branched monovalent hydrocarbon group in which a heteroatom may intervene in a carbon-carbon bond, $R^{43a}$, $R^{43b}$, $R^{45a}$ and $R^{45b}$ are each independently hydrogen or a $C_1$-$C_{10}$ straight, branched or cyclic alkyl group, $R^{44}$, $R^{46}$, $R^{47}$ and $R^{48}$ are each independently hydrogen, a $C_1$-$C_{15}$ straight, branched or cyclic monovalent hydrocarbon group or monovalent fluorinated hydrocarbon group, or an acid labile group, with the proviso that an ether or carbonyl moiety may intervene in a carbon-carbon bond in the monovalent hydrocarbon groups or monovalent fluorinated hydrocarbon groups represented by $R^{44}$, $R^{46}$, $R^{47}$ and $R^{48}$, h is an integer of 1 to 3, i is an integer satisfying: $0 \leq i \leq 5+2j-h$, j is 0 or 1, m is an integer of 1 to 3, $X^1$ is a single bond, —C(=O)—O— or —C(=O)—NH—, and $X^2$ is a $C_1$-$C_{20}$ straight, branched or cyclic (m+1)-valent hydrocarbon group or fluorinated hydrocarbon group.

16. A resist pattern forming process comprising the steps of:
  applying the negative resist composition of claim 3 onto a processable substrate to form a resist film thereon,
  exposing the resist film patternwise to high-energy radiation, and
  developing the resist film in an alkaline developer to form a resist pattern.

17. A resist pattern forming process comprising the steps of:
applying the negative resist composition of claim 4 onto a processable substrate to form a resist film thereon,
exposing the resist film patternwise to high-energy radiation, and
developing the resist film in an alkaline developer to form a resist pattern.

\* \* \* \* \*